(12) United States Patent
Hafner et al.

(10) Patent No.: US 9,017,689 B2
(45) Date of Patent: Apr. 28, 2015

(54) PEPTIDES FOR VACCINE AGAINST BIRCH ALLERGY

(75) Inventors: Roderick Peter Hafner, Oxford (GB); Paul Laidler, Oxford (GB); Guy Layton, Oxford (GB); Christopher Hugh Reginald Stocker, legal representative, Oxford (GB); Mark Larche, Hamilton (CA)

(73) Assignee: Circassia Limited, Oxford (GB)

( * ) Notice: Subject to any disclaimer, the term of this patent is extended or adjusted under 35 U.S.C. 154(b) by 0 days.

(21) Appl. No.: 13/578,888

(22) PCT Filed: Feb. 15, 2011

(86) PCT No.: PCT/GB2011/000206
§ 371 (c)(1),
(2), (4) Date: Nov. 27, 2012

(87) PCT Pub. No.: WO2011/098778
PCT Pub. Date: Aug. 18, 2011

(65) Prior Publication Data
US 2013/0243798 A1    Sep. 19, 2013

(30) Foreign Application Priority Data
Feb. 15, 2010  (GB) .................................. 1002559.1

(51) Int. Cl.
| A61K 38/00 | (2006.01) |
| A61K 39/00 | (2006.01) |
| A61K 39/35 | (2006.01) |
| A61K 39/36 | (2006.01) |
| G01N 33/00 | (2006.01) |
| G01N 33/53 | (2006.01) |

(52) U.S. Cl.
CPC ................. *A61K 39/35* (2013.01); *A61K 39/36* (2013.01)

(58) Field of Classification Search
None
See application file for complete search history.

(56) References Cited

U.S. PATENT DOCUMENTS

| 5,820,862 | A | 10/1998 | Garman et al. |
| 6,649,166 | B1 | 11/2003 | Maillere et al. |
| 2004/0241178 | A1 | 12/2004 | Spertini et al. |
| 2004/0265342 | A1 | 12/2004 | Larche et al. |
| 2006/0024334 | A1 | 2/2006 | Larche et al. |
| 2006/0216314 | A1 | 9/2006 | Westritschnig et al. |

FOREIGN PATENT DOCUMENTS

| GB | 2348808 | 10/2000 |
| WO | WO 94/01560 | 1/1994 |
| WO | WO 2004/081028 | 9/2004 |
| WO | WO 2008/139163 | 11/2008 |
| WO | WO 2008/145998 | 12/2008 |
| WO | WO 2009/022154 | 2/2009 |
| WO | WO 2010/018384 | 2/2010 |

OTHER PUBLICATIONS

Blumenthal et al. 'Definition of an Allergen.' Allergens and Allergen Immunotherapy. Ed. R Lockey, S. Bukantz and J. Bousquet. New York: Marcel Decker, 2004.37-50.*
Kinnunen et al. 'Potential of an altered peptide ligand of lipocalin allergen Bos d 2 for peptide immunotherapy.' J. Allergy Clin Immunol. 119(4):965-972, 2007.*
NCBI entry for Genbank Accession No. P35079. Retrieved on Apr. 10, 2013 (2 pages).
Engel et al., "Immunological and Biological Properties of Bet v 4, a Novel Birch Pollen Allergen with Two EF-Hand Calcium-Binding Domains," J. Biol. Chem. 272:28630-28637, 1997.
Focke et al., "Non-Anaphylactic Surface-Exposure Peptides of the Major Birch Pollen Allergen, Bet v 1, for Preventive Vaccination," Clin. Exp. Allergy 34:1525-1533, 2004.
Hufnagl et al., "Intranasal Tolerance Induction with Polypeptides Derived from 3 Noncross-Reactive Major Aeroallergens Prevents Allergic Polysensitization in Mice," J. Allergy Clin. Immunol. 116:370-376, 2005.
Nagato et al., "Functional Analysis fo Birch Pollen Allergen Bet v 1-Specific Regulatory T Cells," J. Immunol. 178:1189-1198, 2007.
Rossi et al., "Detection of Specific IgE Antibodies in the Sera of Patients Allergic to Birch Pollen Using Recombinant Allergens Bet v 1, Bet v 2, Bet v 4: Evaluation of Different IgE Reactivity Profiles," Allergy 58:929-932, 2003.
Vrtala et al., "Induction of Blocking Antibodies with T Cell Epitope-Containing Hypoallergenic Recombinant Bet v 1 Fragments," Int. Arch. Allergy Immunol. 124:107-108, 2001.
NCBI entry for Genbank Accession No. P35079. Retrieved on Oct. 4, 2013, sequence created and updated Feb. 1, 1994 (2 pages).

* cited by examiner

*Primary Examiner* — Nora Rooney
(74) *Attorney, Agent, or Firm* — Clark & Elbing LLP

(57) ABSTRACT

The present invention relates to compositions comprising peptides for preventing or treating allergy to birch, and in particular to optimal combinations of peptides for preventing or treating said allergy.

20 Claims, No Drawings

SEQUENCE LISTING

<160> NUMBER OF SEQ ID NOS: 161

<210> SEQ ID NO 1
<211> LENGTH: 16
<212> TYPE: PRT
<213> ORGANISM: Unknown
<220> FEATURE:
<223> OTHER INFORMATION: Betulaceae

```
<400> SEQUENCE: 1

Val Ile Pro Ala Ala Arg Met Phe Lys Ala Phe Ile Leu Asp Gly Asp
1               5                   10                  15

<210> SEQ ID NO 2
<211> LENGTH: 15
<212> TYPE: PRT
<213> ORGANISM: Unknown
<220> FEATURE:
<223> OTHER INFORMATION: Betulaceae

<400> SEQUENCE: 2

Ser Asn Glu Ile Lys Ile Val Ala Thr Pro Asp Gly Gly Ser Ile
1               5                   10                  15

<210> SEQ ID NO 3
<211> LENGTH: 15
<212> TYPE: PRT
<213> ORGANISM: Unknown
<220> FEATURE:
<223> OTHER INFORMATION: Betulaceae

<400> SEQUENCE: 3

Cys Asn Glu Ile Lys Ile Val Ala Thr Pro Asp Gly Gly Ser Ile
1               5                   10                  15

<210> SEQ ID NO 4
<211> LENGTH: 15
<212> TYPE: PRT
<213> ORGANISM: Unknown
<220> FEATURE:
<223> OTHER INFORMATION: Betulaceae

<400> SEQUENCE: 4

Ser Asn Glu Ile Lys Ile Val Ala Thr Pro Asp Gly Gly Cys Val
1               5                   10                  15

<210> SEQ ID NO 5
<211> LENGTH: 17
<212> TYPE: PRT
<213> ORGANISM: Unknown
<220> FEATURE:
<223> OTHER INFORMATION: Betulaceae

<400> SEQUENCE: 5

Ser Asn Glu Ile Lys Ile Val Ala Thr Pro Asn Gly Gly Ser Ile Leu
1               5                   10                  15

Lys

<210> SEQ ID NO 6
<211> LENGTH: 19
<212> TYPE: PRT
<213> ORGANISM: Unknown
<220> FEATURE:
<223> OTHER INFORMATION: Betulaceae

<400> SEQUENCE: 6

Glu Thr Leu Leu Arg Ala Val Glu Ser Tyr Leu Leu Ala His Ser Asp
1               5                   10                  15

Ala Tyr Asn

<210> SEQ ID NO 7
<211> LENGTH: 19
<212> TYPE: PRT
```

-continued

```
<213> ORGANISM: Unknown
<220> FEATURE:
<223> OTHER INFORMATION: Betulaceae

<400> SEQUENCE: 7

Glu Ala Leu Leu Arg Ala Val Glu Ser Tyr Leu Leu Ala His Ser Asp
1               5                   10                  15

Ala Tyr Asn

<210> SEQ ID NO 8
<211> LENGTH: 16
<212> TYPE: PRT
<213> ORGANISM: Unknown
<220> FEATURE:
<223> OTHER INFORMATION: Betulaceae

<400> SEQUENCE: 8

Gly Val Phe Asn Tyr Glu Ile Gly Ala Thr Ser Val Ile Pro Ala Ala
1               5                   10                  15

<210> SEQ ID NO 9
<211> LENGTH: 21
<212> TYPE: PRT
<213> ORGANISM: Unknown
<220> FEATURE:
<223> OTHER INFORMATION: Betulaceae

<400> SEQUENCE: 9

Ile Ala Pro Ala Arg Leu Phe Lys Ser Phe Val Leu Asp Ala Asp Asn
1               5                   10                  15

Leu Ile Pro Lys Val
            20

<210> SEQ ID NO 10
<211> LENGTH: 15
<212> TYPE: PRT
<213> ORGANISM: Unknown
<220> FEATURE:
<223> OTHER INFORMATION: Betulaceae

<400> SEQUENCE: 10

Cys Asn Glu Ile Lys Leu Val Ala Thr Pro Asp Gly Gly Ser Thr
1               5                   10                  15

<210> SEQ ID NO 11
<211> LENGTH: 15
<212> TYPE: PRT
<213> ORGANISM: Unknown
<220> FEATURE:
<223> OTHER INFORMATION: Betulaceae

<400> SEQUENCE: 11

Ser Lys Glu Ile Lys Ile Ala Ala Ala Pro Asp Gly Gly Ser Ile
1               5                   10                  15

<210> SEQ ID NO 12
<211> LENGTH: 15
<212> TYPE: PRT
<213> ORGANISM: Unknown
<220> FEATURE:
<223> OTHER INFORMATION: Betulaceae

<400> SEQUENCE: 12

Ser Asn Glu Ile Lys Ile Val Ala Thr Pro Asp Gly Gly Cys Ile
1               5                   10                  15
```

```
<210> SEQ ID NO 13
<211> LENGTH: 15
<212> TYPE: PRT
<213> ORGANISM: Unknown
<220> FEATURE:
<223> OTHER INFORMATION: Betulaceae

<400> SEQUENCE: 13

Cys Asn Glu Ile Lys Leu Val Ala Thr Pro Asp Gly Gly Ser Ile
1               5                   10                  15

<210> SEQ ID NO 14
<211> LENGTH: 17
<212> TYPE: PRT
<213> ORGANISM: Unknown
<220> FEATURE:
<223> OTHER INFORMATION: Betulaceae

<400> SEQUENCE: 14

Cys Asn Glu Ile Lys Ile Val Ala Ala Pro Gly Gly Gly Ser Ile Leu
1               5                   10                  15

Lys

<210> SEQ ID NO 15
<211> LENGTH: 17
<212> TYPE: PRT
<213> ORGANISM: Unknown
<220> FEATURE:
<223> OTHER INFORMATION: Betulaceae

<400> SEQUENCE: 15

Cys Asn Glu Ile Lys Ile Val Pro Ala Pro Gly Gly Gly Ser Ile Leu
1               5                   10                  15

Lys

<210> SEQ ID NO 16
<211> LENGTH: 17
<212> TYPE: PRT
<213> ORGANISM: Unknown
<220> FEATURE:
<223> OTHER INFORMATION: Betulaceae

<400> SEQUENCE: 16

Ser Tyr Glu Ile Lys Ile Val Ala Ala Pro Gly Gly Gly Ser Ile Leu
1               5                   10                  15

Lys

<210> SEQ ID NO 17
<211> LENGTH: 15
<212> TYPE: PRT
<213> ORGANISM: Unknown
<220> FEATURE:
<223> OTHER INFORMATION: Betulaceae

<400> SEQUENCE: 17

Ser Asn Glu Ile Lys Ile Val Ala Thr Gly Asp Gly Gly Ser Ile
1               5                   10                  15

<210> SEQ ID NO 18
<211> LENGTH: 15
<212> TYPE: PRT
<213> ORGANISM: Unknown
<220> FEATURE:
<223> OTHER INFORMATION: Betulaceae
```

```
<400> SEQUENCE: 18

Cys Asn Glu Ile Lys Ile Val Ala Ala Pro Asp Gly Gly Ser Ile
1               5                   10                  15

<210> SEQ ID NO 19
<211> LENGTH: 15
<212> TYPE: PRT
<213> ORGANISM: Unknown
<220> FEATURE:
<223> OTHER INFORMATION: Betulaceae

<400> SEQUENCE: 19

Ser Asn Glu Ile Lys Ile Val Ala Thr Pro Asp Gly Arg Ser Ile
1               5                   10                  15

<210> SEQ ID NO 20
<211> LENGTH: 15
<212> TYPE: PRT
<213> ORGANISM: Unknown
<220> FEATURE:
<223> OTHER INFORMATION: Betulaceae

<400> SEQUENCE: 20

Ser Asn Glu Ile Lys Leu Val Ala Thr Pro Asp Gly Gly Ser Ile
1               5                   10                  15

<210> SEQ ID NO 21
<211> LENGTH: 15
<212> TYPE: PRT
<213> ORGANISM: Unknown
<220> FEATURE:
<223> OTHER INFORMATION: Betulaceae

<400> SEQUENCE: 21

Cys Asn Glu Ile Lys Ile Val Ala Thr Pro Asp Gly Gly Cys Val
1               5                   10                  15

<210> SEQ ID NO 22
<211> LENGTH: 15
<212> TYPE: PRT
<213> ORGANISM: Unknown
<220> FEATURE:
<223> OTHER INFORMATION: Betulaceae

<400> SEQUENCE: 22

Ser Asn Glu Ile Lys Ile Val Thr Thr Pro Asp Gly Gly Cys Val
1               5                   10                  15

<210> SEQ ID NO 23
<211> LENGTH: 15
<212> TYPE: PRT
<213> ORGANISM: Unknown
<220> FEATURE:
<223> OTHER INFORMATION: Betulaceae

<400> SEQUENCE: 23

Ser Asn Glu Ile Lys Ile Val Ala Thr Pro Asp Gly Gly Pro Ile
1               5                   10                  15

<210> SEQ ID NO 24
<211> LENGTH: 17
<212> TYPE: PRT
<213> ORGANISM: Unknown
<220> FEATURE:
<223> OTHER INFORMATION: Betulaceae

<400> SEQUENCE: 24
```

```
Gly Ser Ile Leu Lys Ile Arg Asn Lys Tyr His Thr Lys Gly Asp His
1               5                   10                  15

Glu

<210> SEQ ID NO 25
<211> LENGTH: 12
<212> TYPE: PRT
<213> ORGANISM: Unknown
<220> FEATURE:
<223> OTHER INFORMATION: Betulaceae

<400> SEQUENCE: 25

Ala Gly Leu Phe Lys Ala Val Glu Asn Tyr Leu Val
1               5                   10

<210> SEQ ID NO 26
<211> LENGTH: 12
<212> TYPE: PRT
<213> ORGANISM: Unknown
<220> FEATURE:
<223> OTHER INFORMATION: Betulaceae

<400> SEQUENCE: 26

Glu Thr Leu Leu Arg Ala Val Glu Ser Tyr Leu Leu
1               5                   10

<210> SEQ ID NO 27
<211> LENGTH: 12
<212> TYPE: PRT
<213> ORGANISM: Unknown
<220> FEATURE:
<223> OTHER INFORMATION: Betulaceae

<400> SEQUENCE: 27

Glu Ala Leu Leu Arg Ala Val Glu Ser Tyr Leu Leu
1               5                   10

<210> SEQ ID NO 28
<211> LENGTH: 12
<212> TYPE: PRT
<213> ORGANISM: Unknown
<220> FEATURE:
<223> OTHER INFORMATION: Betulaceae

<400> SEQUENCE: 28

Glu Ala Leu Phe Arg Ala Val Glu Ser Tyr Leu Leu
1               5                   10

<210> SEQ ID NO 29
<211> LENGTH: 18
<212> TYPE: PRT
<213> ORGANISM: Unknown
<220> FEATURE:
<223> OTHER INFORMATION: Betulaceae

<400> SEQUENCE: 29

Glu Lys Ala Val Gly Leu Leu Lys Ala Val Glu Ser Tyr Leu Leu Ala
1               5                   10                  15

His Ser

<210> SEQ ID NO 30
<211> LENGTH: 20
<212> TYPE: PRT
<213> ORGANISM: Unknown
<220> FEATURE:
```

<223> OTHER INFORMATION: Betulaceae

<400> SEQUENCE: 30

Gly Glu Thr Leu Leu Arg Ala Val Glu Gly Tyr Leu Leu Ala His Ser
1               5                   10                  15

Asp Ala Tyr Asn
            20

<210> SEQ ID NO 31
<211> LENGTH: 15
<212> TYPE: PRT
<213> ORGANISM: Unknown
<220> FEATURE:
<223> OTHER INFORMATION: Betulaceae

<400> SEQUENCE: 31

Glu Thr Leu Leu Arg Ala Val Glu Ser Tyr Pro Leu Ala His Ser
1               5                   10                  15

<210> SEQ ID NO 32
<211> LENGTH: 19
<212> TYPE: PRT
<213> ORGANISM: Unknown
<220> FEATURE:
<223> OTHER INFORMATION: Betulaceae

<400> SEQUENCE: 32

Ala Gly Leu Phe Lys Ala Val Glu Asn Tyr Leu Val Ala His Pro Asn
1               5                   10                  15

Ala Tyr Asn

<210> SEQ ID NO 33
<211> LENGTH: 19
<212> TYPE: PRT
<213> ORGANISM: Unknown
<220> FEATURE:
<223> OTHER INFORMATION: Betulaceae

<400> SEQUENCE: 33

Glu Thr Leu Leu Arg Ala Val Glu Arg Tyr Leu Leu Ala His Ser Asp
1               5                   10                  15

Ala Tyr Asn

<210> SEQ ID NO 34
<211> LENGTH: 19
<212> TYPE: PRT
<213> ORGANISM: Unknown
<220> FEATURE:
<223> OTHER INFORMATION: Betulaceae

<400> SEQUENCE: 34

Glu Ala Leu Phe Arg Ala Val Glu Ser Tyr Leu Leu Ala His Ser Asp
1               5                   10                  15

Ala Tyr Asn

<210> SEQ ID NO 35
<211> LENGTH: 18
<212> TYPE: PRT
<213> ORGANISM: Unknown
<220> FEATURE:
<223> OTHER INFORMATION: Betulaceae

<400> SEQUENCE: 35

Val Asp Phe Phe Glu Phe Lys Asp Met Met Arg Ser Val Leu Val Arg

```
                 1               5                  10                  15

Ser Ser

<210> SEQ ID NO 36

<400> SEQUENCE: 36

000

<210> SEQ ID NO 37
<211> LENGTH: 18
<212> TYPE: PRT
<213> ORGANISM: Unknown
<220> FEATURE:
<223> OTHER INFORMATION: Betulaceae

<400> SEQUENCE: 37

Ala Glu Arg Glu Arg Ile Phe Lys Arg Phe Asp Ala Asn Gly Asp Gly
1               5                   10                  15

Lys Ile

<210> SEQ ID NO 38
<211> LENGTH: 15
<212> TYPE: PRT
<213> ORGANISM: Unknown
<220> FEATURE:
<223> OTHER INFORMATION: Betulaceae

<400> SEQUENCE: 38

Phe Thr Asp Phe Gly Arg Ala Asn Arg Gly Leu Leu Lys Asp Val
1               5                   10                  15

<210> SEQ ID NO 39
<211> LENGTH: 15
<212> TYPE: PRT
<213> ORGANISM: Unknown
<220> FEATURE:
<223> OTHER INFORMATION: Betulaceae

<400> SEQUENCE: 39

Phe Thr Asp Phe Ala Arg Ala Asn Arg Gly Leu Leu Lys Asp Val
1               5                   10                  15

<210> SEQ ID NO 40
<211> LENGTH: 21
<212> TYPE: PRT
<213> ORGANISM: Unknown
<220> FEATURE:
<223> OTHER INFORMATION: Betulaceae

<400> SEQUENCE: 40

Pro Val Lys Gly Lys Leu Val Glu Lys Phe Lys Gly Leu Gly Val Thr
1               5                   10                  15

Leu Leu His Gly Asp
            20

<210> SEQ ID NO 41
<211> LENGTH: 24
<212> TYPE: PRT
<213> ORGANISM: Unknown
<220> FEATURE:
<223> OTHER INFORMATION: Betulaceae

<400> SEQUENCE: 41

His Glu Ser Leu Val Lys Ala Phe Lys Gln Val Asp Val Val Ile Ser
```

-continued

```
              1               5                  10                 15
Thr Val Gly His Leu Gln Leu Ala
            20

<210> SEQ ID NO 42
<211> LENGTH: 22
<212> TYPE: PRT
<213> ORGANISM: Unknown
<220> FEATURE:
<223> OTHER INFORMATION: Betulaceae

<400> SEQUENCE: 42

Tyr Val Ser Ser Asn Phe Phe Ala Gly Tyr Phe Leu Pro Thr Leu Ala
1               5                  10                 15

Gln Pro Gly Leu Thr Ser
            20

<210> SEQ ID NO 43
<211> LENGTH: 17
<212> TYPE: PRT
<213> ORGANISM: Unknown
<220> FEATURE:
<223> OTHER INFORMATION: Betulaceae

<400> SEQUENCE: 43

Pro Ile Asn Val Ile Leu Ala Ile Asn His Ser Val Phe Val Lys Gly
1               5                  10                 15

Asp

<210> SEQ ID NO 44
<211> LENGTH: 15
<212> TYPE: PRT
<213> ORGANISM: Unknown
<220> FEATURE:
<223> OTHER INFORMATION: Betulaceae

<400> SEQUENCE: 44

Ala Glu Asn Phe Arg Ala Leu Cys Thr Gly Glu Lys Gly Asn Gly
1               5                  10                 15

<210> SEQ ID NO 45
<211> LENGTH: 16
<212> TYPE: PRT
<213> ORGANISM: Unknown
<220> FEATURE:
<223> OTHER INFORMATION: Betulaceae

<400> SEQUENCE: 45

Phe Asn Tyr Glu Thr Glu Ala Thr Ser Val Ile Pro Ala Ala Arg Lys
1               5                  10                 15

<210> SEQ ID NO 46
<211> LENGTH: 16
<212> TYPE: PRT
<213> ORGANISM: Unknown
<220> FEATURE:
<223> OTHER INFORMATION: Betulaceae

<400> SEQUENCE: 46

Phe Asn Tyr Glu Ile Glu Ala Thr Ser Val Ile Pro Ala Ala Arg Lys
1               5                  10                 15

<210> SEQ ID NO 47
<211> LENGTH: 16
<212> TYPE: PRT
```

```
<213> ORGANISM: Unknown
<220> FEATURE:
<223> OTHER INFORMATION: Betulaceae

<400> SEQUENCE: 47

Phe Asn Tyr Glu Ile Glu Thr Thr Ser Val Ile Pro Ala Ala Arg Lys
1               5                   10                  15

<210> SEQ ID NO 48
<211> LENGTH: 16
<212> TYPE: PRT
<213> ORGANISM: Unknown
<220> FEATURE:
<223> OTHER INFORMATION: Betulaceae

<400> SEQUENCE: 48

Phe Asn Tyr Glu Thr Glu Thr Thr Ser Val Ile Pro Ala Ala Arg Lys
1               5                   10                  15

<210> SEQ ID NO 49
<211> LENGTH: 19
<212> TYPE: PRT
<213> ORGANISM: Unknown
<220> FEATURE:
<223> OTHER INFORMATION: Betulaceae

<400> SEQUENCE: 49

Pro Ala Ala Arg Met Phe Lys Ala Phe Ile Leu Asp Gly Asp Lys Leu
1               5                   10                  15

Val Pro Lys

<210> SEQ ID NO 50
<211> LENGTH: 19
<212> TYPE: PRT
<213> ORGANISM: Unknown
<220> FEATURE:
<223> OTHER INFORMATION: Betulaceae

<400> SEQUENCE: 50

Pro Ala Ala Arg Leu Phe Lys Ala Phe Ile Leu Glu Gly Asp Thr Leu
1               5                   10                  15

Ile Pro Lys

<210> SEQ ID NO 51
<211> LENGTH: 19
<212> TYPE: PRT
<213> ORGANISM: Unknown
<220> FEATURE:
<223> OTHER INFORMATION: Betulaceae

<400> SEQUENCE: 51

Pro Ala Ala Arg Leu Phe Lys Ala Phe Ile Leu Glu Gly Asp Asn Leu
1               5                   10                  15

Ile Pro Lys

<210> SEQ ID NO 52
<211> LENGTH: 12
<212> TYPE: PRT
<213> ORGANISM: Unknown
<220> FEATURE:
<223> OTHER INFORMATION: Betulaceae

<400> SEQUENCE: 52

Pro Ala Ala Arg Met Phe Lys Ala Phe Ile Leu Asp
1               5                   10
```

<210> SEQ ID NO 53
<211> LENGTH: 19
<212> TYPE: PRT
<213> ORGANISM: Unknown
<220> FEATURE:
<223> OTHER INFORMATION: Betulaceae

<400> SEQUENCE: 53

Pro Ala Ala Arg Met Phe Lys Ala Phe Ile Leu Glu Gly Asp Lys Leu
1               5                   10                  15

Val Pro Lys

<210> SEQ ID NO 54
<211> LENGTH: 18
<212> TYPE: PRT
<213> ORGANISM: Unknown
<220> FEATURE:
<223> OTHER INFORMATION: Betulaceae

<400> SEQUENCE: 54

Pro Gly Thr Ile Lys Lys Ile Ser Phe Pro Glu Gly Phe Pro Phe Lys
1               5                   10                  15

Tyr Val

<210> SEQ ID NO 55
<211> LENGTH: 16
<212> TYPE: PRT
<213> ORGANISM: Unknown
<220> FEATURE:
<223> OTHER INFORMATION: Betulaceae

<400> SEQUENCE: 55

Ser Pro Phe Lys Tyr Val Lys Glu Arg Val Asp Glu Val Asp His Ala
1               5                   10                  15

<210> SEQ ID NO 56
<211> LENGTH: 16
<212> TYPE: PRT
<213> ORGANISM: Unknown
<220> FEATURE:
<223> OTHER INFORMATION: Betulaceae

<400> SEQUENCE: 56

Phe Pro Phe Lys Tyr Val Lys Asp Arg Val Asp Glu Val Asp His Thr
1               5                   10                  15

<210> SEQ ID NO 57
<211> LENGTH: 17
<212> TYPE: PRT
<213> ORGANISM: Unknown
<220> FEATURE:
<223> OTHER INFORMATION: Betulaceae

<400> SEQUENCE: 57

Ala Asn Phe Lys Tyr Ser Tyr Ser Met Ile Glu Gly Gly Ala Leu Gly
1               5                   10                  15

Asp

<210> SEQ ID NO 58
<211> LENGTH: 17
<212> TYPE: PRT
<213> ORGANISM: Unknown
<220> FEATURE:
<223> OTHER INFORMATION: Betulaceae

```
<400> SEQUENCE: 58

Thr Asn Phe Lys Tyr Ser Tyr Ser Val Ile Glu Gly Gly Pro Val Gly
1               5                   10                  15

Asp

<210> SEQ ID NO 59
<211> LENGTH: 16
<212> TYPE: PRT
<213> ORGANISM: Unknown
<220> FEATURE:
<223> OTHER INFORMATION: Betulaceae

<400> SEQUENCE: 59

Thr Asn Phe Lys Tyr Asn Tyr Ser Val Ile Glu Gly Gly Pro Ile Gly
1               5                   10                  15

<210> SEQ ID NO 60
<211> LENGTH: 17
<212> TYPE: PRT
<213> ORGANISM: Unknown
<220> FEATURE:
<223> OTHER INFORMATION: Betulaceae

<400> SEQUENCE: 60

Ser Asn Glu Ile Lys Ile Val Ala Thr Pro Asp Gly Gly Ser Ile Leu
1               5                   10                  15

Lys

<210> SEQ ID NO 61
<211> LENGTH: 17
<212> TYPE: PRT
<213> ORGANISM: Unknown
<220> FEATURE:
<223> OTHER INFORMATION: Betulaceae

<400> SEQUENCE: 61

Ser Asn Glu Ile Lys Ile Val Ala Thr Pro Asn Gly Gly Ser Ile Leu
1               5                   10                  15

Lys

<210> SEQ ID NO 62
<211> LENGTH: 17
<212> TYPE: PRT
<213> ORGANISM: Unknown
<220> FEATURE:
<223> OTHER INFORMATION: Betulaceae

<400> SEQUENCE: 62

Ser Asn Glu Ile Lys Ile Val Ala Thr Pro Gln Gly Gly Ser Ile Leu
1               5                   10                  15

Lys

<210> SEQ ID NO 63
<211> LENGTH: 17
<212> TYPE: PRT
<213> ORGANISM: Unknown
<220> FEATURE:
<223> OTHER INFORMATION: Betulaceae

<400> SEQUENCE: 63

Ser Asn Glu Ile Lys Ile Val Ala Thr Pro Glu Gly Gly Ser Ile Leu
1               5                   10                  15
```

Lys

<210> SEQ ID NO 64
<211> LENGTH: 17
<212> TYPE: PRT
<213> ORGANISM: Unknown
<220> FEATURE:
<223> OTHER INFORMATION: Betulaceae

<400> SEQUENCE: 64

Ser Asn Glu Ile Lys Ile Val Ala Thr Pro Gly Gly Gly Ser Ile Leu
1               5                   10                  15

Lys

<210> SEQ ID NO 65
<211> LENGTH: 15
<212> TYPE: PRT
<213> ORGANISM: Unknown
<220> FEATURE:
<223> OTHER INFORMATION: Betulaceae

<400> SEQUENCE: 65

Gly Ser Ile Leu Lys Ile Asn Asn Lys Tyr His Thr Lys Gly Asp
1               5                   10                  15

<210> SEQ ID NO 66
<211> LENGTH: 14
<212> TYPE: PRT
<213> ORGANISM: Unknown
<220> FEATURE:
<223> OTHER INFORMATION: Betulaceae

<400> SEQUENCE: 66

Ser Ile Leu Lys Ile Ser Asn Lys Tyr His Thr Lys Gly Asp
1               5                   10

<210> SEQ ID NO 67
<211> LENGTH: 18
<212> TYPE: PRT
<213> ORGANISM: Unknown
<220> FEATURE:
<223> OTHER INFORMATION: Betulaceae

<400> SEQUENCE: 67

Glu Thr Leu Leu Arg Ala Val Glu Ser Tyr Leu Leu Ala His Ser Asp
1               5                   10                  15

Ala Tyr

<210> SEQ ID NO 68
<211> LENGTH: 16
<212> TYPE: PRT
<213> ORGANISM: Unknown
<220> FEATURE:
<223> OTHER INFORMATION: Betulaceae

<400> SEQUENCE: 68

Gly Glu Thr Leu Leu Arg Ala Val Glu Ser Tyr Leu Leu Ala His Ser
1               5                   10                  15

<210> SEQ ID NO 69
<211> LENGTH: 19
<212> TYPE: PRT
<213> ORGANISM: Unknown
<220> FEATURE:
<223> OTHER INFORMATION: Betulaceae

```
<400> SEQUENCE: 69

Lys Glu Met Gly Glu Thr Leu Leu Arg Ala Val Glu Ser Tyr Leu Leu
1               5                   10                  15

Ala His Ser

<210> SEQ ID NO 70
<211> LENGTH: 19
<212> TYPE: PRT
<213> ORGANISM: Unknown
<220> FEATURE:
<223> OTHER INFORMATION: Betulaceae

<400> SEQUENCE: 70

Lys Glu Lys Gly Glu Thr Leu Leu Arg Ala Val Glu Ser Tyr Leu Leu
1               5                   10                  15

Ala His Ser

<210> SEQ ID NO 71
<211> LENGTH: 14
<212> TYPE: PRT
<213> ORGANISM: Unknown
<220> FEATURE:
<223> OTHER INFORMATION: Betulaceae

<400> SEQUENCE: 71

Gly Ser Val Trp Ala Gln Ser Ser Ser Phe Pro Gln Phe Lys
1               5                   10

<210> SEQ ID NO 72
<211> LENGTH: 14
<212> TYPE: PRT
<213> ORGANISM: Unknown
<220> FEATURE:
<223> OTHER INFORMATION: Betulaceae

<400> SEQUENCE: 72

Phe Pro Gln Phe Lys Pro Gln Glu Ile Thr Gly Ile Met Lys
1               5                   10

<210> SEQ ID NO 73
<211> LENGTH: 17
<212> TYPE: PRT
<213> ORGANISM: Unknown
<220> FEATURE:
<223> OTHER INFORMATION: Betulaceae

<400> SEQUENCE: 73

Pro Thr Gly Met Phe Val Ala Gly Ala Lys Tyr Met Val Ile Gln Gly
1               5                   10                  15

Arg

<210> SEQ ID NO 74
<211> LENGTH: 17
<212> TYPE: PRT
<213> ORGANISM: Unknown
<220> FEATURE:
<223> OTHER INFORMATION: Betulaceae

<400> SEQUENCE: 74

Ala Lys Tyr Met Val Ile Gln Gly Glu Pro Gly Arg Val Ile Arg Gly
1               5                   10                  15

Lys
```

```
<210> SEQ ID NO 75
<211> LENGTH: 18
<212> TYPE: PRT
<213> ORGANISM: Unknown
<220> FEATURE:
<223> OTHER INFORMATION: Betulaceae

<400> SEQUENCE: 75

Gly Ile Lys Tyr Met Val Ile Gln Gly Glu Ala Gly Ala Val Ile Arg
1               5                   10                  15

Gly Lys

<210> SEQ ID NO 76
<211> LENGTH: 16
<212> TYPE: PRT
<213> ORGANISM: Unknown
<220> FEATURE:
<223> OTHER INFORMATION: Betulaceae

<400> SEQUENCE: 76

Glu Ala Gly Ala Val Ile Arg Gly Lys Lys Gly Ser Gly Gly Ile Thr
1               5                   10                  15

<210> SEQ ID NO 77
<211> LENGTH: 16
<212> TYPE: PRT
<213> ORGANISM: Unknown
<220> FEATURE:
<223> OTHER INFORMATION: Betulaceae

<400> SEQUENCE: 77

Ser Leu Asn Thr Leu Arg Leu Arg Arg Ile Phe Asp Leu Phe Asp Lys
1               5                   10                  15

<210> SEQ ID NO 78
<211> LENGTH: 17
<212> TYPE: PRT
<213> ORGANISM: Unknown
<220> FEATURE:
<223> OTHER INFORMATION: Betulaceae

<400> SEQUENCE: 78

Ala Glu Arg Glu Arg Ile Phe Lys Arg Phe Asp Ala Asn Gly Glu Gly
1               5                   10                  15

Lys

<210> SEQ ID NO 79
<211> LENGTH: 17
<212> TYPE: PRT
<213> ORGANISM: Unknown
<220> FEATURE:
<223> OTHER INFORMATION: Betulaceae

<400> SEQUENCE: 79

Ala Glu Arg Glu Arg Ile Phe Lys Arg Phe Asp Ala Gly Gly Glu Gly
1               5                   10                  15

Lys

<210> SEQ ID NO 80
<211> LENGTH: 19
<212> TYPE: PRT
<213> ORGANISM: Unknown
<220> FEATURE:
<223> OTHER INFORMATION: Betulaceae

<400> SEQUENCE: 80
```

-continued

```
Val Lys Gly Lys Leu Val Glu Lys Phe Lys Gly Leu Gly Val Thr Leu
1               5                   10                  15

Leu His Gly

<210> SEQ ID NO 81
<211> LENGTH: 15
<212> TYPE: PRT
<213> ORGANISM: Mycobacterium tuberculosis

<400> SEQUENCE: 81

Ala Lys Thr Ile Ala Tyr Asp Glu Glu Ala Arg Arg Gly Leu Glu
1               5                   10                  15

<210> SEQ ID NO 82
<211> LENGTH: 13
<212> TYPE: PRT
<213> ORGANISM: Influenza virus

<400> SEQUENCE: 82

Pro Lys Tyr Val Lys Gln Asn Thr Leu Lys Leu Ala Thr
1               5                   10

<210> SEQ ID NO 83
<211> LENGTH: 15
<212> TYPE: PRT
<213> ORGANISM: Homo sapiens

<400> SEQUENCE: 83

Glu Asn Pro Val Val His Phe Phe Lys Asn Ile Val Thr Pro Arg
1               5                   10                  15

<210> SEQ ID NO 84
<211> LENGTH: 145
<212> TYPE: PRT
<213> ORGANISM: Unknown
<220> FEATURE:
<223> OTHER INFORMATION: Oleaceae

<400> SEQUENCE: 84

Glu Asp Ile Pro Gln Pro Pro Val Ser Gln Phe His Ile Gln Gly Gln
1               5                   10                  15

Val Tyr Cys Asp Thr Cys Arg Ala Gly Phe Ile Thr Glu Leu Ser Glu
                20                  25                  30

Phe Ile Pro Gly Ala Ser Leu Arg Leu Gln Cys Lys Asp Lys Glu Asn
            35                  40                  45

Gly Asp Val Thr Phe Thr Glu Val Gly Tyr Thr Arg Ala Glu Gly Leu
        50                  55                  60

Tyr Ser Met Leu Val Glu Arg Asp His Lys Asn Glu Phe Cys Glu Ile
65                  70                  75                  80

Thr Leu Ile Ser Ser Gly Arg Lys Asp Cys Asn Glu Ile Pro Thr Glu
                85                  90                  95

Gly Trp Ala Lys Pro Ser Leu Lys Phe Lys Leu Asn Thr Val Asn Gly
            100                 105                 110

Thr Thr Arg Thr Val Asn Pro Leu Gly Phe Phe Lys Lys Glu Ala Leu
        115                 120                 125

Pro Lys Cys Ala Gln Val Tyr Asn Lys Leu Gly Met Tyr Pro Pro Asn
    130                 135                 140

Met
145
```

```
<210> SEQ ID NO 85
<211> LENGTH: 133
<212> TYPE: PRT
<213> ORGANISM: Unknown
<220> FEATURE:
<223> OTHER INFORMATION: Betulaceae

<400> SEQUENCE: 85

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ser Phe Pro Gln Phe Lys Pro Gln Glu
        35                  40                  45

Ile Thr Gly Ile Met Lys Asp Phe Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Lys Lys Gly Ser Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
            115                 120                 125

Ile Asp Gln Gly Leu
        130

<210> SEQ ID NO 86
<211> LENGTH: 133
<212> TYPE: PRT
<213> ORGANISM: Unknown
<220> FEATURE:
<223> OTHER INFORMATION: Betulaceae

<400> SEQUENCE: 86

Met Ser Trp Gln Thr Tyr Val Asp Glu His Leu Met Cys Asp Ile Asp
1               5                   10                  15

Gly Gln Gly Glu Glu Leu Ala Ala Ser Ala Ile Val Gly His Asp Gly
            20                  25                  30

Ser Val Trp Ala Gln Ser Ser Phe Pro Gln Phe Lys Pro Gln Glu
        35                  40                  45

Ile Thr Gly Ile Met Lys Asp Phe Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Lys Lys Gly Ser Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
            115                 120                 125

Ile Asp Gln Gly Leu
        130

<210> SEQ ID NO 87
<211> LENGTH: 133
<212> TYPE: PRT
<213> ORGANISM: Unknown
```

<220> FEATURE:
<223> OTHER INFORMATION: Betulaceae

<400> SEQUENCE: 87

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ser Ser Phe Pro Gln Phe Lys Pro Gln Glu
        35                  40                  45

Ile Thr Gly Ile Met Lys Asp Phe Glu Glu Pro Gly His Leu Ala Pro
50                  55                  60

Thr Gly Leu His Leu Gly Gly Ile Lys Tyr Met Val Ile Gln Gly Glu
65                  70                  75                  80

Ala Gly Ala Val Ile Arg Gly Lys Lys Gly Ser Gly Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
        115                 120                 125

Ile Asp Gln Gly Leu
    130

<210> SEQ ID NO 88
<211> LENGTH: 133
<212> TYPE: PRT
<213> ORGANISM: Unknown
<220> FEATURE:
<223> OTHER INFORMATION: Betulaceae

<400> SEQUENCE: 88

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ser Ser Phe Pro Gln Phe Lys Pro Gln Glu
        35                  40                  45

Ile Thr Gly Ile Met Lys Asp Phe Glu Glu Pro Gly His Leu Ala Pro
50                  55                  60

Thr Gly Leu His Leu Gly Gly Ile Lys Tyr Met Val Ile Gln Gly Glu
65                  70                  75                  80

Ala Gly Ala Val Ile Arg Gly Lys Lys Gly Ser Gly Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
        115                 120                 125

Ile Asp Gln Gly Leu
    130

<210> SEQ ID NO 89
<211> LENGTH: 133
<212> TYPE: PRT
<213> ORGANISM: Unknown
<220> FEATURE:
<223> OTHER INFORMATION: Betulaceae

<400> SEQUENCE: 89

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ser Phe Pro Gln Phe Lys Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Lys Lys Gly Ser Gly Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
            115                 120                 125

Ile Asp Gln Gly Leu
            130

<210> SEQ ID NO 90
<211> LENGTH: 133
<212> TYPE: PRT
<213> ORGANISM: Unknown
<220> FEATURE:
<223> OTHER INFORMATION: Betulaceae

<400> SEQUENCE: 90

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ser Phe Pro Gln Phe Lys Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Lys Lys Gly Ser Gly Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
            115                 120                 125

Ile Asp Gln Gly Leu
            130

<210> SEQ ID NO 91
<211> LENGTH: 205
<212> TYPE: PRT
<213> ORGANISM: Unknown
<220> FEATURE:
<223> OTHER INFORMATION: Betulaceae

<400> SEQUENCE: 91

Met Pro Cys Ser Thr Glu Ala Met Glu Lys Ala Gly His Gly His Ala
1               5                   10                  15

Ser Thr Pro Arg Lys Arg Ser Leu Ser Asn Ser Ser Phe Arg Leu Arg
            20                  25                  30

Ser Glu Ser Leu Asn Thr Leu Arg Leu Arg Arg Ile Phe Asp Leu Phe
        35                  40                  45

Asp Lys Asn Ser Asp Gly Ile Ile Thr Val Asp Glu Leu Ser Arg Ala
 50                  55                  60

Leu Asn Leu Leu Gly Leu Glu Thr Asp Leu Ser Glu Leu Glu Ser Thr
 65                  70                  75                  80

Val Lys Ser Phe Thr Arg Glu Gly Asn Ile Gly Leu Gln Phe Glu Asp
                85                  90                  95

Phe Ile Ser Leu His Gln Ser Leu Asn Asp Ser Tyr Phe Ala Tyr Gly
                100                 105                 110

Gly Glu Asp Glu Asp Asn Glu Asp Met Arg Lys Ser Ile Leu
            115                 120                 125

Ser Gln Glu Glu Ala Asp Ser Phe Gly Gly Phe Lys Val Phe Asp Glu
        130                 135                 140

Asp Gly Asp Gly Tyr Ile Ser Ala Arg Glu Leu Gln Met Val Leu Gly
145                 150                 155                 160

Lys Leu Gly Phe Ser Glu Gly Ser Glu Ile Asp Arg Val Glu Lys Met
                165                 170                 175

Ile Val Ser Val Asp Ser Asn Arg Asp Gly Arg Val Asp Phe Phe Glu
                180                 185                 190

Phe Lys Asp Met Met Arg Ser Val Leu Val Arg Ser Ser
        195                 200                 205

<210> SEQ ID NO 92
<211> LENGTH: 85
<212> TYPE: PRT
<213> ORGANISM: Unknown
<220> FEATURE:
<223> OTHER INFORMATION: Betulaceae

<400> SEQUENCE: 92

Met Ala Asp Asp His Pro Gln Asp Lys Ala Glu Arg Glu Arg Ile Phe
 1               5                  10                  15

Lys Arg Phe Asp Ala Asn Gly Asp Gly Lys Ile Ser Ala Ala Glu Leu
                20                  25                  30

Gly Glu Ala Leu Lys Thr Leu Gly Ser Ile Thr Pro Asp Glu Val Lys
            35                  40                  45

His Met Met Ala Glu Ile Asp Thr Asp Gly Asp Gly Phe Ile Ser Phe
 50                  55                  60

Gln Glu Phe Thr Asp Phe Gly Arg Ala Asn Arg Gly Leu Leu Lys Asp
65                  70                  75                  80

Val Ala Lys Ile Phe
                85

<210> SEQ ID NO 93
<211> LENGTH: 24
<212> TYPE: PRT
<213> ORGANISM: Quercus alba
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 93

Gly Val Phe Thr Xaa Glu Ser Gln Glu Thr Ser Val Ile Ala Pro Ala

```
                1               5                   10                  15
Xaa Leu Phe Lys Ala Leu Phe Leu
            20

<210> SEQ ID NO 94
<211> LENGTH: 40
<212> TYPE: PRT
<213> ORGANISM: Carpinus betulus
<220> FEATURE:
<221> NAME/KEY: misc_feature
<222> LOCATION: (39)..(39)
<223> OTHER INFORMATION: Xaa can be any naturally occurring amino acid

<400> SEQUENCE: 94

Gly Val Phe Asn Tyr Glu Ala Glu Thr Pro Ser Val Ile Pro Ala Ala
1               5                   10                  15

Arg Leu Phe Lys Ser Tyr Val Leu Asp Gly Asp Lys Leu Ile Pro Lys
            20                  25                  30

Val Ala Pro Gln Ala Ile Xaa Lys
        35                  40

<210> SEQ ID NO 95
<211> LENGTH: 44
<212> TYPE: PRT
<213> ORGANISM: Alnus glutinosa

<400> SEQUENCE: 95

Gly Val Phe Asn Tyr Glu Ala Glu Thr Pro Ser Val Ile Pro Ala Ala
1               5                   10                  15

Arg Leu Phe Lys Ala Phe Ile Leu Asp Gly Asp Lys Leu Leu Pro Lys
            20                  25                  30

Val Ala Pro Glu Ala Val Ser Ser Val Glu Asn Ile
        35                  40

<210> SEQ ID NO 96
<211> LENGTH: 110
<212> TYPE: PRT
<213> ORGANISM: Betula pendula
<220> FEATURE:
<221> NAME/KEY: MISC_FEATURE
<222> LOCATION: (1)..(110)
<223> OTHER INFORMATION: RuBisCO

<400> SEQUENCE: 96

Val Gln Cys Met Gln Val Trp Pro Pro Leu Gly Leu Lys Lys Phe Glu
1               5                   10                  15

Thr Leu Ser Tyr Leu Pro Pro Leu Ser Ser Glu Gln Leu Ala Lys Glu
            20                  25                  30

Val Asp Tyr Leu Leu Arg Lys Asn Leu Ile Pro Cys Leu Glu Phe Glu
        35                  40                  45

Leu Glu His Gly Phe Val Tyr Arg Glu His Asn Arg Ser Pro Gly Tyr
    50                  55                  60

Tyr Asp Gly Arg Tyr Trp Thr Met Trp Lys Leu Pro Met Phe Gly Cys
65                  70                  75                  80

Asn Asp Ser Ser Gln Val Leu Lys Glu Leu Glu Glu Cys Lys Lys Ala
            85                  90                  95

Tyr Pro Ser Ala Phe Ile Arg Ile Ile Gly Phe Asp Asp Lys
        100                 105                 110

<210> SEQ ID NO 97
<211> LENGTH: 373
```

```
<212> TYPE: PRT
<213> ORGANISM: Unknown
<220> FEATURE:
<223> OTHER INFORMATION: Pinaceae

<400> SEQUENCE: 97
```

| | | | | | | | | | | | | | | | |
|---|---|---|---|---|---|---|---|---|---|---|---|---|---|---|---|
| Met | Asp | Ser | Pro | Cys | Leu | Val | Ala | Leu | Leu | Val | Phe | Ser | Phe | Val | Ile |
| 1 | | | | 5 | | | | | 10 | | | | | 15 | |
| Gly | Ser | Cys | Phe | Ser | Asp | Asn | Pro | Ile | Asp | Ser | Cys | Trp | Arg | Gly | Asp |
| | | | 20 | | | | | 25 | | | | | 30 | | |
| Ser | Asn | Trp | Ala | Gln | Asn | Arg | Met | Lys | Leu | Ala | Asp | Cys | Ala | Val | Gly |
| | | | | 35 | | | | | 40 | | | | 45 | | |
| Phe | Gly | Ser | Ser | Thr | Met | Gly | Gly | Lys | Gly | Gly | Asp | Leu | Tyr | Thr | Val |
| 50 | | | | | | 55 | | | | | 60 | | | | |
| Thr | Asn | Ser | Asp | Asp | Pro | Val | Asn | Pro | Pro | Gly | Thr | Leu | Arg | Tyr | |
| 65 | | | | | 70 | | | | | 75 | | | | 80 | |
| Gly | Ala | Thr | Arg | Asp | Arg | Pro | Leu | Trp | Ile | Ile | Phe | Ser | Gly | Asn | Met |
| | | | | 85 | | | | | 90 | | | | | 95 | |
| Asn | Ile | Lys | Leu | Lys | Met | Pro | Met | Tyr | Ile | Ala | Gly | Tyr | Lys | Thr | Phe |
| | | | | 100 | | | | | 105 | | | | | 110 | |
| Asp | Gly | Arg | Gly | Ala | Gln | Val | Tyr | Ile | Gly | Asn | Gly | Gly | Pro | Cys | Val |
| | | | 115 | | | | | 120 | | | | | 125 | | |
| Phe | Ile | Lys | Arg | Val | Ser | Asn | Val | Ile | Ile | His | Gly | Leu | Tyr | Leu | Tyr |
| | 130 | | | | | 135 | | | | | 140 | | | | |
| Gly | Cys | Ser | Thr | Ser | Val | Leu | Gly | Asn | Val | Leu | Ile | Asn | Glu | Ser | Phe |
| 145 | | | | | 150 | | | | | 155 | | | | | 160 |
| Gly | Val | Glu | Pro | Val | His | Pro | Gln | Asp | Gly | Asp | Ala | Leu | Thr | Leu | Arg |
| | | | | 165 | | | | | 170 | | | | | 175 | |
| Thr | Ala | Thr | Asn | Ile | Trp | Ile | Asp | His | Asn | Ser | Phe | Ser | Asn | Ser | Ser |
| | | | 180 | | | | | 185 | | | | | 190 | | |
| Asp | Gly | Leu | Val | Asp | Val | Thr | Leu | Thr | Ser | Thr | Gly | Val | Thr | Ile | Ser |
| | | | 195 | | | | | 200 | | | | | 205 | | |
| Asn | Asn | Leu | Phe | Phe | Asn | His | His | Lys | Val | Met | Ser | Leu | Gly | His | Asp |
| | 210 | | | | | 215 | | | | | 220 | | | | |
| Asp | Ala | Tyr | Ser | Asp | Asp | Lys | Ser | Met | Lys | Val | Thr | Val | Ala | Phe | Asn |
| 225 | | | | | 230 | | | | | 235 | | | | | 240 |
| Gln | Phe | Gly | Pro | Asn | Cys | Gly | Gln | Arg | Met | Pro | Arg | Ala | Arg | Tyr | Gly |
| | | | | 245 | | | | | 250 | | | | | 255 | |
| Leu | Val | His | Val | Ala | Asn | Asn | Asn | Tyr | Asp | Pro | Trp | Thr | Ile | Tyr | Ala |
| | | | 260 | | | | | 265 | | | | | 270 | | |
| Ile | Gly | Gly | Ser | Ser | Asn | Pro | Thr | Ile | Leu | Ser | Glu | Gly | Asn | Ser | Phe |
| | | | 275 | | | | | 280 | | | | | 285 | | |
| Thr | Ala | Pro | Asn | Glu | Ser | Tyr | Lys | Lys | Gln | Val | Thr | Ile | Arg | Ile | Gly |
| | 290 | | | | | 295 | | | | | 300 | | | | |
| Cys | Lys | Thr | Ser | Ser | Ser | Cys | Ser | Asn | Trp | Val | Trp | Gln | Ser | Thr | Gln |
| 305 | | | | | 310 | | | | | 315 | | | | | 320 |
| Asp | Val | Phe | Tyr | Asn | Gly | Ala | Tyr | Phe | Val | Ser | Ser | Gly | Lys | Tyr | Glu |
| | | | | 325 | | | | | 330 | | | | | 335 | |
| Gly | Gly | Asn | Ile | Tyr | Thr | Lys | Lys | Glu | Ala | Phe | Asn | Val | Glu | Asn | Gly |
| | | | 340 | | | | | 345 | | | | | 350 | | |
| Asn | Ala | Thr | Pro | His | Leu | Thr | Gln | Asn | Ala | Gly | Val | Leu | Thr | Cys | Ser |
| | | | 355 | | | | | 360 | | | | | 365 | | |
| Leu | Ser | Lys | Arg | Cys | | | | | | | | | | | |
| | | | 370 | | | | | | | | | | | | |

<210> SEQ ID NO 98
<211> LENGTH: 374
<212> TYPE: PRT
<213> ORGANISM: Unknown
<220> FEATURE:
<223> OTHER INFORMATION: Pinaceae

<400> SEQUENCE: 98

```
Met Asp Ser Pro Cys Leu Val Ala Leu Leu Val Leu Ser Phe Val Ile
1               5                   10                  15

Gly Ser Cys Phe Ser Asp Asn Pro Ile Asp Ser Cys Trp Arg Gly Asp
            20                  25                  30

Ser Asn Trp Ala Gln Asn Arg Met Lys Leu Ala Asp Cys Ala Val Gly
        35                  40                  45

Phe Gly Ser Ser Thr Met Gly Gly Lys Gly Gly Asp Leu Tyr Thr Val
    50                  55                  60

Thr Asn Ser Asp Asp Asp Pro Val Asn Pro Ala Pro Gly Thr Leu Arg
65                  70                  75                  80

Tyr Gly Ala Thr Arg Asp Arg Pro Leu Trp Ile Ile Phe Ser Gly Asn
                85                  90                  95

Met Asn Ile Lys Leu Lys Met Pro Met Tyr Ile Ala Gly Tyr Lys Thr
            100                 105                 110

Phe Asp Gly Arg Gly Ala Gln Val Tyr Ile Gly Asn Gly Gly Pro Cys
        115                 120                 125

Val Phe Ile Lys Arg Val Ser Asn Val Ile Ile His Gly Leu His Leu
    130                 135                 140

Tyr Gly Cys Ser Thr Ser Val Leu Gly Asn Val Leu Ile Asn Glu Ser
145                 150                 155                 160

Phe Gly Val Glu Pro Val His Pro Gln Asp Gly Asp Ala Leu Thr Leu
                165                 170                 175

Arg Thr Ala Thr Asn Ile Trp Ile Asp His Asn Ser Phe Ser Asn Ser
            180                 185                 190

Ser Asp Gly Leu Val Asp Val Thr Leu Ser Ser Thr Gly Val Thr Ile
        195                 200                 205

Ser Asn Asn Leu Phe Phe Asn His His Lys Val Met Leu Leu Gly His
    210                 215                 220

Asp Asp Ala Tyr Ser Asp Asp Lys Ser Met Lys Val Thr Val Ala Phe
225                 230                 235                 240

Asn Gln Phe Gly Pro Asn Cys Gly Gln Arg Met Pro Arg Ala Arg Tyr
                245                 250                 255

Gly Leu Val His Val Ala Asn Asn Tyr Asp Pro Trp Thr Ile Tyr
            260                 265                 270

Ala Ile Gly Gly Ser Ser Asn Pro Thr Ile Leu Ser Glu Gly Asn Ser
        275                 280                 285

Phe Thr Ala Pro Asn Glu Ser Tyr Lys Lys Gln Val Thr Ile Arg Ile
    290                 295                 300

Gly Cys Lys Thr Ser Ser Ser Cys Ser Asn Trp Val Trp Gln Ser Thr
305                 310                 315                 320

Gln Asp Val Phe Tyr Asn Gly Ala Tyr Phe Val Ser Ser Gly Lys Tyr
                325                 330                 335

Glu Gly Gly Asn Ile Tyr Thr Lys Lys Glu Ala Phe Asn Val Glu Asn
            340                 345                 350

Gly Asn Ala Thr Pro Gln Leu Thr Lys Asn Ala Gly Val Leu Thr Cys
        355                 360                 365
```

Ser Leu Ser Lys Arg Cys
    370

<210> SEQ ID NO 99
<211> LENGTH: 514
<212> TYPE: PRT
<213> ORGANISM: Cryptomeria japonica

<400> SEQUENCE: 99

Met Ala Met Lys Leu Ile Ala Pro Met Ala Phe Leu Ala Met Gln Leu
1               5                   10                  15

Ile Ile Met Ala Ala Ala Glu Asp Gln Ser Ala Gln Ile Met Leu Asp
            20                  25                  30

Ser Val Val Glu Lys Tyr Leu Arg Ser Asn Arg Ser Leu Arg Lys Val
        35                  40                  45

Glu His Ser Arg His Asp Ala Ile Asn Ile Phe Asn Val Glu Lys Tyr
    50                  55                  60

Gly Ala Val Gly Asp Gly Lys His Asp Cys Thr Glu Ala Phe Ser Thr
65                  70                  75                  80

Ala Trp Gln Ala Ala Cys Lys Asn Pro Ser Ala Met Leu Leu Val Pro
                85                  90                  95

Gly Ser Lys Lys Phe Val Val Asn Asn Leu Phe Phe Asn Gly Pro Cys
            100                 105                 110

Gln Pro His Phe Thr Phe Lys Val Asp Gly Ile Ala Ala Tyr Gln
        115                 120                 125

Asn Pro Ala Ser Trp Lys Asn Arg Ile Trp Leu Gln Phe Ala Lys
    130                 135                 140

Leu Thr Gly Phe Thr Leu Met Gly Lys Gly Val Ile Asp Gly Gln Gly
145                 150                 155                 160

Lys Gln Trp Trp Ala Gly Gln Cys Lys Trp Val Asn Gly Arg Glu Ile
                165                 170                 175

Cys Asn Asp Arg Asp Arg Pro Thr Ala Ile Lys Phe Asp Phe Ser Thr
            180                 185                 190

Gly Leu Ile Ile Gln Gly Leu Lys Leu Met Asn Ser Pro Glu Phe His
        195                 200                 205

Leu Val Phe Gly Asn Cys Glu Gly Val Lys Ile Ile Gly Ile Ser Ile
    210                 215                 220

Thr Ala Pro Arg Asp Ser Pro Asn Thr Asp Gly Ile Asp Ile Phe Ala
225                 230                 235                 240

Ser Lys Asn Phe His Leu Gln Lys Asn Thr Ile Gly Thr Gly Asp Asp
                245                 250                 255

Cys Val Ala Ile Gly Thr Gly Ser Ser Asn Ile Val Ile Glu Asp Leu
            260                 265                 270

Ile Cys Gly Pro Gly His Gly Ile Ser Ile Gly Ser Leu Gly Arg Glu
        275                 280                 285

Asn Ser Arg Ala Glu Val Ser Tyr Val His Val Asn Gly Ala Lys Phe
    290                 295                 300

Ile Asp Thr Gln Asn Gly Leu Arg Ile Lys Thr Trp Gln Gly Gly Ser
305                 310                 315                 320

Gly Met Ala Ser His Ile Ile Tyr Glu Asn Val Glu Met Ile Asn Ser
                325                 330                 335

Glu Asn Pro Ile Leu Ile Asn Gln Phe Tyr Cys Thr Ser Ala Ser Ala
            340                 345                 350

Cys Gln Asn Gln Arg Ser Ala Val Gln Ile Gln Asp Val Thr Tyr Lys
        355                 360                 365

```
Asn Ile Arg Gly Thr Ser Ala Thr Ala Ala Ile Gln Leu Lys Cys
        370                 375                 380

Ser Asp Ser Met Pro Cys Lys Asp Ile Lys Leu Ser Asp Ile Ser Leu
385                 390                 395                 400

Lys Leu Thr Ser Gly Lys Ile Ala Ser Cys Leu Asn Asp Asn Ala Asn
                405                 410                 415

Gly Tyr Phe Ser Gly His Val Ile Pro Ala Cys Lys Asn Leu Ser Pro
                420                 425                 430

Ser Ala Lys Arg Lys Glu Ser Lys Ser His Lys His Pro Lys Thr Val
                435                 440                 445

Met Val Glu Asn Met Arg Ala Tyr Asp Lys Gly Asn Arg Thr Arg Ile
    450                 455                 460

Leu Leu Gly Ser Arg Pro Pro Asn Cys Thr Asn Lys Cys His Gly Cys
465                 470                 475                 480

Ser Pro Cys Lys Ala Lys Leu Val Ile Val His Arg Ile Met Pro Gln
                485                 490                 495

Glu Tyr Tyr Pro Gln Arg Trp Ile Cys Ser Cys His Gly Lys Ile Tyr
                500                 505                 510

His Pro

<210> SEQ ID NO 100
<211> LENGTH: 514
<212> TYPE: PRT
<213> ORGANISM: Cryptomeria japonica

<400> SEQUENCE: 100

Met Ala Met Lys Phe Ile Ala Pro Met Ala Phe Val Ala Met Gln Leu
1               5                   10                  15

Ile Ile Met Ala Ala Ala Glu Asp Gln Ser Ala Gln Ile Met Leu Asp
                20                  25                  30

Ser Asp Ile Glu Gln Tyr Leu Arg Ser Asn Arg Ser Leu Arg Lys Val
                35                  40                  45

Glu His Ser Arg His Asp Ala Ile Asn Ile Phe Asn Val Glu Lys Tyr
    50                  55                  60

Gly Ala Val Gly Asp Gly Lys His Asp Cys Thr Glu Ala Phe Ser Thr
65                  70                  75                  80

Ala Trp Gln Ala Ala Cys Lys Lys Pro Ser Ala Met Leu Leu Val Pro
                85                  90                  95

Gly Asn Lys Lys Phe Val Val Asn Asn Leu Phe Phe Asn Gly Pro Cys
                100                 105                 110

Gln Pro His Phe Thr Phe Lys Val Asp Gly Ile Ile Ala Ala Tyr Gln
                115                 120                 125

Asn Pro Ala Ser Trp Lys Asn Asn Arg Ile Trp Leu Gln Phe Ala Lys
                130                 135                 140

Leu Thr Gly Phe Thr Leu Met Gly Lys Gly Val Ile Asp Gly Gln Gly
145                 150                 155                 160

Lys Gln Trp Trp Ala Gly Gln Cys Lys Trp Val Asn Gly Arg Glu Ile
                165                 170                 175

Cys Asn Asp Arg Asp Arg Pro Thr Ala Ile Lys Phe Asp Phe Ser Thr
                180                 185                 190

Gly Leu Ile Ile Gln Gly Leu Lys Leu Met Asn Ser Pro Glu Phe His
                195                 200                 205

Leu Val Phe Gly Asn Cys Glu Gly Val Lys Ile Ile Gly Ile Ser Ile
                210                 215                 220
```

```
Thr Ala Pro Arg Asp Ser Pro Asn Thr Asp Gly Ile Asp Ile Phe Ala
225                 230                 235                 240

Ser Lys Asn Phe His Leu Gln Lys Asn Thr Ile Gly Thr Gly Asp Asp
                245                 250                 255

Cys Val Ala Ile Gly Thr Gly Ser Ser Asn Ile Val Ile Glu Asp Leu
            260                 265                 270

Ile Cys Gly Pro Gly His Gly Ile Ser Ile Gly Ser Leu Gly Arg Glu
        275                 280                 285

Asn Ser Arg Ala Glu Val Ser Tyr Val His Val Asn Gly Ala Lys Phe
    290                 295                 300

Ile Asp Thr Gln Asn Gly Leu Arg Ile Lys Thr Trp Gln Gly Gly Ser
305                 310                 315                 320

Gly Met Ala Ser His Ile Ile Tyr Glu Asn Val Glu Met Ile Asn Ser
                325                 330                 335

Glu Asn Pro Ile Leu Ile Asn Gln Phe Tyr Cys Thr Ser Ala Ser Ala
            340                 345                 350

Cys Gln Asn Gln Arg Ser Ala Val Gln Ile Gln Asp Val Thr Tyr Lys
        355                 360                 365

Asn Ile Arg Gly Thr Ser Ala Thr Ala Ala Ile Gln Leu Lys Cys
    370                 375                 380

Ser Asp Ser Met Pro Cys Lys Asp Ile Lys Leu Ser Asp Ile Ser Leu
385                 390                 395                 400

Lys Leu Thr Ser Gly Lys Ile Ala Ser Cys Leu Asn Asp Asn Ala Asn
                405                 410                 415

Gly Tyr Phe Ser Gly His Val Ile Pro Ala Cys Lys Asn Leu Ser Pro
            420                 425                 430

Ser Ala Lys Arg Lys Glu Ser Lys Ser His Lys His Pro Lys Thr Val
        435                 440                 445

Met Val Lys Asn Met Gly Ala Tyr Asp Lys Gly Asn Arg Thr Arg Ile
    450                 455                 460

Leu Leu Gly Ser Arg Pro Pro Asn Cys Thr Asn Lys Cys His Gly Cys
465                 470                 475                 480

Ser Pro Cys Lys Ala Lys Leu Val Ile Val His Arg Ile Met Pro Gln
                485                 490                 495

Glu Tyr Tyr Pro Gln Arg Trp Met Cys Ser Arg His Gly Lys Ile Tyr
            500                 505                 510

His Pro

<210> SEQ ID NO 101
<211> LENGTH: 373
<212> TYPE: PRT
<213> ORGANISM: Cryptomeria japonica

<400> SEQUENCE: 101

Met Asp Ser Pro Cys Leu Val Ala Leu Leu Val Leu Ser Phe Val Ile
1               5                   10                  15

Gly Ser Cys Phe Ser Asp Asn Pro Ile Asp Ser Cys Trp Arg Gly Asp
                20                  25                  30

Ser Asn Trp Ala Gln Asn Arg Met Lys Leu Ala Asp Cys Ala Val Gly
            35                  40                  45

Phe Gly Ser Ser Thr Met Gly Gly Lys Gly Gly Asp Leu Tyr Thr Val
        50                  55                  60

Thr Asn Ser Asp Asp Asp Pro Val Asn Pro Pro Gly Thr Leu Arg Tyr
65                  70                  75                  80
```

```
Gly Ala Thr Arg Asp Arg Pro Leu Trp Ile Ile Phe Ser Gly Asn Met
                85                  90                  95

Asn Ile Lys Leu Lys Met Pro Met Tyr Ile Ala Gly Tyr Lys Thr Phe
            100                 105                 110

Asp Gly Arg Gly Ala Gln Val Tyr Ile Gly Asn Gly Gly Pro Cys Val
        115                 120                 125

Phe Ile Lys Arg Val Ser Asn Val Ile His Gly Leu His Leu Tyr
    130                 135                 140

Gly Cys Ser Thr Ser Val Leu Gly Asn Val Leu Ile Asn Glu Ser Phe
145                 150                 155                 160

Gly Val Glu Pro Val His Pro Gln Asp Gly Asp Ala Leu Thr Leu Arg
                165                 170                 175

Thr Ala Thr Asn Ile Trp Ile Asp His Asn Ser Phe Ser Asn Ser Ser
            180                 185                 190

Asp Gly Leu Val Asp Val Thr Leu Ser Ser Thr Gly Val Thr Ile Ser
        195                 200                 205

Asn Asn Leu Phe Phe Asn His His Lys Val Met Leu Leu Gly His Asp
    210                 215                 220

Asp Ala Tyr Ser Asp Asp Lys Ser Met Lys Val Thr Val Ala Phe Asn
225                 230                 235                 240

Gln Phe Gly Pro Asn Cys Gly Gln Arg Met Pro Arg Ala Arg Tyr Gly
                245                 250                 255

Leu Val His Val Ala Asn Asn Tyr Asp Pro Trp Thr Ile Tyr Ala
            260                 265                 270

Ile Gly Gly Ser Ser Asn Pro Thr Ile Leu Ser Glu Gly Asn Ser Phe
        275                 280                 285

Thr Ala Pro Asn Glu Ser Tyr Lys Lys Gln Val Thr Ile Arg Ile Gly
    290                 295                 300

Cys Lys Thr Ser Ser Ser Cys Ser Asn Trp Val Trp Gln Ser Thr Gln
305                 310                 315                 320

Asp Val Phe Tyr Asn Gly Ala Tyr Phe Val Ser Ser Gly Lys Tyr Glu
                325                 330                 335

Gly Gly Asn Ile Tyr Thr Lys Lys Glu Ala Phe Asn Val Glu Asn Gly
            340                 345                 350

Asn Ala Thr Pro Gln Leu Thr Lys Asn Ala Gly Val Leu Thr Cys Ser
        355                 360                 365

Leu Ser Lys Arg Cys
    370

<210> SEQ ID NO 102
<211> LENGTH: 374
<212> TYPE: PRT
<213> ORGANISM: Cryptomeria japonica

<400> SEQUENCE: 102

Met Asp Ser Pro Cys Leu Val Ala Leu Leu Val Phe Ser Phe Val Ile
1               5                   10                  15

Gly Ser Cys Phe Ser Asp Asn Pro Ile Asp Ser Cys Trp Arg Gly Asp
            20                  25                  30

Ser Asn Trp Ala Gln Asn Arg Met Lys Leu Ala Asp Cys Ala Val Gly
        35                  40                  45

Phe Gly Ser Ser Thr Met Gly Gly Lys Gly Gly Asp Leu Tyr Thr Val
    50                  55                  60

Thr Asn Ser Asp Asp Asp Pro Val Asn Pro Ala Pro Gly Thr Leu Arg
```

```
                65                  70                  75                  80
Tyr Gly Ala Thr Arg Asp Arg Pro Leu Trp Ile Ile Phe Ser Gly Asn
                    85                  90                  95

Met Asn Ile Lys Leu Lys Met Pro Met Tyr Ile Ala Gly Tyr Lys Thr
                100                 105                 110

Phe Asp Gly Arg Gly Ala Gln Val Tyr Ile Gly Asn Gly Gly Pro Cys
                115                 120                 125

Val Phe Ile Lys Arg Val Ser Asn Val Ile His Gly Leu Tyr Leu
130                 135                 140

Tyr Gly Cys Ser Thr Ser Val Leu Gly Asn Val Leu Ile Asn Glu Ser
145                 150                 155                 160

Phe Gly Val Glu Pro Val His Pro Gln Asp Gly Asp Ala Leu Thr Leu
                165                 170                 175

Arg Thr Ala Thr Asn Ile Trp Ile Asp His Asn Ser Phe Ser Asn Ser
                180                 185                 190

Ser Asp Gly Leu Val Asp Val Thr Leu Thr Ser Thr Gly Val Thr Ile
                195                 200                 205

Ser Asn Asn Leu Phe Phe Asn His His Lys Val Met Ser Leu Gly His
210                 215                 220

Asp Asp Ala Tyr Ser Asp Asp Lys Ser Met Lys Val Thr Val Ala Phe
225                 230                 235                 240

Asn Gln Phe Gly Pro Asn Cys Gly Gln Arg Met Pro Arg Ala Arg Tyr
                245                 250                 255

Gly Leu Val His Val Ala Asn Asn Asn Tyr Asp Pro Trp Thr Ile Tyr
                260                 265                 270

Ala Ile Gly Gly Ser Ser Asn Pro Thr Ile Leu Ser Glu Gly Asn Ser
                275                 280                 285

Phe Thr Ala Pro Asn Glu Ser Tyr Lys Lys Gln Val Thr Ile Arg Ile
                290                 295                 300

Gly Cys Lys Thr Ser Ser Ser Cys Ser Asn Trp Val Trp Gln Ser Thr
305                 310                 315                 320

Gln Asp Val Phe Tyr Asn Gly Ala Tyr Phe Val Ser Ser Gly Lys Tyr
                325                 330                 335

Glu Gly Gly Asn Ile Tyr Thr Lys Lys Glu Ala Phe Asn Val Glu Asn
                340                 345                 350

Gly Asn Ala Thr Pro His Leu Thr Gln Asn Ala Gly Val Leu Thr Cys
                355                 360                 365

Ser Leu Ser Lys Arg Cys
    370

<210> SEQ ID NO 103
<211> LENGTH: 9
<212> TYPE: PRT
<213> ORGANISM: Unknown
<220> FEATURE:
<223> OTHER INFORMATION: Betulaceae

<400> SEQUENCE: 103

Ser Leu Asn Thr Leu Arg Leu Arg Arg
1               5

<210> SEQ ID NO 104
<211> LENGTH: 9
<212> TYPE: PRT
<213> ORGANISM: Unknown
<220> FEATURE:
<223> OTHER INFORMATION: Betulaceae
```

<400> SEQUENCE: 104

Leu Asn Thr Leu Arg Leu Arg Arg Ile
1               5

<210> SEQ ID NO 105
<211> LENGTH: 9
<212> TYPE: PRT
<213> ORGANISM: Unknown
<220> FEATURE:
<223> OTHER INFORMATION: Betulaceae

<400> SEQUENCE: 105

Asn Thr Leu Arg Leu Arg Arg Ile Phe
1               5

<210> SEQ ID NO 106
<211> LENGTH: 9
<212> TYPE: PRT
<213> ORGANISM: Unknown
<220> FEATURE:
<223> OTHER INFORMATION: Betulaceae

<400> SEQUENCE: 106

Thr Leu Arg Leu Arg Arg Ile Phe Asp
1               5

<210> SEQ ID NO 107
<211> LENGTH: 9
<212> TYPE: PRT
<213> ORGANISM: Unknown
<220> FEATURE:
<223> OTHER INFORMATION: Betulaceae

<400> SEQUENCE: 107

Leu Arg Leu Arg Arg Ile Phe Asp Leu
1               5

<210> SEQ ID NO 108
<211> LENGTH: 9
<212> TYPE: PRT
<213> ORGANISM: Unknown
<220> FEATURE:
<223> OTHER INFORMATION: Betulaceae

<400> SEQUENCE: 108

Arg Leu Arg Arg Ile Phe Asp Leu Phe
1               5

<210> SEQ ID NO 109
<211> LENGTH: 9
<212> TYPE: PRT
<213> ORGANISM: Unknown
<220> FEATURE:
<223> OTHER INFORMATION: Betulaceae

<400> SEQUENCE: 109

Leu Arg Arg Ile Phe Asp Leu Phe Asp
1               5

<210> SEQ ID NO 110
<211> LENGTH: 9
<212> TYPE: PRT
<213> ORGANISM: Unknown
<220> FEATURE:
<223> OTHER INFORMATION: Betulaceae

```
<400> SEQUENCE: 110

Arg Arg Ile Phe Asp Leu Phe Asp Lys
1               5

<210> SEQ ID NO 111
<211> LENGTH: 22
<212> TYPE: PRT
<213> ORGANISM: Unknown
<220> FEATURE:
<223> OTHER INFORMATION: Betulaceae

<400> SEQUENCE: 111

Ser Val Trp Ala Gln Ser Ser Ser Phe Pro Gln Phe Lys Pro Gln Glu
1               5                   10                  15

Ile Thr Gly Ile Met Lys
            20

<210> SEQ ID NO 112
<211> LENGTH: 9
<212> TYPE: PRT
<213> ORGANISM: Unknown
<220> FEATURE:
<223> OTHER INFORMATION: Betulaceae

<400> SEQUENCE: 112

Ser Val Trp Ala Gln Ser Ser Ser Phe
1               5

<210> SEQ ID NO 113
<211> LENGTH: 9
<212> TYPE: PRT
<213> ORGANISM: Unknown
<220> FEATURE:
<223> OTHER INFORMATION: Betulaceae

<400> SEQUENCE: 113

Val Trp Ala Gln Ser Ser Ser Phe Pro
1               5

<210> SEQ ID NO 114
<211> LENGTH: 9
<212> TYPE: PRT
<213> ORGANISM: Unknown
<220> FEATURE:
<223> OTHER INFORMATION: Betulaceae

<400> SEQUENCE: 114

Trp Ala Gln Ser Ser Ser Phe Pro Gln
1               5

<210> SEQ ID NO 115
<211> LENGTH: 9
<212> TYPE: PRT
<213> ORGANISM: Unknown
<220> FEATURE:
<223> OTHER INFORMATION: Betulaceae

<400> SEQUENCE: 115

Ala Gln Ser Ser Ser Phe Pro Gln Phe
1               5

<210> SEQ ID NO 116
<211> LENGTH: 9
<212> TYPE: PRT
<213> ORGANISM: Unknown
<220> FEATURE:
```

<223> OTHER INFORMATION: Betulaceae

<400> SEQUENCE: 116

Gln Ser Ser Ser Phe Pro Gln Phe Lys
1               5

<210> SEQ ID NO 117
<211> LENGTH: 9
<212> TYPE: PRT
<213> ORGANISM: Unknown
<220> FEATURE:
<223> OTHER INFORMATION: Betulaceae

<400> SEQUENCE: 117

Ser Ser Ser Phe Pro Gln Phe Lys Pro
1               5

<210> SEQ ID NO 118
<211> LENGTH: 9
<212> TYPE: PRT
<213> ORGANISM: Unknown
<220> FEATURE:
<223> OTHER INFORMATION: Betulaceae

<400> SEQUENCE: 118

Ser Ser Phe Pro Gln Phe Lys Pro Gln
1               5

<210> SEQ ID NO 119
<211> LENGTH: 9
<212> TYPE: PRT
<213> ORGANISM: Unknown
<220> FEATURE:
<223> OTHER INFORMATION: Betulaceae

<400> SEQUENCE: 119

Ser Phe Pro Gln Phe Lys Pro Gln Glu
1               5

<210> SEQ ID NO 120
<211> LENGTH: 9
<212> TYPE: PRT
<213> ORGANISM: Unknown
<220> FEATURE:
<223> OTHER INFORMATION: Betulaceae

<400> SEQUENCE: 120

Phe Pro Gln Phe Lys Pro Gln Glu Ile
1               5

<210> SEQ ID NO 121
<211> LENGTH: 9
<212> TYPE: PRT
<213> ORGANISM: Unknown
<220> FEATURE:
<223> OTHER INFORMATION: Betulaceae

<400> SEQUENCE: 121

Pro Gln Phe Lys Pro Gln Glu Ile Thr
1               5

<210> SEQ ID NO 122
<211> LENGTH: 9
<212> TYPE: PRT
<213> ORGANISM: Unknown
<220> FEATURE:
<223> OTHER INFORMATION: Betulaceae

```
<400> SEQUENCE: 122

Gln Phe Lys Pro Gln Glu Ile Thr Gly
1               5

<210> SEQ ID NO 123
<211> LENGTH: 9
<212> TYPE: PRT
<213> ORGANISM: Unknown
<220> FEATURE:
<223> OTHER INFORMATION: Betulaceae

<400> SEQUENCE: 123

Phe Lys Pro Gln Glu Ile Thr Gly Ile
1               5

<210> SEQ ID NO 124
<211> LENGTH: 9
<212> TYPE: PRT
<213> ORGANISM: Unknown
<220> FEATURE:
<223> OTHER INFORMATION: Betulaceae

<400> SEQUENCE: 124

Lys Pro Gln Glu Ile Thr Gly Ile Met
1               5

<210> SEQ ID NO 125
<211> LENGTH: 9
<212> TYPE: PRT
<213> ORGANISM: Unknown
<220> FEATURE:
<223> OTHER INFORMATION: Betulaceae

<400> SEQUENCE: 125

Pro Gln Glu Ile Thr Gly Ile Met Lys
1               5

<210> SEQ ID NO 126
<211> LENGTH: 22
<212> TYPE: PRT
<213> ORGANISM: Unknown
<220> FEATURE:
<223> OTHER INFORMATION: Betulaceae

<400> SEQUENCE: 126

Ile Lys Tyr Met Val Ile Gln Gly Glu Ala Gly Ala Val Ile Arg Gly
1               5                   10                  15

Lys Lys Gly Ser Gly Gly
            20

<210> SEQ ID NO 127
<211> LENGTH: 9
<212> TYPE: PRT
<213> ORGANISM: Unknown
<220> FEATURE:
<223> OTHER INFORMATION: Betulaceae

<400> SEQUENCE: 127

Ile Lys Tyr Met Val Ile Gln Gly Glu
1               5

<210> SEQ ID NO 128
<211> LENGTH: 9
<212> TYPE: PRT
<213> ORGANISM: Unknown
```

```
<220> FEATURE:
<223> OTHER INFORMATION: Betulaceae

<400> SEQUENCE: 128

Lys Tyr Met Val Ile Gln Gly Glu Ala
1               5

<210> SEQ ID NO 129
<211> LENGTH: 9
<212> TYPE: PRT
<213> ORGANISM: Unknown
<220> FEATURE:
<223> OTHER INFORMATION: Betulaceae

<400> SEQUENCE: 129

Tyr Met Val Ile Gln Gly Glu Ala Gly
1               5

<210> SEQ ID NO 130
<211> LENGTH: 9
<212> TYPE: PRT
<213> ORGANISM: Unknown
<220> FEATURE:
<223> OTHER INFORMATION: Betulaceae

<400> SEQUENCE: 130

Met Val Ile Gln Gly Glu Ala Gly Ala
1               5

<210> SEQ ID NO 131
<211> LENGTH: 9
<212> TYPE: PRT
<213> ORGANISM: Unknown
<220> FEATURE:
<223> OTHER INFORMATION: Betulaceae

<400> SEQUENCE: 131

Val Ile Gln Gly Glu Ala Gly Ala Val
1               5

<210> SEQ ID NO 132
<211> LENGTH: 9
<212> TYPE: PRT
<213> ORGANISM: Unknown
<220> FEATURE:
<223> OTHER INFORMATION: Betulaceae

<400> SEQUENCE: 132

Ile Gln Gly Glu Ala Gly Ala Val Ile
1               5

<210> SEQ ID NO 133
<211> LENGTH: 9
<212> TYPE: PRT
<213> ORGANISM: Unknown
<220> FEATURE:
<223> OTHER INFORMATION: Betulaceae

<400> SEQUENCE: 133

Gln Gly Glu Ala Gly Ala Val Ile Arg
1               5

<210> SEQ ID NO 134
<211> LENGTH: 9
<212> TYPE: PRT
<213> ORGANISM: Unknown
<220> FEATURE:
```

<223> OTHER INFORMATION: Betulaceae

<400> SEQUENCE: 134

Gly Glu Ala Gly Ala Val Ile Arg Gly
1               5

<210> SEQ ID NO 135
<211> LENGTH: 9
<212> TYPE: PRT
<213> ORGANISM: Unknown
<220> FEATURE:
<223> OTHER INFORMATION: Betulaceae

<400> SEQUENCE: 135

Glu Ala Gly Ala Val Ile Arg Gly Lys
1               5

<210> SEQ ID NO 136
<211> LENGTH: 9
<212> TYPE: PRT
<213> ORGANISM: Unknown
<220> FEATURE:
<223> OTHER INFORMATION: Betulaceae

<400> SEQUENCE: 136

Ala Gly Ala Val Ile Arg Gly Lys Lys
1               5

<210> SEQ ID NO 137
<211> LENGTH: 9
<212> TYPE: PRT
<213> ORGANISM: Unknown
<220> FEATURE:
<223> OTHER INFORMATION: Betulaceae

<400> SEQUENCE: 137

Gly Ala Val Ile Arg Gly Lys Lys Gly
1               5

<210> SEQ ID NO 138
<211> LENGTH: 9
<212> TYPE: PRT
<213> ORGANISM: Unknown
<220> FEATURE:
<223> OTHER INFORMATION: Betulaceae

<400> SEQUENCE: 138

Ala Val Ile Arg Gly Lys Lys Gly Ser
1               5

<210> SEQ ID NO 139
<211> LENGTH: 9
<212> TYPE: PRT
<213> ORGANISM: Unknown
<220> FEATURE:
<223> OTHER INFORMATION: Betulaceae

<400> SEQUENCE: 139

Val Ile Arg Gly Lys Lys Gly Ser Gly
1               5

<210> SEQ ID NO 140
<211> LENGTH: 9
<212> TYPE: PRT
<213> ORGANISM: Unknown
<220> FEATURE:
<223> OTHER INFORMATION: Betulaceae

```
<400> SEQUENCE: 140

Ile Arg Gly Lys Lys Gly Ser Gly Gly
1               5

<210> SEQ ID NO 141
<211> LENGTH: 28
<212> TYPE: PRT
<213> ORGANISM: Unknown
<220> FEATURE:
<223> OTHER INFORMATION: Betulaceae

<400> SEQUENCE: 141

Phe Asn Tyr Glu Thr Glu Thr Thr Ser Val Ile Pro Ala Ala Arg Leu
1               5                   10                  15

Phe Lys Ala Phe Ile Leu Asp Gly Asp Asn Leu Phe
            20                  25

<210> SEQ ID NO 142
<211> LENGTH: 9
<212> TYPE: PRT
<213> ORGANISM: Unknown
<220> FEATURE:
<223> OTHER INFORMATION: Betulaceae

<400> SEQUENCE: 142

Phe Asn Tyr Glu Thr Glu Thr Thr Ser
1               5

<210> SEQ ID NO 143
<211> LENGTH: 9
<212> TYPE: PRT
<213> ORGANISM: Unknown
<220> FEATURE:
<223> OTHER INFORMATION: Betulaceae

<400> SEQUENCE: 143

Asn Tyr Glu Thr Glu Thr Thr Ser Val
1               5

<210> SEQ ID NO 144
<211> LENGTH: 9
<212> TYPE: PRT
<213> ORGANISM: Unknown
<220> FEATURE:
<223> OTHER INFORMATION: Betulaceae

<400> SEQUENCE: 144

Tyr Glu Thr Glu Thr Thr Ser Val Ile
1               5

<210> SEQ ID NO 145
<211> LENGTH: 9
<212> TYPE: PRT
<213> ORGANISM: Unknown
<220> FEATURE:
<223> OTHER INFORMATION: Betulaceae

<400> SEQUENCE: 145

Glu Thr Glu Thr Thr Ser Val Ile Pro
1               5

<210> SEQ ID NO 146
<211> LENGTH: 9
<212> TYPE: PRT
<213> ORGANISM: Unknown
```

```
<220> FEATURE:
<223> OTHER INFORMATION: Betulaceae

<400> SEQUENCE: 146

Thr Glu Thr Thr Ser Val Ile Pro Ala
1               5

<210> SEQ ID NO 147
<211> LENGTH: 9
<212> TYPE: PRT
<213> ORGANISM: Unknown
<220> FEATURE:
<223> OTHER INFORMATION: Betulaceae

<400> SEQUENCE: 147

Glu Thr Thr Ser Val Ile Pro Ala Ala
1               5

<210> SEQ ID NO 148
<211> LENGTH: 9
<212> TYPE: PRT
<213> ORGANISM: Unknown
<220> FEATURE:
<223> OTHER INFORMATION: Betulaceae

<400> SEQUENCE: 148

Thr Thr Ser Val Ile Pro Ala Ala Arg
1               5

<210> SEQ ID NO 149
<211> LENGTH: 9
<212> TYPE: PRT
<213> ORGANISM: Unknown
<220> FEATURE:
<223> OTHER INFORMATION: Betulaceae

<400> SEQUENCE: 149

Thr Ser Val Ile Pro Ala Ala Arg Leu
1               5

<210> SEQ ID NO 150
<211> LENGTH: 9
<212> TYPE: PRT
<213> ORGANISM: Unknown
<220> FEATURE:
<223> OTHER INFORMATION: Betulaceae

<400> SEQUENCE: 150

Ser Val Ile Pro Ala Ala Arg Leu Phe
1               5

<210> SEQ ID NO 151
<211> LENGTH: 9
<212> TYPE: PRT
<213> ORGANISM: Unknown
<220> FEATURE:
<223> OTHER INFORMATION: Betulaceae

<400> SEQUENCE: 151

Val Ile Pro Ala Ala Arg Leu Phe Lys
1               5

<210> SEQ ID NO 152
<211> LENGTH: 9
<212> TYPE: PRT
<213> ORGANISM: Unknown
<220> FEATURE:
```

<223> OTHER INFORMATION: Betulaceae

<400> SEQUENCE: 152

Ile Pro Ala Ala Arg Leu Phe Lys Ala
1               5

<210> SEQ ID NO 153
<211> LENGTH: 9
<212> TYPE: PRT
<213> ORGANISM: Unknown
<220> FEATURE:
<223> OTHER INFORMATION: Betulaceae

<400> SEQUENCE: 153

Pro Ala Ala Arg Leu Phe Lys Ala Phe
1               5

<210> SEQ ID NO 154
<211> LENGTH: 9
<212> TYPE: PRT
<213> ORGANISM: Unknown
<220> FEATURE:
<223> OTHER INFORMATION: Betulaceae

<400> SEQUENCE: 154

Ala Ala Arg Leu Phe Lys Ala Phe Ile
1               5

<210> SEQ ID NO 155
<211> LENGTH: 9
<212> TYPE: PRT
<213> ORGANISM: Unknown
<220> FEATURE:
<223> OTHER INFORMATION: Betulaceae

<400> SEQUENCE: 155

Ala Arg Leu Phe Lys Ala Phe Ile Leu
1               5

<210> SEQ ID NO 156
<211> LENGTH: 9
<212> TYPE: PRT
<213> ORGANISM: Unknown
<220> FEATURE:
<223> OTHER INFORMATION: Betulaceae

<400> SEQUENCE: 156

Arg Leu Phe Lys Ala Phe Ile Leu Asp
1               5

<210> SEQ ID NO 157
<211> LENGTH: 9
<212> TYPE: PRT
<213> ORGANISM: Unknown
<220> FEATURE:
<223> OTHER INFORMATION: Betulaceae

<400> SEQUENCE: 157

Leu Phe Lys Ala Phe Ile Leu Asp Gly
1               5

<210> SEQ ID NO 158
<211> LENGTH: 9
<212> TYPE: PRT
<213> ORGANISM: Unknown
<220> FEATURE:
<223> OTHER INFORMATION: Betulaceae

```
<400> SEQUENCE: 158

Phe Lys Ala Phe Ile Leu Asp Gly Asp
1               5

<210> SEQ ID NO 159
<211> LENGTH: 9
<212> TYPE: PRT
<213> ORGANISM: Unknown
<220> FEATURE:
<223> OTHER INFORMATION: Betulaceae

<400> SEQUENCE: 159

Lys Ala Phe Ile Leu Asp Gly Asp Asn
1               5

<210> SEQ ID NO 160
<211> LENGTH: 9
<212> TYPE: PRT
<213> ORGANISM: Unknown
<220> FEATURE:
<223> OTHER INFORMATION: Betulaceae

<400> SEQUENCE: 160

Ala Phe Ile Leu Asp Gly Asp Asn Leu
1               5

<210> SEQ ID NO 161
<211> LENGTH: 9
<212> TYPE: PRT
<213> ORGANISM: Unknown
<220> FEATURE:
<223> OTHER INFORMATION: Betulaceae

<400> SEQUENCE: 161

Phe Ile Leu Asp Gly Asp Asn Leu Phe
1               5
```

PEPTIDES FOR VACCINE AGAINST BIRCH ALLERGY

CROSS-REFERENCE TO RELATED APPLICATIONS

This application is the U.S. national stage filing under 35 U.S.C. §371 of international application PCT/GB2011/000206, filed Feb. 15, 2011, which claims benefit of Great Britain Application No. 1002559.1, filed Feb. 15, 2010.

FIELD OF THE INVENTION

The present invention relates to compositions for preventing or treating allergy to birch.

BACKGROUND OF THE INVENTION

T-cell antigen recognition requires antigen presenting cells (APCs) to present antigen fragments (peptides) on their cell surface in association with molecules of the major histocompatibility complex (MHC). T cells use their antigen specific T-cell receptors (TCRs) to recognise the antigen fragments presented by the APC. Such recognition acts as a trigger to the immune system to generate a range of responses to eradicate the antigen which has been recognised.

Recognition of external antigens by the immune system of an organism, such as man, can in some cases result in diseases, known as atopic conditions. Examples of the latter are the allergic diseases including asthma, atopic dermatitis and allergic rhinitis. In this group of diseases, B lymphocytes generate antibodies of the IgE class (in humans) which bind externally derived antigens, which are referred to in this context as allergens since these molecules elicit an allergic response. Production of allergen-specific IgE is dependent upon T lymphocytes which are also activated by (are specific for) the allergen. Allergen-specific IgE antibodies bind to the surface of cells such as basophils and mast cells by virtue of the expression by these cells of surface receptors for IgE.

Crosslinking of surface bound IgE molecules by allergen results in degranulation of these effector cells causing release of inflammatory mediators such as histamine, 5-hydroxtryptamine and lipid mediators such as the sulphidoleukotrienes. In addition to IgE-dependent events, certain allergic diseases such as asthma are characterised by IgE-independent events.

Allergic IgE-mediated diseases are currently treated with agents which provide symptomatic relief or prevention. Examples of such agents are anti-histamines, β2 agonists, and glucocorticosteroids. In addition, some IgE-mediated diseases are treated by desensitisation procedures that involve the periodic injection of allergen components or extracts. Desensitisation treatments may induce an IgG response that competes with IgE for allergen, or they may induce specific suppressor T cells that block the synthesis of IgE directed against allergen. This form of treatment is not always effective and poses the risk of provoking serious side effects, particularly general anaphylactic shock. This can be fatal unless recognised immediately and treated with adrenaline. A therapeutic treatment that would decrease or eliminate the unwanted allergic-immune response to a particular allergen, without altering the immune reactivity to other foreign antigens or triggering an allergic response itself would be of great benefit to allergic individuals.

Pollen allergens are recognised as a major cause of allergic diseases in humans and animals, including asthma, allergic rhinitis and allergic dermatitis. At least 10% of the population of the USA suffers from pollen allergies at various times and to varying extents. Proteins present in tree pollen, in particular from trees of the order Fagales, for example birch, alder, hazel, hornbeam and oak, are particularly important. Of these species, birch pollen allergens are the most frequent initiators of allergic responses to tree pollen (Jarolim et al: Allergy 1989; 44(6):385-95). For example, approximately 25% of hayfever sufferers are responsive to birch pollen. Hayfever is the common term for a form of seasonal allergy characterised by sneezing, runny nose and itching eyes. Allergy to tree pollen is most problematic during the spring months, with the birch pollen season typically occurring around April (in the northern hemisphere). However, some related types of tree such as alder and hazel can release airborne pollen as early as January (northern hemisphere). These are followed by elm, willow and ash in March, with oak in late April and early May.

It has been calculated that for adults in the United States, hayfever is the 5th leading chronic disease and a major cause of work absenteeism, resulting in nearly 4 million missed or lost workdays each year, resulting in a total cost of more than $700 million in total lost productivity. Allergies are also the most frequently reported chronic condition in children, limiting activities for more than 40% of them. Each year, allergies account for more than 17 million outpatient office visits in the United States; seasonal allergies such as hayfever account for more than half of these allergy visits.

A therapeutic or preventative treatment would therefore be of great benefit to humans that suffer or are at risk of suffering from tree allergy.

SUMMARY OF THE INVENTION

The present inventors have discovered that certain peptide fragments derived from the major allergens in the pollens of birch species are useful in desensitising individuals to these allergens. Peptide fragments derived from Bet v2, Bet v1, Bet v3, Bet v4, Bet v6 and Bet v7 of birch (family name: Betulaceae) are particularly useful.

The peptides of the invention were selected as MHC class II-binding T cell epitopes through use of in silico analysis to predict peptide-MHC interactions and MHC class II binding assays. Additional epitopes were identified by homology.

A difficulty associated with approaches to desensitisation based on peptide immunisation lies in how to select an appropriate size and region of the allergen as the basis for the peptide to be used for immunisation. The size of the peptide of choice is crucial. If the peptide is too small, the vaccine would not be effective in inducing an immunological response. If the peptides are too large, or if the whole antigen is introduced into an individual, there is the risk of inducing adverse reactions, such as anaphylaxis, which may be fatal.

The polypeptides of the invention have been selected to retain T cell specificity whilst being small enough in size to not possess significant tertiary structure that would enable them to retain the conformation of an IgE-binding epitope of the whole molecule. The polypeptides of the invention therefore do not induce significant crosslinking of adjacent specific IgE molecules on cells such as mast cells and basophils and consequently do not cause significant histamine release.

An advantage of the invention is the ability of the peptides to broadly target Major Histocompatibility Complex (MHC) molecules. T cell receptors (TCRs) are highly variable in their specificity. Variability is generated, as with antibody molecules, through gene recombination events within the cell. TCRs recognise antigen in the form of short peptides bound to molecules encoded by the genes of the Major Histocompatibility Complex (MHC). These gene products are the same molecules that give rise to "tissue types" used in transplantation and are also referred to as Human Leukocyte Antigen molecules (HLAs) which terms may be used interchangeably. Individual MHC molecules possess peptide binding grooves which, due to their shape and charge are only capable of binding a limited group of peptides. The peptides bound by one MHC molecule may not necessarily be bound by other MHC molecules.

When a protein molecule such as an antigen or allergen is taken up by antigen presenting cells such as B lymphocytes, dendritic cells, monocytes and macrophages, the molecule is enzymatically degraded within the cell. The process of degradation gives rise to peptide fragments of the molecule which, if they are of the appropriate size, charge and shape, may then bind within the peptide binding groove of certain MHC molecules and be subsequently displayed upon the surface of antigen presenting cells. If the peptide/MHC complexes are present upon the antigen presenting cell surface in sufficient numbers they may then activate T cells which bear the appropriate peptide/MHC-specific T cell receptors.

Due to the polymorphic nature of the MHC, individuals in an outbred population such as man will express different combinations of MHC molecules on their cell surfaces. Since different MHC molecules can bind different peptides from the same molecule based on the size, charge and shape of the peptide, different individuals will display a different repertoire of peptides bound to their MHC molecules. Identification of universal MHC-binding peptide epitopes in an outbred population such as man is more difficult than in inbred animals (such as certain strains of laboratory mice). On the basis of differential MHC expression between individuals and the inherent differences in peptide binding and presentation which this brings, it is unlikely that a single peptide can be identified which will be of use for desensitisation therapy in man.

The peptides of the invention, however, provide a broad coverage of efficacy over the human population by targeting multiple different MHC molecules. A vaccine formulated with a peptide of the invention would therefore have broad utility. Accordingly, the present invention provides a composition suitable for use in preventing or treating allergy to birch pollen by tolerisation comprising:
i) at least one of the polypeptides of SEQ ID NO: 74 (BIR12B; AKYMVIQGEPGRVIRGK), SEQ ID NO: 72 (BIR11; FPQFKPQEITGIMK), SEQ ID NO: 71 (BIR10; GSVWAQSSSFPQFK), SEQ ID NO: 73 (BIR12A; PTGMFVAGAKYMVIQGR), SEQ ID NO: 75 (BIR13; IKYMVIQGEAGAVIRGK and SEQ ID NO: 76 (BIR14; EAGAVIRGKKGSGGIT), or a variant of any thereof, and
ii) at least one of the polypeptides of SEQ ID NO: 53 (Bir02J; PAARMFKAFILEGDKLVPK), SEQ ID NO: 48 (Bir01I; FNYETETTSVIPAARK), SEQ ID NO: 54 (Bir04; PGTIKKISFPEGFPFKYV), SEQ ID NO: 67 (Bir09; ETLLRAVESYLLAHSDAY), SEQ ID NO: 60 (BLR07; SNEIKIVATPDGGSILK), and SEQ ID NO: 63 (Bir07C; SNEIKIVATPEGGSTLK), or a variant of any thereof, wherein said variant is:
I) a longer polypeptide of up to 30 amino acids in length which comprises the sequence of the corresponding polypeptide specified in (i) or (ii), or
II) a polypeptide of 9 to 30 amino acids in length which comprises a sequence that has at least 65% homology to the sequence of the corresponding polypeptide specified in (i) or (ii), which sequence is capable of tolerising to said corresponding polypeptide; or
III) a polypeptide of length 9 to 30 amino acids which comprises a sequence of, or a sequence that has at least 65% homology to, at least 9 contiguous amino acids of the sequence of the corresponding polypeptide specified in (i) or (ii), which sequence of at least 9 contiguous amino acids or homologous sequence is capable of tolerising to said corresponding polypeptide.

Also provided is a composition suitable for use in preventing or treating allergy to birch pollen by tolerisation comprising at least three different polypeptides, selected from:
(a) SEQ ID NO: 74 (Bir12B; AKYMVIQGEPGRVIRGK), or a variant thereof;
(b) SEQ ID NO: 53 (Bir02J; PAARMFKAFILEGDKLVPK), or a variant thereof;
(c) SEQ ID NO: 48 (Bir01I; FNYETETTSVIPAARK) or a variant thereof;
(d) SEQ ID NO: 54 (Bir04; PGTIKKISFPEGFPFKYV) or a variant thereof;
(e) SEQ ID NO: 67 (Bir09; ETLLRAVESYLLAHSDAY) or a variant thereof;
(f) SEQ ID NO: 78 (Bir16A ; AERERIFKRFDANGEGK) or a variant thereof;
(g) SEQ ID NO: 60 (Bir07; SNEIKIVATPDGGSILK) or a variant thereof;
(h) SEQ ID NO: 63 (Bir07C; SNEIKIVATPEGGSILK) or a variant thereof;
(i) SEQ ID NO: 72 (Bir011; FPQFKPQEITGIMK) or a variant thereof;
(j) SEQ ID NO: 77 (Bir15; SLNTLRLRRIFDLFDK) or a variant thereof;
wherein said variant is:
I) a longer polypeptide of up to 30 amino acids in length which comprises the sequence of the corresponding polypeptide specified in (a) to (j), or
II) a polypeptide of 9 to 30 amino acids in length which comprises a sequence that has at least 65% homology to the sequence of the corresponding polypeptide specified in (a) to (j), which sequence is capable of tolerising to said corresponding polypeptide; or
III) a polypeptide of length 9 to 30 amino acids which comprises a sequence of, or a sequence that has at least 65% homology to, at least 9 contiguous amino acids of the sequence of the corresponding polypeptide specified in (a) to (j), which sequence of at least 9 contiguous amino acids or homologous sequence is capable of tolerising to said corresponding polypeptide.

DESCRIPTION OF THE SEQUENCES MENTIONED HEREIN

SEQ ID NOS: 1 to 80 provide the polypeptide sequences of the invention as set out in Tables 1 to 8. SEQ ID NOS: 1 to 34 and 45 to 70 correspond to peptides derived from Bet v1. SEQ ID NOS: 71 to 76 correspond to peptides derived from Bet v2. SEQ ID NOS: 35, 36 and 77 correspond to peptides derived from Bet v3. SEQ ID NOS: 37 to 39, 78 and 79 correspond to peptides derived from Bet v4. SEQ ID NOS: 40 to 43 and 80 correspond to peptides derived from Bet v6. SEQ ID NO: 44 corresponds to a peptide derived from Bet v7.

DETAILED DESCRIPTION OF THE INVENTION

The invention concerns peptides which can be used in tolerisation. Such peptides may comprise, consist of, or consist essentially of the sequences shown in any of SEQ ID NOS: 1 to 80. Variants of these specific peptides may also be used. The variants may comprise, consist of, or consist essentially of sequences which are fragments of either any of SEQ ID NOS: 1 to 80 or homologues of any of SEQ ID NOS: 1 to 80.

The invention also provides products and formulations comprising the polypeptides of the invention and compositions, products and vectors comprising polynucleotides capable of expressing the polypeptides of the invention for use in preventing or treating birch allergy by tolerisation. Such tolerisation will typically be to an epitope (for example a MHC class II-binding T cell epitope) present in any of SEQ ID NOS: 1 to 80.

Tree Species

Species of tree from the family Betulaceae, commonly known as birch, are responsible for a high proportion of tree allergy worldwide, particularly allergies associated with tree pollen, such as hayfever. Other important tree species include alder, hazel, hornbeam and oak.

Birch trees, for example Silver Birch (*Betula pendula*), tolerate a wide range of habitats, with soil pH from approximately 3.5 to approximately 7. They are native to most of Europe and parts of Asia, but are common throughout the world, being found in the temperate, boreal, and arctic zones of the Northern Hemisphere, especially in Canada and other parts of North America. Birch trees typically flower between April and May (Northern Hemisphere).

Peptide Fragments of Birch Pollen Allergens

The present inventors have identified the regions in certain birch pollen allergen proteins which comprise MHC Class II-binding T cell epitopes. The present inventors have also shown that regions corresponding to MHC Class II-binding T cell epitopes within the major birch pollen allergens are highly conserved between different isoforms of said allergens. Based on this information, peptides derived from the relevant regions of each protein are suitable for preventing or treating birch allergy by tolerisation to all isoforms of that protein.

The peptides of the invention are derived directly or by homology from the protein allergens Bet v2 (SEQ ID NOS: 71 to 76), Bet v1 (SEQ ID NOS: 1 to 34 and 45 to 70), Bet v3 (SEQ ID NOS: 35, 36 and 77), Bet v4 (SEQ ID NOS: 37 to 39, 78 and 79), Bet v6 (SEQ ID NOS: 40 to 43 and 80) and Bet v7 (SEQ ID NO: 44). The terms "peptide" and "polypeptide" are used interchangeably herein. The above proteins are also referred to herein as "the allergens". Tables 1 to 7 set out the sequences of the peptides of the invention (SEQ ID NOS: 1 to 80), indicating the parent protein from which each peptide derives. The composition of the invention comprises at least one polypeptide selected from SEQ ID NOS: 1 to 80 or a variant of any thereof.

In other words, the invention provides a composition for use in the prevention or treatment of birch allergy by tolerisation comprising at least three, preferably at least four different polypeptides selected from any of SEQ ID NOS: 1 to 80, or a variant of any thereof. It is preferred that none of the selected polypeptides are variants of the same original sequence defined by any one of SEQ ID NOS: 1 to 80. In other words, it is preferred that each of the three or four polypeptides are different original baseline sequences defined by any one of SEQ ID NOS: 1 to 80, or are variants of different original baseline sequences defined by any one of SEQ ID NOS: 1 to 80.

Preferably, the composition will comprise polypeptides which derive from more than one allergen. For example, the composition may comprise one or more polypeptides or variants thereof derived from Bet v 2 and one or more polypeptides or variants thereof derived from Bet v 1. Additional polypeptides may optionally be included which derive from Bet v 3, Bet v 4, Bet v 6 and/or Bet v 7. Accordingly, in some embodiments, the composition comprises i) at least one of the polypeptides of SEQ ID NO: 74, 72, 71, 73, 75 and 76 (which are derived from Bet v 2), or a variant of any thereof as defined herein; and ii) at least one of the polypeptides of SEQ ID NOS: 1 to 34 and 45 to 70 (which are derived from Bet v 1), or a variant of any thereof; and optionally iii) at least one of the polypeptides of:
(a) SEQ ID NOs: 35, 36 and 77 (which are derived from Bet v 3), or a variant of any thereof as defined herein; and/or
(b) SEQ ID NOs: 37 to 39, 78 and 79 (which derived from Bet v 4), or a variant of any thereof as defined herein; and/or
(c) SEQ ID NO:s 40 to 43 and 80 (which are derived from Bet v 6), or a variant of any thereof as defined herein; and/or
(d) SEQ ID NO: 44 (which is derived from Bet v 7), or a variant thereof as defined herein.

The composition may thus comprise any combination of one or more polypeptides selected from group (i), one or more polypeptides selected from group (ii) and optionally one or more polypeptides from group (iii) (a) to (d) as defined above. Groups (i), (ii) and (iii) (a) to (d) correspond to peptides derived from different Bet allergens, as described above. Combining polypeptides derived from different Bet allergens may allow for broad coverage of birch pollen allergy observed in the general population by providing tolerising epitopes from more than one birch pollen allergen.

Non-limiting examples of compositions selected as defined above include: One, two or more polypeptides selected from SEQ ID NO: 74, 72, 71, 73, 75 and 76 or variants of any thereof, at least one polypeptide selected from group (ii) or variant of any thereof, and optionally at least one polypeptide or variant thereof selected from groups (iii) (a) and/or (b); or One, two or more polypeptides selected from SEQ ID NO: 74, 72, 71, 73, 75 and 76 or variants of any thereof and two, three, four or five polypeptides selected from group (ii) or variants of any thereof, and optionally at least one polypeptide or variant thereof selected from groups (iii) (a) and/or (b); or One, two or more polypeptides selected from SEQ ID NO: 74, 72, 71, 73, 75 and 76 or variants of any thereof and two, three, four or five polypeptides selected from group (ii) or variants of any thereof, and at least one polypeptide from group (iii) b).

In one embodiment, the composition comprises:
(i) at least one of the polypeptides of SEQ ID NO: 74 (BIR12B; AKYMVIQGEPGRVIRGK), SEQ ID NO: 72 (BIR11; FPQFKPQEITGIMK), SEQ ID NO: 71 (BIR10; GSVWAQSSSFPQFK), SEQ ID NO: 73 (BIR12A; PTGMFVAGAKYMVIQGR), SEQ ID NO: 75 (BIR13; IKYMVIQGEAGAVIRGK and SEQ ID NO: 76 (BIR14; EAGAVIRGKKGSGGIT), or a variant of any thereof, and
ii) at least one of the polypeptides of SEQ ID NO: 53 (Bir02J; PAARMFKAFILEGDKLVPK), SEQ ID NO: 48 (Bir01I; FNYETETTSVIPAARK), SEQ ID NO: 54 (Bir04; PGTIKKISFPEGFPFKYV), SEQ ID NO: 67 (Bir09; ETLLRAVESYLLAHSDAY), SEQ ID NO: 60 (BIR07; SNEIKIVATPDGGSILK), and SEQ ID NO: 63 (Bir07C; SNEIKIVATPEGGSILK), or a variant of any thereof.

In another embodiment, the composition further comprises at least one additional polypeptide of (i) or (ii) or variant thereof not selected above. In another embodiment, the composition further comprises at least one additional polypeptide of SEQ ID NO: 77 (BIR15; SLNTLRLRRIFDLFDK) or SEQ ID NO: 78 (BIR16A; AERERIFKRFDANGEGK), or a variant of any thereof. In a preferred embodiment, the composition comprises:
(a) the polypeptide SEQ ID NO: 74 (Bir12B; AKYMVIQGEPGRVIRGK), or a variant thereof;
(b) the polypeptide SEQ ID NO: 53 (Bir02J; PAARMFKAFILEGDKLVPK), or a variant thereof; and
(c) the polypeptide SEQ ID NO: 48 (Bir01I; FNYETETTSVIPAARK) or a variant thereof;

In a particularly preferred embodiment, the composition comprises the polypeptide SEQ ID NO: 74 (Bir12B; AKYMVIQGEPGRVIRGK) or a variant thereof, the polypeptide SEQ ID NO: 53 (Bir02J; PAARMFKAFILEGDKLVPK) or a variant thereof, the polypeptide SEQ ID NO: 48 (Bir01I; FNYETETTSVIPAARK) or a variant thereof, the polypeptide SEQ ID NO: 54 (Bir04; PGTIKKISFPEGFPFKYV) or a variant thereof, the polypeptide SEQ ID NO: 67 (Bir09; ETLLRAVESYLLAHSDAY) or a variant thereof, the polypeptide SEQ ID NO: 63 (Bir07C; SNEIKIVATPEGGSILK) or a variant thereof, and the polypeptide SEQ ID NO: 78 (Bir16A; AERERIFKRFDANGEGK) or a variant thereof, and optionally no further polypeptides.

In a further particularly preferred embodiment, the composition comprises the polypeptide SEQ ID NO: 74 (Bir12B; AKYMVIQGEPGRVIRGK) or a variant thereof, the polypeptide SEQ ID NO: 53 (Bir02J; PAARMFKAFILEGDKLVPK) or a variant thereof, the polypeptide SEQ ID NO: 48 (Bir01I; FNYETETTSVIPAARK) or a variant thereof, the polypeptide SEQ ID NO: 54 (Bir04; PGTIKKISFPEGFPFKYV) or a variant thereof, the polypeptide SEQ ID NO: 63 (Bir07C; SNEIKIVATPEGGSILK) or a variant thereof, the polypeptide SEQ ID NO: 78 (Bir16A; AERERIFKRFDANGEGK) or a variant thereof, and the polypeptide SEQ ID NO: 69 (Bir09B; KEMGERLLRAVESYLLAHS) or a variant thereof, and optionally no further polypeptides.

In a further particularly preferred embodiment, the composition comprises the polypeptide SEQ ID NO: 74 (Bir12B; AKYMVIQGEPGRVIRGK) or a variant thereof, the polypeptide SEQ ID NO: 53 (Bir02J; PAARMFKAFILEGDKLVPK) or a variant thereof, the polypeptide SEQ ID NO: 48 (Bir01I; FNYETETTSVIPAARK) or a variant thereof, the polypeptide SEQ ID NO: 54 (Bir04; PGTIKKISFPEGFPFKYV) or a variant thereof, the polypeptide SEQ ID NO: 63 (Bir07C; SNEIKIVATPEGGSILK) or a variant thereof, and the polypeptide SEQ ID NO: 78 (Bir16A; AERERIFKRFDANGEGK) or a variant thereof, and optionally no further polypeptides.

The invention also provides a product comprising a peptide, variant or composition according to the invention. The invention provides a product comprising:
i) at least one of the polypeptides of SEQ ID NO: 74 (BIR12B; AKYMVIQGEPGRVIRGK), SEQ ID NO: 72 (BIR11; FPQFKPQEITGIMK), SEQ ID NO: 71 (BIR10; GSVWAQSSSFPQFK), SEQ ID NO: 73 (BIR12A; PTGMFVAGAKYMVIQGR), SEQ ID NO: 75 (BIR13; IKYMVIQGEAGAVIRGK and SEQ ID NO: 76 (BIR14; EAGAVIRGKKGSGGIT), or a variant of any thereof as defined in (I) to (III), and
ii) at least one of the polypeptides of SEQ ID NO: 53 (Bir02J; PAARMFKAFILEGDKLVPK), SEQ ID NO: 48 (Bir01I; FNYETETTSVIPAARK), SEQ ID NO: 54 (Bir04; PGTIKKISFPEGFPFKYV), SEQ ID NO: 67 (Bir09; ETLLRAVESYLLAHSDAY), SEQ ID NO: 60 (BIR07; SNEIKIVATPDGGSILK), and SEQ ID NO: 63 (Bir07C; SNEIKIVATPEGGSILK), or a variant of any thereof as defined in (I) to (III), wherein each different polypeptide is for simultaneous, separate or sequential use in preventing or treating allergy to birch pollen by tolerisation.

Variants of the polypeptides of SEQ ID NOS: 1 to 80 are mentioned herein. A variant of any of SEQ ID NOS: 1 to 80 will typically be functional. By functional it is meant that the variant is one which:
(a) comprises or consists of a sequence which binds to the same MHC class II molecule as the corresponding polypeptide of SEQ ID NOS: 1 to 80; and/or
(b) comprises or consists of a sequence which is recognised by a T cell which recognises the corresponding polypeptide of SEQ ID NOS: 1 to 80; and/or
(c) is capable of inducing a late phase response in an individual with birch allergy; and/or
(d) is capable of tolerising an individual to the corresponding polypeptide.

Recognition by a T cell may be tested by measuring the ability of a peptide or variant to induce T cell proliferation in a sample of T cells. The induction of a late phase response may also be tested in this way when the sample of T cells is taken from an individual with birch allergy. Methods of testing the induction of T cell proliferation are well known in the art and one such method is exemplified in Example 8.

Variants of SEQ ID NOS: 1 to 80 may be fragments derived by truncation, e.g. by removal of one or more amino acids from the N and/or C-terminal ends of a polypeptide. Fragments may also be generated by one or more internal deletions, provided that the core 9 amino acids that makes up the T cell epitope is not substantially disrupted.

For example, a variant of SEQ ID NO: 1 may comprise a fragment of SEQ ID NO: 1, i.e. a shorter sequence. This may include a deletion of one, two, three or four amino acids from the N-terminal end of SEQ ID NO: 1 or from the C-terminal end of SEQ ID NO: 1. Such deletions may be made from both ends of SEQ ID NO: 1.

A variant of SEQ ID NO: 1 may include additional amino acids (for example from the sequence of the parent protein from which the peptide derives) extending beyond the end(s) of SEQ ID NO: 1. A variant of a polypeptide may typically be a longer polypeptide of up to 20, 21, 22, 23, 24, 25, 26, 27, 28, 29 or 30 amino acids in length which comprises the sequence of the corresponding polypeptide of SEQ ID NOS: 1 to 80.

A variant may include a combination of the deletions and additions discussed above. For example, amino acids may be deleted from one end of SEQ ID NO: 1, but additional amino acids from the full length parent protein sequence may be added at the other end of SEQ ID NO: 1. The same discussion of variants above also applies to SEQ ID NOS: 2 to 80.

A variant may alternatively be a polypeptide of 9 to 30, 11 to 20 or 13 to 17 amino acids in length which comprises a sequence that has at least 65% sequence identity to the sequence of the corresponding polypeptide of SEQ ID NOS: 1 to 80. More preferably a suitable variant may comprise at least 70%, at least 75%, at least 80%, at least 85%, at least 90%, at least 95%, or at least 98% amino acid identity to the corresponding polypeptide of SEQ ID NOS: 1 to 80.

A variant may be a polypeptide of length 9 to 30, 11 to 20 or 13 to 17 amino acids which comprises a sequence of, or a sequence that has, at least 65% sequence identity to at least 9 (for example at least 10, 11, 12 or 13) or more contiguous amino acids of the sequence of the corresponding polypeptide of SEQ ID NOS: 1 to 80. These contiguous amino acids may typically comprise a MHC class II epitope, for example which binds to any of the MHC molecules mentioned herein.

A variant peptide may include one or more amino acid substitutions from the amino acid sequence of any of SEQ ID NOS: 1 to 80 or a fragment thereof. A variant peptide may comprise sequence having at least 65% sequence identity to at least 9 or more contiguous amino acids in any of SEQ ID NOS: 1 to 80. More preferably a suitable variant may comprise at least 70%, at least 75%, at least 80%, at least 85%, at least 90%, at least 95%, or at least 98% amino acid identity to at least 9 contiguous amino acids of any of SEQ ID NOS: 1 to 80. This level of amino acid identity may be seen at any section of the peptide, although it is preferably the core region. The level of amino acid identity is over at least 9 contiguous amino acids but it may be at least 10, 11, 12, 13, 14, 15 or at least 16 or 17 amino acids, depending on the size of the peptides of comparison. Accordingly, any of the above-specified levels of identity may be across the entire length of sequence.

In connection with amino acid sequences, "sequence identity" refers to sequences which have the stated value when assessed using ClustalW (Thompson et al., 1994, supra) with the following parameters:
Pairwise alignment parameters—Method: accurate, Matrix: PAM, Gap open penalty: 10.00, Gap extension penalty: 0.10; Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

A variant peptide may comprise 1, 2, 3, 4, 5 or more, or up to 10 amino acid substitutions from any of SEQ ID NOS: 1 to 80. Substitution variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

Further variants include those in which instead of the naturally occurring amino acid the amino acid which appears in the sequence is a structural analog thereof. Amino acids used in the sequences may also be modified, e.g. labelled, providing the function of the peptide is not significantly adversely affected.

Where the peptide has a sequence that varies from the sequence of any of SEQ ID NOS: 1 to 80 or a fragment thereof, the substitutions may occur across the full length of the sequence, within the sequence of any of SEQ ID NOS: 1 to 80 or outside the sequence of any of SEQ ID NOS: 1 to 80. For example, the variations described herein, such as additions, deletions, substitutions and modifications, may occur within the sequence of any of SEQ ID NOS: 1 to 80. A variant peptide may comprise or consist essentially of the amino acid sequence of any of SEQ ID NOS: 1 to 80 in which one, two, three, four or more amino acid substitutions have been made. A variant peptide may comprise a fragment of the parent protein that is larger than any of SEQ ID NOS: 1 to 80. In this embodiment, the variations described herein, such as substitutions and modifications, may occur within and/or outside the sequence of any of SEQ ID NOS: 1 to 80. For example, one or more positively charged residues may be added at the N and/or C terminus of the native sequence of the peptide of any of SEQ ID NOS: 1 to 80.

The variant peptides of the invention are 9 to 30 amino acids in length inclusive. Preferably, they may be from 9 to 20 or more preferably 13 to 17 amino acids in length. The peptides may be the same length as the peptide sequences in any one of SEQ ID NOS: 1 to 80.

The peptides may be chemically derived from the polypeptide allergen, for example by proteolytic cleavage or can be derived in an intellectual sense from the polypeptide allergen, for example by making use of the amino acid sequence of the polypeptide allergen and synthesising peptides based on the sequence. Peptides may be synthesised using methods well known in the art.

The term "peptide" includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the peptide may conveniently be blocked at its N- or C-terminus so as to help reduce susceptibility to exoproteolytic digestion. For example, the N-terminal amino group of the peptides may be protected by reacting with a carboxylic acid and the C-terminal carboxyl group of the peptide may be protected by reacting with an amine. Other examples of modifications include glycosylation and phosphorylation. Another potential modification is that hydrogens on the side chain amines of R or K may be replaced with methylene groups (—$NH_2$→—NH(Me) or —N(Me)$_2$).

Analogues of peptides according to the invention may also include peptide variants that increase or decrease the peptide's half-life in vivo. Examples of analogues capable of increasing the half-life of peptides used according to the invention include peptoid analogues of the peptides, D-amino acid derivatives of the peptides, and peptide-peptoid hybrids. A further embodiment of the variant polypeptides used according to the invention comprises D-amino acid forms of the polypeptide. The preparation of polypeptides using D-amino acids rather than L-amino acids greatly decreases any unwanted breakdown of such an agent by normal metabolic processes, decreasing the amounts of agent which needs to be administered, along with the frequency of its administration.

The peptides provided by the present invention may be derived from splice variants of the parent proteins encoded by mRNA generated by alternative splicing of the primary transcripts encoding the parent protein chains. The peptides may also be derived from amino acid mutants, glycosylation variants and other covalent derivatives of the parent proteins which retain at least an MHC-binding property of the allergens. Exemplary derivatives include molecules wherein the peptides of the invention are covalently modified by substitution, chemical, enzymatic, or other appropriate means with a moiety other than a naturally occurring amino acid. Further included are naturally occurring variants of the parent proteins found in different mites. Such a variant may be encoded by an allelic variant or represent an alternative splicing variant.

Variants as described above may be prepared during synthesis of the peptide or by post-production modification, or when the peptide is in recombinant form using the known techniques of site-directed mutagenesis, random mutagenesis, or enzymatic cleavage and/or ligation of nucleic acids.

In any of the embodiments of the invention, typical examples of variants as described herein may be as follows:
  a variant of Bir01I is SEQ ID NO: 45 (Bir01F; FNYETEATSVIPAARK), SEQ ID NO: 46 (Bir01G; FNYEIEATSVIPAARK) or SEQ ID NO: 47 (Bir01H; FNYEIETTSVIPAARK); and/or
  a variant of Bir02J is SEQ ID NO: 50 (Bir02E; PAARLFKAFILEGDTLIPK), SEQ ID NO: 51 (Bir02G; PAARLFKAFILEGDNLIPK), SEQ ID NO: 52 (Bir02I; PAARMFKAFILD) or SEQ ID NO: 49 (Bir02D; PAARMFKAFILDGDKLVPK); and/or
  a variant of Bir09 is selected from SEQ ID NO: 68 (Bir09A; GETLLRAVESYLLAHS), SEQ ID NO: 69 (Bir09B; KEMGETLLRAVESYLLAHS) or SEQ ID NO: 70 (Bir09C; KEKGETLLRAVESYLLAHS); and/or
  a variant of Bir16B is SEQ ID NO: 78 (Bir16A; AERERIFKRFDANGEGK).

It will be understood that SEQ ID NOS: 1 to 80 are polypeptide sequences which comprise a T cell epitope that consists of a core of typically 9 amino acids, which are the minimal essential sequence required for MHC class II binding. However, the polypeptides of SEQ ID NOS: 1 to 80 may also comprise additional residues flanking the core. The peptides may therefore comprise a region containing a T cell epitope, in which some residues may be modified without affecting the function of the epitope. Thus, for example, the sequences of any of SEQ ID NOS: 1 to 80 may be altered to improve their solubility, and accordingly a variant of any of SEQ ID NOS: 1 to 80 will preferably be more soluble than the corresponding polypeptide of SEQ ID NOS: 1 to 80 under equivalent conditions. Methods for evaluating the solubility of peptides are well known in the art and one such method is exemplified in Example 9.

Improved solubility is advantageous for the tolerisation of subjects to allergens from which the peptides of the invention derive, since administration of poorly soluble agents to subjects causes undesirable, non-tolerising inflammatory responses. The solubility of the peptides may be improved by altering the residues which flank the region containing a T cell epitope. A peptide of the invention may be engineered to be more soluble such that it comprises:
  i) N terminal to the residues of the peptide which flank a T cell epitope: one to six contiguous amino acids corresponding to the one to six contiguous amino acids immediately N terminal to said residues in the sequence of the protein from which the peptide derives; and/or
  ii) C terminal to the residues of the peptide which flank a T cell epitope: one to six contiguous amino acids corresponding to the one to six contiguous amino acids immediately C terminal to the said residues in the sequence of the protein from which the peptide derives; or
  iii) both N and C terminal to the residues of the peptide which flank a T cell epitope, at least one amino acid selected from arginine, lysine, histidine, glutamate and aspartate.

Optionally, the peptides may additionally be engineered to be more soluble such that:
  i) any cysteine residues in the native sequence of the peptide are replaced with serine or 2-aminobutyric acid; and/or
  ii) any hydrophobic residues in the upto three amino acids at the N or C terminus of the native sequence of the peptide, which are not comprised in a T cell epitope, are deleted; and/or
  iii) any two consecutive amino acids comprising the sequence Asp-Gly in the upto four amino acids at the N or C terminus of the native sequence of the peptide, which are not comprised in a T cell epitope, are deleted; and/or
  iv) one or more positively charged residues are added at the N and/or C terminus of the native sequence of the peptide.

Preferably the peptides and variants of the invention are capable of causing T cell proliferation in at least 20% of samples of T cells, wherein each sample is obtained from different birch allergic individuals in the population. The compositions of the invention are preferably capable of inducing T cell proliferation in 30% or more samples of T cells obtained from of a panel of birch allergic individuals. More preferably, the compositions are capable of inducing T cell proliferation in 35% or more, 40% or more, 45%, 50%, 55%, 60%, 65%, 70%, 75%, 80%, 85%, or 90% or more of samples obtained from sensitized individuals in a panel. The number of individuals in a panel of birch allergic individuals may be any number greater than one, for example at least 2, 3, 5, 10, 15, 20, 30, 50, 80, or at least 100 individuals.

It is preferred if the peptides, variants and compositions of the invention cause T cell proliferation, but do not lead to the release of histamine from enriched basophils or mast cell preparations from a sensitised individual. There may be some histamine release, but preferably the peptides, variants and compositions do not cause significant amounts of histamine to be released. Significant histamine release may be considered to be the release of 20% or more of the total available leukocyte histamine when a sample of leukocytes from an individual is stimulated with a composition in vitro. A peptide, variant or composition of the invention preferably causes the release of less than 5%, less than 4%, less than 3%, less than 2% or less than 1% of the total available leukocyte histamine when a sample of leukocytes from an individual is stimulated with a composition in vitro. A normal individual typically has an approximate leukocyte histamine content of 150 ng/$10^7$ cells.

Suitable peptides or variants capable of binding to TCRs may be derived empirically or selected according to known criteria. Within a single peptide there are certain residues which contribute to binding within the MHC antigen binding groove and other residues which interact with hypervariable regions of the T cell receptor (Allen et al (1987) Nature 327: 713-5).

Within the residues contributing to T cell receptor interaction, a hierarchy has been demonstrated which pertains to dependency of T cell activation upon substitution of a given peptide residue. Using peptides which have had one or more T cell receptor contact residues substituted with a different amino acid, several groups have demonstrated profound effects upon the process of T cell activation. Evavold & Allen (1991) Nature 252: 1308-10) demonstrated the dissociation of T cell proliferation and cytokine production. In this in vitro model, a T cell clone specific for residues 64-76 of haemoglobin (in the context of I-$E^k$), was challenged with a peptide analogue in which a conservative substitution of aspartic acid for glutamic acid had been made. This substitution did not significantly interfere with the capacity of the analogue to bind to I-$E^k$.

Following in vitro challenge of a T cell clone with this analogue, no proliferation was detected although IL-4 secretion was maintained, as was the capacity of the clone to help B cell responses. In a subsequent study the same group demonstrated the separation of T cell-mediated cytolysis from cytokine production. In this instance, the former remained unaltered while the latter was impaired. The efficacy of altered peptide ligands in vivo was initially demonstrated in a murine model of EAE (experimental allergic encephalomyelitis) by McDevitt and colleagues (Smilek et al (1991) Proc Natl Acad Sci USA 88: 9633-9637). In this model EAE is induced by immunisation with the encephalitogenic peptide Acl-11 of MBP (myelin basic protein). Substitution at position four (lysine) with an alanine residue generated a peptide which bound well to its restricting element ($A\alpha^u A\beta^u$), but which was non-immunogenic in the susceptible PL/JxSJLF1 strain and which, furthermore prevented the onset of EAE when administered either before or after immunisation with the encephalitogenic peptide. Thus, residues can be identified in peptides which affect the ability of the peptides to induce various functions of T-cells.

Advantageously, peptides may be designed to favour T-cell proliferation and induction of desensitisation. Metzler and Wraith have demonstrated improved tolerogenic capacity of peptides in which substitutions increasing peptide-MHC affinity have been made (Metzler & Wraith (1993) Int Immunol ~: 1159-65). That an altered peptide ligand can cause long-term and profound anergy in cloned T cells was demonstrated by Sloan-Lancaster et al (1993) Nature 363: 156-9.

The compositions of the invention are capable of inducing a late phase response in an individual that is sensitised to the allergens. The term "late phase response" includes the meaning as set forth in Allergy and Allergic Diseases (1997) A. B. Kay (Ed.), Blackwell Science, pp 1113-1130. The late phase response may be any late phase response (LPR). Preferably, the peptides are capable of inducing a late asthmatic response (LAR) or a late rhinitic response, or a late phase skin response or a late phase ocular response. Whether or not a particular peptide can give rise to a LPR can be determined using methods well known in the art; a particularly preferred method is that described in Cromwell O, Durham S R, Shaw R J, Mackay J and Kay A B. Provocation tests and measurements of mediators from mast cells and basophils in asthma and allergic rhinitis. In: Handbook of Experimental Immunology (4) Chapter 127, Editor: Weir D M, Blackwell Scientific Publications, 1986.

Thus, preferably, the individual peptides and variants of the invention are able to induce a LPR in an individual who has been sensitised to the allergens. Whether or not an individual has been sensitised to the allergens may be determined by well known procedures such as skin prick testing with solutions of allergen extracts, induction of cutaneous LPRs, clinical history, allergen challenge and radioallergosorbent test (RAST) for measurement of allergen specific IgE. Whether or not a particular individual is expected to benefit from treatment may be determined by the physician based, for example, on such tests.

Desensitising or tolerising an individual to the allergens means inhibition or dampening of allergic tissue reactions induced by the allergens in appropriately sensitised individuals. It has been shown that T cells can be selectively activated, and then rendered unresponsive. Moreover the anergising or elimination of these T-cells leads to desensitisation of the patient for a particular allergen. The desensitisation manifests itself as a reduction in response to an allergen or allergen-derived peptide, or preferably an elimination of such a response, on second and further administrations of the allergen or allergen-derived peptide. The second administration may be made after a suitable period of time has elapsed to allow desensitisation to occur; this is preferably any period between one day and several weeks. An interval of around two weeks is preferred.

Although the compositions of the invention are able to induce a LPR in a birch allergic individual, it should be appreciated that when a composition is used to treat a patient it is preferable that a sufficiently low concentration of the composition is used such that no observable LPR will occur but the response will be sufficient to partially desensitise the T cells such that the next (preferably higher) dose may be given, and so on. In this way the dose is built up to give full desensitisation but often without ever inducing a LPR in the patient. Although, the composition or peptide is able to do so at a higher concentration than is administered.

The compositions of the invention preferably are capable of inducing a late phase response in 50% or more of a panel of birch allergic individuals from the population. More preferably, the compositions are capable of inducing a LPR in 55% or more, 60% or more, 65% or more, 70% or more, 75% or more, 80% or more, 85% or more, or 90% or more of sensitized individuals in a panel. Whether or not the compositions are able to induce a LPR in a certain percentage of a panel of subjects can be determined by methods which are well known in the art.

Nucleic Acids and Vectors

The individual peptides that make up the compositions and products of the invention may be administered directly, or may be administered indirectly by expression from an encoding sequence. For example, a polynucleotide may be provided that encodes a peptide of the invention, such as any of the peptides described above. A peptide of the invention may thus be produced from or delivered in the form of a polynucleotide which encodes, and is capable of expressing, it. Any reference herein to the use, delivery or administration of a peptide of the invention is intended to include the indirect use, delivery or administration of such a peptide via expression from a polynucleotide that encodes it.

Accordingly, the invention provides a composition for use in preventing or treating allergy to birch by tolerisation comprising at least one polynucleotide sequence which when expressed causes the production of a composition according to the invention for use in preventing or treating allergy to birch by tolerisation.

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form. A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides of the invention can be synthesised according to methods well known in the art, as described by way of example in Sambrook et al (1989, Molecular Cloning—a laboratory manual; Cold Spring Harbor Press).

The polynucleotide molecules of the present invention may be provided in the form of an expression cassette which includes control sequences operably linked to the inserted sequence, thus allowing for expression of the peptide of the invention in vivo in a targeted subject. These expression cassettes, in turn, are typically provided within vectors (e.g., plasmids or recombinant viral vectors) which are suitable for use as reagents for nucleic acid immunization. Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a peptide of the invention.

Expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

Thus, a polypeptide of the invention may be provided by delivering such a vector to a cell and allowing transcription from the vector to occur. Thus, the invention also provides a vector for use in preventing or treating allergy to birch pollen by tolerisation comprising four or more polynucleotide sequences which encode a different polypeptide of the invention. Preferably, a polynucleotide of the invention or for use in the invention in a vector is operably linked to a control sequence which is capable of providing for the expression of the coding sequence by the host cell, i.e. the vector is an expression vector.

"Operably linked" refers to an arrangement of elements wherein the components so described are configured so as to perform their usual function. Thus, a given regulatory sequence, such as a promoter, operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

A number of expression systems have been described in the art, each of which typically consists of a vector containing a gene or nucleotide sequence of interest operably linked to expression control sequences. These control sequences include transcriptional promoter sequences and transcriptional start and termination sequences. The vectors of the invention may be for example, plasmid, virus or phage vectors provided with an origin of replication, optionally a promoter for the expression of the said polynucleotide and optionally a regulator of the promoter. A "plasmid" is a vector in the form of an extrachromosomal genetic element. The vectors may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example to allow in vivo expression of the polypeptide.

A "promoter" is a nucleotide sequence which initiates and regulates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

A polynucleotide, expression cassette or vector according to the present invention may additionally comprise a signal peptide sequence. The signal peptide sequence is generally inserted in operable linkage with the promoter such that the signal peptide is expressed and facilitates secretion of a polypeptide encoded by coding sequence also in operable linkage with the promoter.

Typically a signal peptide sequence encodes a peptide of 10 to 30 amino acids for example 15 to 20 amino acids. Often the amino acids are predominantly hydrophobic. In a typical situation, a signal peptide targets a growing polypeptide chain bearing the signal peptide to the endoplasmic reticulum of the expressing cell. The signal peptide is cleaved off in the endoplasmic reticulum, allowing for secretion of the polypeptide via the Golgi apparatus. Thus, a peptide of the invention may be provided to an individual by expression from cells within the individual, and secretion from those cells.

Alternatively, polynucleotides of the invention may be expressed in a suitable manner to allow presentation of a peptide of the invention by an MHC class II molecule at the surface of an antigen presenting cell. For example, a polynucleotide, expression cassette or vector of the invention may be targeted to antigen presenting cells, or the expression of encoded peptide may be preferentially stimulated or induced in such cells.

In some embodiments, the polynucleotide, expression cassette or vector will encode an adjuvant, or an adjuvant will otherwise be provided. As used herein, the term "adjuvant" refers to any material or composition capable of specifically or non-specifically altering, enhancing, directing, redirecting, potentiating or initiating an antigen-specific immune response.

Polynucleotides of interest may be used in vitro, ex vivo or in vivo in the production of a peptide of the invention. Such polynucleotides may be administered or used in the prevention or treatment of allergy by tolerisation.

Methods for gene delivery are known in the art. See, e.g., U.S. Pat. Nos. 5,399,346, 5,580,859 and 5,589,466. The nucleic acid molecule can be introduced directly into the recipient subject, such as by standard intramuscular or intradermal injection; transdermal particle delivery; inhalation; topically, or by oral, intranasal or mucosal modes of administration. The molecule alternatively can be introduced ex vivo into cells that have been removed from a subject. For example, a polynucleotide, expression cassette or vector of the invention may be introduced into APCs of an individual ex vivo. Cells containing the nucleic acid molecule of interest are re-introduced into the subject such that an immune response can be mounted against the peptide encoded by the nucleic acid molecule. The nucleic acid molecules used in such immunization are generally referred to herein as "nucleic acid vaccines."

The polypeptides, polynucleotides, vectors or cells of the invention may be present in a substantially isolated form. They may be mixed with carriers or diluents which will not interfere with their intended use and still be regarded as substantially isolated. They may also be in a substantially purified form, in which case they will generally comprise at least 90%, e.g. at least 95%, 98% or 99%, of the proteins, polynucleotides, cells or dry mass of the preparation.

Antigen Presenting Cells (APCs)

The invention encompasses the use in vitro of a method of producing a population of APCs that present the peptides of the invention on their surface, that may be subsequently used in therapy. Such a method may be carried out ex vivo on a sample of cells that have been obtained from a patient. The APCs produced in this way therefore form a pharmaceutical agent that can be used in the treatment or prevention of birch allergy by tolerisation. The cells should be accepted by the immune system of the individual because they derive from that individual. Delivery of cells that have been produced in this way to the individual from whom they were originally obtained, thus forms a therapeutic embodiment of the invention.

Formulations and Compositions

The peptides, polynucleotides, vectors and cells of the invention may be provided to an individual either singly or in combination. Each molecule or cell of the invention may be provided to an individual in an isolated, substantially isolated, purified or substantially purified form. For example, a peptide of the invention may be provided to an individual substantially free from the other peptides. Alternatively, four or more peptides in the composition may be coupled chemically together, using standard peptide coupling reagents, to provide a single peptide containing the preferred epitopes. Such peptides would be screened for basophil histamine release to confirm lack of histamine release as per the individual peptides. In a further embodiment, four or more peptides in the composition may be provided as part of a single polypeptide chain i.e by recombinant means from an encoding polynucleotide. The four or more peptides may be fused contiguously, or may alternatively be separated by appropriate linkers.

Whilst it may be possible for the peptides, polynucleotides or compositions according to the invention to be presented in raw form, it is preferable to present them as a pharmaceutical formulation. Thus, according to a further aspect of the invention, the present invention provides a pharmaceutical formulation for use in preventing or treating allergy to birch by tolerisation comprising a composition, vector or product according to the invention together with one or more pharmaceutically acceptable carriers or diluents and optionally one or more other therapeutic ingredients. The carrier (s) must be 'acceptable' in the sense of being compatible with the other ingredients of the formulation and not deleterious to the recipient thereof. Typically, carriers for injection, and the final formulation, are sterile and pyrogen free. Preferably, the carrier or diluent is thioglycerol or thioanisole.

Formulation of a composition comprising the peptide, polynucleotides or cells of the invention can be carried out using standard pharmaceutical formulation chemistries and methodologies all of which are readily available to the reasonably skilled artisan.

For example, compositions containing one or more molecules or cells of the invention can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol, thioglycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (for e.g., a powder or granules) form for reconstitution with a suitable vehicle (e.g., sterile pyrogen-free water) prior to parenteral administration of the reconstituted composition. The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other parentally-administrable compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Alternatively, the peptides or polynucleotides of the present invention may be encapsulated, adsorbed to, or associated with, particulate carriers. Suitable particulate carriers include those derived from polymethyl methacrylate polymers, as well as PLG microparticles derived from poly(lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

The formulation of any of the peptides, polynucleotides or cells mentioned herein will depend upon factors such as the nature of the substance and the method of delivery. Any such substance may be administered in a variety of dosage forms. It may be administered orally (e.g. as tablets, troches, lozenges, aqueous or oily suspensions, dispersible powders or granules), topically, parenterally, subcutaneously, by inhalation, intravenously, intramuscularly, intrasternally, transdermally, intradermally, sublingually, intranasally, buccally or by infusion techniques. The substance may also be administered as suppositories. A physician will be able to determine the required route of administration for each particular individual.

The compositions of formulations of the invention will comprise a suitable concentration of each peptide/polynucleotide/cell to be effective without causing adverse reaction. Typically, the concentration of each peptide in the composition will be in the range of 0.03 to 200 nmol/ml. More preferably in the range of 0.3 to 200 nmol/ml, 3 to 180 nmol/ml, 10 to 150 nmol/ml, 50 to 200 nmol/ml or 30 to 120 nmol/ml. The composition or formulations should have a purity of greater than 95% or 98% or a purity of at least 99%.

In one aspect of the invention an adjuvant may be used in combination with the polypeptide/polynucleotides/cells of the invention. The adjuvant is preferably administered in an amount which is sufficient to augment the effect of the polypeptide/polynucleotides/cells of the invention or vice versa. The adjuvant or other therapeutic agent may be an agent that potentiates the effects of the molecule of the invention. For example, the other agent may be an immunomodulatory molecule or an adjuvant which enhances the response to the peptide or cell of the invention.

In one embodiment, therefore, the peptides, polynucleotides, cells or compositions of the invention are used for therapy in combination with one or more other therapeutic agents. The agents may be administered separately, simultaneously or sequentially. They may be administered in the same or different compositions. Accordingly, in a method of the invention, the subject may also be treated with a further therapeutic agent.

A composition may therefore be formulated which comprises a molecule and/or cell of the invention and also one or more other therapeutic molecules. A composition of the invention may alternatively be used simultaneously, sequentially or separately with one or more other therapeutic compositions as part of a combined treatment.

Non-limiting examples of adjuvants include vitamin D, rapamycin and glucocorticoid steroids such as dexamethasone, fluticasone, budesonide, mometasone, beclomethasone, hydrocortisone, cortisone acetate, prednisone, prednisolone, methylprednisolone, betamethasone and triamcinolone. A preferred glucocorticoid is dexamethasone.

Therapeutic Methods and Individual to be Treated

The present invention relates to peptides, polynucleotides, vectors and cells that are capable of desensitising or tolerising human individuals to the allergens described above and are therefore useful in the prevention or treatment of birch allergy. The invention provides compositions, products, vectors and formulations for use in preventing or treating allergy to birch by tolerisation. The invention also provides a method of tolerising or desensitizing a birch allergic individual comprising administering, either singly or in combination the polypeptides/polynucleotides/cells of the invention as described above.

The individual to be treated or provided with the composition or formulation of the invention is preferably human. It will be appreciated that the individual to be treated may be known to be sensitised to the allergens, at risk of being sensitised or suspected of being sensitised. The individual can be tested for sensitisation using techniques well known in the art and as described herein. Alternatively, the individual may have a family history of allergy to birch. It may not be necessary to test an individual for sensitisation to birch because the individual may display symptoms of allergy when exposed to birch. By exposure is meant proximity to, for example, a birch plant, or a substance or product derived from a birch plant, or a substance or product containing or comprising either of the above. The substance or product derived from a birch plant is typically birch pollen. By proximity is meant 10 metres or less, 5 metres or less, 2 metres or less, 1 metre or less, or 0 metres from the items described above. Symptoms of allergy can include itchy eyes, runny nose, breathing difficulties, red itchy skin or rash.

The individual to be treated may be of any age. However, preferably, the individual may be in the age group of 1 to 90, 5 to 60, 10 to 40, or more preferably 18 to 35.

Preferably, the individual to be treated is from a population that has MHC allele frequencies within the range of frequencies that are representative of the Caucasian population. Reference population allele frequencies for 11 common DRB1 allele families are shown in Table 1 (Data from HLA Facts Book, Parham and Barber).

TABLE 1

| DRB1 | 1 | 3 | 4 | 7 | 8 | 11 | 12 | 13 | 14 | 15 | 16 |
|---|---|---|---|---|---|---|---|---|---|---|---|
| % | 6.4 | 14.7 | 15.7 | 8.8 | 3.4 | 8.3 | 3.9 | 14.7 | 2.9 | 17.6 | 2.5 |
| Reference population % | 9.4 | 11.1 | 12.8 | 13.2 | 3.7 | 13.4 | 2.3 | 10.2 | 3.2 | 10.7 | 3.6 |

Reference frequencies were obtained by analysis of multiple studies reporting frequencies and the figures shown are mean values. Preferably therefore, the individual to be treated is from a population that has equivalent MHC allele frequencies as the reference population for the alleles referred to Table 1 (such as for at least 1, 2, 3, 4, 5 or all of the alleles), for example within the ranges of those figures plus or minus 1, 2, 3, 5, 10, 15 or 20%.

Preferably the individual is from a population where the allele frequencies of the following DRB1 alleles is:

4—at least 9%

7—at least 10%

11—at least 8%.

The individual may have had allergy to birch for at least 2 weeks, 1 month, 6 months, 1 year or 5 years. The individual may suffer from a rash, nasal congestion, nasal discharge and/or coughing caused by the allergy. The individual may or may not have been administered with other compositions/compounds which treat birch allergy. The individual may live in a geographical region which has:

a temperate, boreal or arctic climate, and/or:

a typical soil pH in the range of about 3.5, to about 7.5.

The individual typically suffers from allergy to birch pollen in a particular season. The season typically corresponds to the flowering season of birch, which is typically spring, preferably early spring (for example from April to May in the Northern hemisphere). The allergic individual is typically allergic to birch pollen from any tree in the subgenus *Betula*, for example *Betula pendula* or *Betula pubescens*.

Combination Immunotherapy

Since many individuals are allergic, or may require desensitizing to several polypeptide antigens, the current invention also provides means of desensitizing individuals that are allergic to multiple antigens. "Tolerance" induced in an individual to a first polypeptide antigen or allergen can create in the individual a "tolergeneic environment" wherein inappropriate immune responses to other antigens can be downregulated in order to provide tolerance to other antigens.

This finding means that individuals allergic to multiple allergens can be treated in a greatly reduced time period, and that individuals seriously allergic to some allergens (e.g., peanuts) but more mildly allergic to other allergens (e.g., cat dander) can benefit from a therapy wherein tolerance to the milder allergen is established and then this tolergeneic environment is used to provide tolerance to the other, more extreme allergen. In addition, individuals suffering from an autoimmune disorder who are additionally sensitised (or otherwise immune) to an unrelated antigen or allergen can benefit from a treatment regime wherein tolerance to the unrelated antigen or allergen is first established and then this tolergeneic environment is used to provide tolerance to the autoantigen associated with the autoimmune disorder.

A method is therefore provided for desensitising a birch allergic individual to birch allergen as described above and one or more further different polypeptide antigens. The method entails, in a first step, administering to the individual a composition/product/formulation (primary composition) according to the invention as described herein and wherein the administration is carried out in a manner sufficient to generate a hyporesponsive state against birch allergen. Once a hyporesponsive state has been established toward birch allergen, or at least a shift toward desensitisation has occurred, the method entails administration of a secondary composition comprising a second, different polypeptide antigen to which the individual is to be sensitised. Administration of the secondary composition is carried out in such a way as to take advantage of the tolerogenic environment established by use of the primary composition, where it is now possible to establish tolerance to the second, different polypeptide antigen. The secondary composition is coadministered with either the first primary composition or a larger fragment of the birch allergen. By "coadministered" it is meant either the simultaneous or concurrent administration, e.g., when the two are present in the same composition or administered in separate compositions at nearly the same time but at different sites, as well as the delivery of polypeptide antigens in separate compositions at different times. For example, the secondary composition may be delivered prior to or subsequent to delivery of the first composition at the same or a different site. The timing between deliveries can range from about several seconds apart to about several minutes apart, several hours apart, or even several days apart. Furthermore, different delivery methods can be employed.

The second polypeptide antigen is preferably an allergen different to the birch allergen. Suitable allergens for use in the methods of the invention can of course be obtained and/or produced using known methods. Classes of suitable allergens include, but are not limited to, dust mite allergens, pollens, animal dander (especially cat dander), grass allergens, molds, dusts, antibiotics, stinging insect venoms, and a variety of environmental (including chemicals and metals), drug and food allergens. Common tree allergens include pollens from cottonwood, poplar, ash, birch, maple, oak, elm, hickory, and pecan trees; common plant allergens include those from mugwort, ragweed, English plantain, sorrel-dock and pigweed; plant contact allergens include those from poison oak, poison ivy and nettles; common grass allergens include rye grass, Timothy, Johnson, Bermuda, fescue and bluegrass allergens; common allergens can also be obtained from molds or fungi such as *Alternaria, Fusarium, Hormodendrum, Aspergillus, Micropolyspora, Mucor* and thermophilic *actinomycetes*; epidermal allergens can be obtained from house or organic dusts (typically fungal in origin), or from animal sources such as feathers, and dog dander; common food allergens include milk and cheese (dairy), egg, wheat, nut (e.g., peanut), seafood (e.g., shellfish), pea, bean and gluten allergens; common environmental allergens include metals (nickel and gold), chemicals (formaldehyde, trinitrophenol and turpentine), Latex, rubber, fiber (cotton or wool), burlap, hair dye, cosmetic, detergent and perfume allergens; common drug allergens include local anesthetic and salicylate allergens; antibiotic allergens include penicillin, tetracycline and sulfonamide allergens; and common insect allergens include bee, wasp and ant venom, and cockroach calyx allergens. Particularly well characterized allergens include, but are not limited to, the major cat allergen Fel d1, bee venom phospholipase A2 (PLA) (Akdis et al. (1996) J. *Clin. Invest.* 98:1676-1683) and the multi-epitopic recombinant grass allergen rKBG8.3 (Cao et al. (1997) *Immunology* 90:46-51). These and other suitable allergens are commercially available and/or can be readily prepared as extracts following known techniques.

Preferably, the second polypeptide allergen is a whole tree pollen allergen or allergen fragment selected from the list of allergen sequences and database accession numbers (NCBI Entrez accession numbers) below. NCBI is the National Center for Biotechnology information and is a division of the US National Institutes of Health. The NCBI web site, from which access to the database may be sought, is www.ncbi.nlm.nih.gov/. Allergen sequences and database accession numbers (NCBI Entrez accession numbers):

Olive Tree

Olive Sequences

```
SEQ ID NO: 84  416610 Ole e 1
EDIPQPPVSQFHIQGQVYCDTCRAGFITELSEFIPGASLRLQCKDKENG

DVTFTEVGYTRAEGLYSMLVERDHKNEFCEITLISSGRKDCNEIPTEGW

AKPSLKFKLNTVNGTTRTVNPLGFFKKEALPKCAQVYNKLGMYPPNM
```

Tree allergen sequences (mainly birch) sequences:

```
SEQ ID NO: 85  130975 Bet v 2
MSWQTYVDEHLMCDIDGQASNSLASATVGHDGSVWAQSSSFPQFKPQEIT

GIMKDFEEPGHLAPTGLHLGGIKYMVIQGEAGAVIRGKKGSGGITIKKTG

QALVFGIYEEPVTPGQCNMVVERLGDYLIDQGL

SEQ ID NO: 86  1942360 Bet v 2
```

-continued
MSWQTYVDEHLMCDIDGQGEELAASAIVGHDGSVWAQSSSFPQFKPQEIT

GIMKDFEEPGHLAPTGLHLGGIKYMVIQGEAGAVIRGKKGSGGITIKKTG

QALVFGIYEEPVTPGQCNMVVERLGDYLIDQGL

SEQ ID NO: 87 166953 Bet v 2
MSWQTYVDEHLMCDIDGQASNSLASAIVGHDGSVWAQSSSFPQFKPQEIT

GIMKDFEEPGHLAPTGLHLGGIKYMVIQGEAGAVIRGKKGSGGITIKKTG

QALVFGIYEEPVTPGQCNMVVERLGDYLIDQGL

SEQ ID NO: 88 541814 Bet v2
MSWQTYVDEHLMCDIDGQASNSLASALVGHDGSVWAQSSSFPQFKPQEIT

GIMKDFEEPGHLAPTGLHLGGIKYMVIQGEAGAVIRGKKGSGGITIKKTG

QALVFGIYEEPVTPGQCNMVVERLGDYLIDQGL

SEQ ID NO: 89 2488678 Bet v 2
MSWQTYVDEHLMCDIDGQASNSLASAIVGHDGSVWAQSSSFPQFKPQEIT

GIMKDFEEPGHLAPTGLHLGGIKYMVIQGEAGAVIRGKKGSGGITIKKTG

QALVFGIYEEPVTPGQCNMVVERLGDYLIDQGL

SEQ ID NO: 90 1829894 Bet v 2
MSWQTYVDEHLMCDIDGQASNSLASAIVGHDGSVWAQSSSFPQFKPQEIT

GIMKDFEEPGHLAPTGLHLGGIKYMVIQGEAGAVIRGKKGSGGITIKKTG

QALVFGIYEEPVTPGQCNMVVERLGDYLIDQGL

SEQ ID NO: 91 1168696 Bet v 3
MPCSTEAMEKAGHGHASTPRKRSLSNSSFRLRSESLNTLRLRRIFDLFDK

NSDGIITVDELSRALNLLGLETDLSELESTVKSFTREGNIGLQFEDFISL

HQSLNDSYFAYGGEDEDDNEEDMRKSILSQEEADSFGGFKVFDEDGDGYI

SARELQMVLGKLGFSEGSEIDRVEKMIVSVDSNRDGRVDFFEFKDMMRSV

LVRSS

SEQ ID NO: 92 809536 Bet v 4
MADDHPQDKAERERIFKRFDANGDGKISAAELGEALKTLGSITPDEVKHM

MAEIDTDGDGFISFQEFTDFGRANRGLLKDVAKIF

SEQ ID NO: 93 543675 Que a I - Quercus alba =
oak trees (fragment)
GVFTXESQETSVIAPAXLFKALFL SEQ ID NO: 94 543509 Car b I - Carpinus betulus =
hornbeam trees (fragment)
GVFNYEAETPSVIPAARLFKSYVLDGDKLIPKVAPQAIXK SEQ ID NO: 95 543491 Aln g I - Alnus glutinosa =
alder trees (fragment)
GVFNYEAETPSVIPAARLFKAFILDGDKLLPKVAPEAVSSVENI SEQ ID NO: 96 1204056 Rubisco
VQCMQVWPPLGLKKFETLSYLPPLSSEQLAKEVDYLLRKNLIPCLEFELE

HGFVYREHNRSPGYYDGRYWTMWKLPMFGCNDSSQVLKELEECKKAYPSA

FIRIIGFDDK

Additional tree allergen sequences (NCBI entrez accession number):
131919; 128193; 585564; 1942360; 2554672; 2392209; 2414158; 1321728; 1321726; 1321724; 1321722; 1321720; 1321718; 1321716; 1321714; 1321712; 3015520; 2935416; 464576; 1705843; 1168701; 1168710; 1168709; 1168708; 1168707; 1168706; 1168705; 1168704; 1168703; 1168702; 1842188; 2564228; 2564226; 2564224; 2564222; 2564220; 2051993; 1813891; 1536889; 534910; 534900; 534898; 1340000; 1339998; 2149808; 66207; 2129477; 1076249; 1076247; 629480; 481805; 81443; 1361968; 1361967; 1361966; 1361965; 1361964; 1361963; 1361962; 1361961; 1361960; 1361959; 320546; 629483; 629482; 629481; 541804; 320545; 81444; 541814; 629484; 474911; 452742; 1834387; 298737; 298736; 1584322; 1584321; 584320; 1542873; 1542871; 1542869; 1542867; 1542865; 1542863; 1542861; 1542859; 1542857; 1483232; 1483230; 1483228; 558561; 551640; 488605; 452746; 452744; 452740; 452738; 452736; 452734; 452732; 452730; 452728; 450885; 17938; 17927; 17925; 17921; 297538; 510951; 289331; 289329; 166953.

Cedar Sequences

SEQ ID NO: 97 493634 Cry j IB precursor
MDSPCLVALLVFSFVIGSCFSDNPIDSCWRGDSNWAQNRMKLADCAVGFG

SSTMGGKGGDLYTVTNSDDDPVNPPGTLRYGATRDRPLWIIFSGNMNIKL

KMPMYIAGYKTFDGRGAQVYIGNGGPCVFIKRVSNVIHGLYLYGCSTSVL

GNVLINESFGVEPVHPQDGDALTLRTATNIWIDHNSFSNSSDGLVDVTLT

STGVTISNNLFFNHHKVMSLGHDDAYSDDKSMKVTVAFNQFGPNCGQRMP

RARYGLVHVANNNYDPWTIYAIGGSSNPTILSEGNSFTAPNESYKKQVTI

RIGCKTSSSCSNWVWQSTQDVFYNGAYFVSSGKYEGGNIYTKKEAFNVEN

GNATPHLTQNAGVLTCSLSKRC

SEQ ID NO: 98 493632 Cry j IA precursor
MDSPCLVALLVLSFVIGSCFSDNPIDSCWRGDSNWAQNRMKLADCAVGFG

SSTMGGKGGDLYTVTNSDDDPVNPAPGTLRYGATRDRPLWIIFSGNMNIK

LKMPMYIAGYKTFDGRGAQVYIGNGGPCVFIKRVSNVIIHGLHLYGCSTS

VLGNVLINESFGVEPVHPQDGDALTLRTATNIWIDHNSFSNSSDGLVDVT

LSSTGVTISNNLFFNHHKVMLLGHDDAYSDDKSMKVTVAFNQFGPNCGQR

NPRARYGLVHVANNNYDPWTIYAIGGSSNPTILSEGNSFTAPNESYKKQV

TIRIGCKTSSSCSNWVWQSTQDVFYNGAYFVSSGKYEGGNIYTKKEAFNV

ENGNATPQLTKNAGVLTCSLSKRC

SEQ ID NO: 99 1076242 Cry j II precursor -
Japanese cedar
MAMKLIAPMAFLAMQLIIMAAAEDQSAQIMLDSVVEKYLRSNRSLRKVEH

SRHDAINIFNVEKYGAVGDGKHDCTEAFSTAWQAACKNPSAMLLVPGSKK

FVVNNLFFNGPCQPHFTFKVDGIIAAYQNPASWKNNRIWLQFAKLTGFTL

MGKGVIDGQGKQWWAGQCKWVNGREICNDRDRPTAIKFDFSTGLIIQGLK

LMNSPEFHLVFGNCEGVKIIGISITAPRDSPNTDGIDIFASKNFHLQKNT

IGTGDDCVAIGTGSSNIVEEDLICGPGHGISIGSLGRENSRAEVSYVHVN

GAKFIDTQNGLRIKTWQGGSGMASHIIYENVEMINSENPILINQFYCTSA

SACQNQRSAVQIQDVTYKNIRGTSATAAAIQLKCSDSMPCKDIKLSDISL

KLTSGKIASCLNDNANGYFSGHVIPACKNLSPSAKRKESKSHKHPKTVMV

ENMRAYDKGNRTRILLGSRPPNCTNKCHGCSPCKAKLVIVHRIMPQEYYP

QRWICSCHGKIYHP

SEQ ID NO: 100 1076241 Cry j II protein -
Japanese cedar
MAMKFIAPMAFVAMQLIIMAAAEDQSAQIMLDSDIEQYLRSNRSLRKVEH

SRHDAINIFNVEKYGAVGDGKHDCTEAFSTAWQAACKKPSAMLLVPGNKK

FVVNNLFFNGPCQPHFTFKVDGIIAAYQNPASWKNNRIWLQFAKLTGFTL

-continued

MGKGVIDGQGKQWWAGQCKWVNGREICNDRDRPTAIKFDFSTGLIIQGLK

LMNSPEFHLVFGNCEGVKIIGISITAPRDSPNTDGIDIFASKNFHLQKNT

IGTGDDCVAIGTGSSNIVIEDLICGPGHGISIGSLGRENSRAEVSYVHVN

GAKFIDTQNGLRIKTWQGGSGMASHIIYENVEMINSENPILINQFYCTSA

SACQNQRSAVQIQDVTYKNIRGTSATAAAIQLKCSDSMPCKDIKLSDISL

KLTSGKIASCLNDNANGYFSGHVIPACKNLSPSAKRKESKSHKHPKTVMV

KNMGAYDKGNRTRILLGSRPPNCTNKCHGCSPCKAKLVIVHRIMPQEYYP

QRWMCSREGKIYHP

SEQ ID NO: 101 541803 Cry j I precursor -
Japanese cedar
MDSPCLVALLVLSFVIGSCFSDNPIDSCWRGDSNWAQNRMKLADCAVGFG

SSTMGGKGGDLYTVTNSDDDPVNPPGTLRYGATRDRPLWIIFSGNMNIKL

KMPMYIAGYKTFDGRGAQVYIGNGGPCVFIKRVSNVIIHGLHLYGCSTSV

LGNVLINESFGVEPVHPQDGDALTLRTATNIWIDHNSFSNSSDGLVDVTL

SSTGVTISNNLFFNHHKVMLLGHDDAYSDDKSMKVTVAFNQFGPNCGQRM

PRARYGLVHVANNNYDPWTIYAIGGSSNPTILSEGNSFTAPNESYKKQVT

IRIGCKTSSSCSNWVWQSTQDVFYNGAYFVSSGKYEGGNIYTKKEAFNVE

NGNATPQLTKNAGVLTCSLSKRC

SEQ ID NO: 102 541802 Cry j I precursor -
Japanese cedar
MDSPCLVALLVFSFVIGSCFSDNPIDSCWRGDSNWAQNRMKLADCAVGFG

SSTMGGKGGDLYTVTNSDDDPVNPAPGTLRYGATRDRPLWIIFSGNMNIK

LKMPMYIAGYKTFDGRGAQVYIGNGGPCVFIKRVSNVIIHGLYLYGCSTS

VLGNVLINESFGVEPVHPQDGDALTLRTATNIWIDHNSFSNSSDGLVDVT

LTSTGVTISNNLFFNHHKVMSLGHDDAYSDDKSMKVTVAFNQFGPNCGQR

MPRARYGLVHVANNNYDPWTIYAIGGSSNPTILSEGNSFTAPNESYKKQV

TIRIGCKTSSSCSNWVWQSTQDVFYNGAYFVSSGKYEGGNIYTKKEAFNV

ENGNATPHLTQNAGVLTCSLSKRC

Delivery Methods

Once formulated the compositions of the invention can be delivered to a subject in vivo using a variety of known routes and techniques. For example, a composition can be provided as an injectable solution, suspension or emulsion and administered via parenteral, subcutaneous, epidermal, intradermal, intramuscular, intraarterial, intraperitoneal, intravenous injection using a conventional needle and syringe, or using a liquid jet injection system, or using a patch. Compositions can also be administered topically to skin or mucosal tissue, such as nasally, intratracheally, intestinal, rectally or vaginally, or provided as a finely divided spray suitable for respiratory or pulmonary administration. Other modes of administration include oral administration, suppositories, sublingual administration, and active or passive transdermal delivery techniques.

Where a peptide of the invention is to be administered, it is preferred to administer the peptide to a site in the body where it will have the ability to contact suitable antigen presenting cells, and where it, or they, will have the opportunity to contact T cells of the individual. Where an APC is to be administered, it is preferred to administer the APC to a site in the body where it will have the ability to contact, and activate, suitable T cells of the individual.

Delivery Regimes

Administration of the peptides/polynucleotides/cells (such as the composition containing a plurality of peptides) may be by any suitable method as described above. Suitable amounts of the peptide may be determined empirically, but typically are in the range given below. A single administration of each peptide may be sufficient to have a beneficial effect for the patient, but it will be appreciated that it may be beneficial if the peptide is administered more than once, in which case typical administration regimes may be, for example, once or twice a week for 2-4 weeks every 6 months, or once a day for a week every four to six months. As will be appreciated, each peptide or polynucleotide, or combination of peptides and/or polynucleotides may be administered to a patient singly or in combination.

Dosages for administration will depend upon a number of factors including the nature of the composition, the route of administration and the schedule and timing of the administration regime. Suitable doses of a molecule of the invention may be in the order of up to 15 µg, up to 20 µg, up to 25 µg, up to 30 µg, up to 50 µg, up to 100 µg, up to 500 µg or more per administration. Suitable doses may be less than 15 µg, but at least 1 ng, or at least 2 ng, or at least 5 ng, or at least 50 ng, or at least 100 ng, or at least 500 ng, or at least 1 µg, or at least 10 µg. For some molecules of the invention, the dose used may be higher, for example, up to 1 mg, up to 2 mg, up to 3 mg, up to 4 mg, up to 5 mg or higher. Such doses may be provided in a liquid formulation, at a concentration suitable to allow an appropriate volume for administration by the selected route.

Kits

The invention also relates to a combination of components described herein suitable for use in a treatment of the invention which are packaged in the form of a kit in a container. Such kits may comprise a series of components to allow for a treatment of the invention. For example, a kit may comprise one or more different peptides, polynucleotides and/or cells of the invention, or one or more peptides, polynucleotides or cells of the invention and one or more additional therapeutic agents suitable for simultaneous administration, or for sequential or separate administration. The kit may optionally contain other suitable reagent(s) or instructions and the like.

The invention is illustrated by the following Examples:

EXAMPLE 1

MHC Class II Binding Search

The aim of this study is to identify a distinct panel of peptides with strong affinities for the eight most common human MHC Class II HLA-DRB1* allotypes. In order to identify binding peptides in the major birch allergens Bet v1, Bet v2, Bet v3, Bet v4, Bet v6, an in silico approach was carried out using the commercially available EpiMatrix algorithm (EpiVax Inc.) This is a bioinformatic analysis of peptides from a sequence for the potential to be accommodated within the binding groove of MHC class II HLA-DR molecules.

EpiMatrix is a matrix-based algorithm that ranks 9 amino acid residue sequences, overlapping by 8 amino acids, from any polypeptide sequence by estimated probability of binding to each of the selected MHC molecules. (De Groot et al., AIDS Research and Human Retroviruses 13:539-41 (1997). The procedure for developing matrix motifs was published by Schafer et al, Vaccine 16:1880-4 (1998). In this Example, binding potential for HLA DR1, DR3, DR4, DR7, DR8, DR11, DR13 and DR15 is assessed. Putative MHC ligands are selected by scoring each 9-mer frame in a protein sequence. This score is derived by comparing the sequence of the 9-mer to the matrix of amino acid sequences known to bind to each MHC allele. Retrospective studies have demonstrated that EpiMatrix accurately predicts published MHC ligands (Jesdale et al., in Vaccines '97 (Cold Spring Harbor Press, Cold Spring Harbor, N.Y., 1997)). Successful Prediction of peptides which bind to multiple MHC molecules has also been confirmed.

The EpiMatrix data for each allergen is shown either:

As overlapping 9 mer peptide data with the binding (Z) score for each allele and the number of 'hits' for the eight alleles (Z scores of equal to or greater than the top 5% of predicted binders): or As a cluster report where the data from analysing multiple sequences from the database is 'clustered' to give an overview of binding for all variants of the protein. The "EpiMatrix hits" refers to the number of high predicted Z binding scores for the to eight alleles within that sequence whilst the "EpiMatrix Cluster Score" is derived from the number of hits normalized for the length of the cluster. Cluster Score is thus the excess or shortfall in predicted aggregate MHC binding properties relative to a random peptide standard. A cluster score above 10 is considered to indicate broad MHC binding properties.

EpiMatrix analyses were performed on the entire sequences of known isoforms of Bet v1, listed below with their corresponding NCBI accession numbers:

| Bet v1 L | P43185; |
| Bet v1 M/N | P43186; |
| Bet v1 K | P43184; |
| Bet v1 J | P43183; |
| Bet v1 G | P43180; |
| Bet v1 F/I | P43179; |
| Bet v1 E | P43178; |
| Bet v1 D/H | P43177; |
| Bet v1 C | P43176; |
| Bet v1 B | P45431; |
| Bet v1 A | P15494; |

Epimatrix analyses were also performed on additional known Bet v1 sequences indexed by accession number in Table 2.

These analyses identified core peptides (and their flanking sequences) derived from the above sequences which are predicted to have good MHC class-II binding. These sequences are shown below in Tables 1 and 2. As shown, many of the peptides identified are highly conserved between different Bet v1 isoforms.

In Tables 1 and 2:

"Residues in main sequence" gives the location of the peptide within the sequences that were analysed. The core peptide (underscored middle amino acids in bold) defines the actual binding sequence that was identified during the analysis. The stabilizing flanks (N-terminal and C-terminal, not bold) were included for use with the core sequence and are typically required to aid manufacture of the peptides. "Number of hits" refers to the number of high predicted binding affinities for all MHC types tested within the sequence. The "EpiMatrix Cluster Score" is derived from the number of hits normalized for the length of the cluster. Cluster Score is thus the excess or shortfall in predicted aggregate MHC binding properties relative to a random peptide standard. A score above 10 is considered to indicate broad MHC binding properties.

TABLE 1

Bet v1

| INPUT SEQUENCE | RESIDUE IN SEQUENCE (Incl. FLANKS) | SEQUENCE | Hydrophobicity | EpiMatrix HITS (Excl FLANKS) | EpiMatrix CLUSTER SCORE (Excl FLANKS) | Peptide ID NO | SEQ ID NO: |
|---|---|---|---|---|---|---|---|
| P43185 | 13-28 | VIPAARMFKAFILDGD | 0.78 | 6 | 11.3 | P1 | 1 |
| P15494 | 100-114 | SNEIKIVATPDGGSI | 0.03 | 7 | 15.57 | P2 | 2 |
| P43176 | 100-114 | CNEIKIVATPDGGSI | 0.25 | 7 | 15.57 | P3 | 3 |
| P43177 | 100-114 | SNEIKIVATPDGGCV | 0.23 | 7 | 15.57 | P4 | 4 |
| P43178 | 100-116 | SNEIKIVATPNGGSILK | 0.02 | 10 | 20.13 | P5 | 5 |
| P43179 | 100-116 | SNEIKIVATPNGGSILK | 0.02 | 10 | 20.13 | P6 | 5 |
| P43180 | 100-114 | SNEIKIVATPDGGCV | 0.23 | 7 | 15.57 | P7 | 4 |
| P43183 | 100-116 | SNEIKIVATPNGGSILK | 0.02 | 10 | 20.13 | P8 | 5 |
| P43184 | 100-114 | CNEIKIVATPDGGSI | 0.25 | 7 | 15.57 | P9 | 3 |
| P43185 | 100-114 | SNEIKIVATPDGGCV | 0.23 | 7 | 15.57 | P10 | 4 |
| P43186 | 100-114 | CNEIKIVATPDGGSI | 0.25 | 7 | 15.57 | P11 | 3 |
| P45431 | 100-114 | CNEIKIVATPDGGSI | 0.25 | 7 | 15.57 | P12 | 3 |
| P43178 | 112-126 | GSILKINNKYHTKGD | -1.08 | 6 | 12.34 | P13 | 65 |
| P43179 | 112-126 | GSILKINNKYHTKGD | -1.08 | 6 | 12.34 | P14 | 65 |
| P43183 | 112-126 | GSILKINNKYHTKGD | -1.08 | 6 | 12.34 | P15 | 65 |
| P15494 | 142-160 | ETLLRAVESYLLAHSDAYN | -0.09 | 8 | 12.06 | P16 | 6 |

TABLE 1-continued

Bet v1

| INPUT SEQUENCE | RESIDUE IN SEQUENCE (Incl. FLANKS) | SEQUENCE | Hydrophobicity | EpiMatrix HITS (Excl FLANKS) | EpiMatrix CLUSTER SCORE (Excl FLANKS) | Peptide ID | SEQ ID NO: |
|---|---|---|---|---|---|---|---|
| P43176 | 142-160 | EALLRAVESYLLAHSDAYN | 0.04 | 8 | 12.06 | P17 | 7 |
| P43177 | 142-160 | ETLLRAVESYLLAHSDAYN | -0.09 | 8 | 12.06 | P18 | 6 |
| P43178 | 142-160 | ETLLRAVESYLLAHSDAYN | -0.09 | 8 | 12.06 | P19 | 6 |
| P43179 | 142-160 | ETLLRAVESYLLAHSDAYN | -0.09 | 8 | 12.06 | P20 | 6 |
| P43180 | 142-160 | ETLLRAVESYLLAHSDAYN | -0.09 | 8 | 12.06 | P21 | 6 |
| P43183 | 142-160 | ETLLRAVESYLLAHSDAYN | -0.09 | 8 | 12.06 | P22 | 6 |
| P43184 | 142-160 | EALLRAVESYLLAHSDAYN | 0.04 | 8 | 12.06 | P23 | 7 |
| P43185 | 142-160 | ETLLRAVESYLLAHSDAYN | -0.09 | 8 | 12.06 | P24 | 6 |
| P43186 | 142-160 | EALLRAVESYLLAHSDAYN | 0.04 | 8 | 12.06 | P25 | 7 |
| P45431 | 142-160 | EALLRAVESYLLAHSDAYN | 0.04 | 8 | 12.06 | P26 | 7 |

TABLE 1A

EpiMatrix analysis of Bet v1 Sequence: P15494: predicted multiple HLA DR allele binding region: SEQ ID NO: 141 FNYETETTSVIPAARLFKAFILDGDNLF (4-31).

| Frame Start | AA Sequence | Frame Stop | DRB1*0101 Z-Score | DRB1*0301 Z-Score | DRB1*0401 Z-Score | DRB1*0701 Z-Score | DRB1*0801 Z-Score | DRB1*1101 Z-Score | DRB1*1301 Z-Score | DRB1*1501 Z-Score | Hits | SEQ ID NO: |
|---|---|---|---|---|---|---|---|---|---|---|---|---|
| 4 | FNYETETTS | 12 | .96 | 1.29 | 1.58 | -.42 | .10 | .93 | -.21 | .27 | 0 | 142 |
| 5 | NYETETTSV | 13 | .32 | -.86 | .59 | .81 | -1.32 | -.80 | -.75 | .22 | 0 | 143 |
| 6 | YETETTSVI | 14 | 2.15 | 1.37 | 2.25 | 1.72 | 1.09 | 1.15 | -.03 | .70 | 3 | 144 |
| 7 | ETETTSVIP | 15 | -.11 | -1.34 | .48 | .58 | -.89 | -.60 | -.84 | -.03 | 0 | 145 |
| 8 | TETTSVIPA | 16 | .16 | -1.10 | .97 | .51 | -.86 | -.69 | -.48 | .04 | 0 | 146 |
| 9 | ETTSVIPAA | 17 | -.04 | .16 | .64 | -.18 | -.89 | .43 | -.39 | -.17 | 0 | 147 |
| 10 | TTSVIPAAR | 18 | .64 | .66 | -.12 | -.56 | .14 | .47 | .50 | -.43 | 0 | 148 |
| 11 | TSVIPAARL | 19 | 1.52 | -.44 | .23 | .47 | -.63 | .28 | -.96 | -.33 | 0 | 149 |
| 12 | SVIPAARLF | 20 | .69 | -.06 | -.07 | 1.07 | -.44 | .25 | 1.05 | -.20 | 0 | 150 |
| 13 | VIPAARLFK | 21 | .67 | 2.00 | .65 | .50 | 1.21 | 1.32 | 1.98 | 1.21 | 2 | 151 |
| 14 | IPAARLFKA | 22 | .55 | 1.17 | .00 | -.28 | .32 | .16 | 1.27 | 1.60 | 0 | 152 |
| 15 | PAARLFKAF | 23 | -1.29 | -1.65 | -1.57 | .28 | -.29 | -.88 | -.32 | -.58 | 0 | 153 |
| 16 | AARLFKAFI | 24 | 1.13 | 1.39 | -.25 | -.68 | 1.25 | 1.50 | 1.32 | -.06 | 0 | 154 |
| 17 | ARLFKAFIL | 25 | 2.12 | .89 | .25 | 1.84 | 1.11 | .18 | 1.54 |  | 3 | 155 |
| 18 | RLFKAFILD | 26 | -1.54 | -.90 | -1.35 | -.86 | 1.38 | -1.29 | -.38 | -.67 | 0 | 156 |
| 19 | LFKAFILDG | 27 | .86 | 1.13 | 1.48 | .68 | .94 | .39 | 1.14 | 1.37 | 0 | 157 |
| 20 | FKAFILDGD | 28 | -.17 | .58 | .09 | -.43 | 1.90 | .24 | .30 | .96 | 1 | 158 |
| 21 | KAFILDGDN | 29 | -.49 | -1.35 | -.67 | -.69 | -.59 | -.02 | -2.05 | .29 | 0 | 159 |
| 22 | AFILDGDNL | 30 | 1.32 | -.28 | -.21 | .67 | -.85 | -.69 | -.80 | .30 | 0 | 160 |
| 23 | FILDGDNLF | 31 | -.02 | 2.27 | 1.73 | 1.07 | .47 | -.09 | -.22 | .74 | 2 | 161 |

TABLE 2

Bet v 1

| INPUT SEQUENCE | RESIDUES IN SEQUENCE (Incl. FLANKS) | SEQUENCE | Hydrophobicity | EpiMatrix HITS (Excl FLANKS) | EpiMatrix CLUSTER SCORE (Excl FLANKS) | Peptide ID NO | SEQ ID NO: |
|---|---|---|---|---|---|---|---|
| CAA04829 | 1-16 | GVFNYEIGATSVIPAA | 0.84 | 7 | 11.23 | P27 | 8 |
| 2122374C | 14-34 | IAPARLFKSFVLDADNLIPKV | 0.62 | 9 | 13.67 | P28 | 9 |
| ABC41588 | 97-111 | CNEIKLVATPDGGST | -0.15 | 7 | 15.45 | P29 | 10 |
| ABC41605 | 97-111 | SKEIKIAAAPDGGSI | 0.01 | 6 | 13.05 | P30 | 11 |
| ABC41615 | 97-111 | SNEIKIVATPDGGCI | 0.25 | 7 | 15.57 | P31 | 12 |
| ABC41617 | 97-111 | CNEIKLVATPDGGSI | 0.20 | 7 | 15.45 | P32 | 13 |
| ABC41596 | 97-113 | CNEIKIVAAPGGGSILK | 0.54 | 9 | 17.42 | P33 | 14 |
| ABC41602 | 97-113 | CNEIKIVPAPGGGSILK | 0.34 | 9 | 16.98 | P34 | 15 |
| ABC41609 | 97-113 | SYEIKIVAAPGGGSILK | 0.48 | 9 | 17.42 | P35 | 16 |
| 1QMR_A | 99-113 | SNEIKIVATGDGGSI | 0.11 | 5 | 10.32 | P36 | 17 |
| CAA96546 | 100-114 | CNEIKIVAAPDGGSI | 0.41 | 7 | 14.59 | P37 | 18 |
| CAA96547 | 100-114 | SNEIKIVATPDGRSI | -0.25 | 7 | 15.57 | P38 | 19 |
| CAA07324 | 100-114 | SNEIKLVATPDGGSI | -0.02 | 7 | 15.45 | P39 | 20 |
| CAA07327 | 100-114 | CNEIKIVATPDGGCV | 0.45 | 7 | 15.57 | P40 | 21 |
| CAA07318 | 100-114 | SNEIKIVTTPDGGCV | 0.06 | 7 | 15.57 | P41 | 22 |
| AAD26561 | 100-114 | SNEIKIVATPDGGPI | -0.03 | 7 | 15.57 | P42 | 23 |
| ABC41589 | 109-125 | GSILKIRNKYHTKGDHE | -1.41 | 9 | 15.34 | P43 | 24 |
| ABC41609 | 139-150 | AGLFKAVENYLV | 0.82 | 5 | 10.95 | P44 | 25 |
| ABC41583 | 139-150 | ETLLRAVESYLL | 0.58 | 6 | 13.44 | P45 | 26 |
| ABC41589 | 139-150 | EALLRAVESYLL | 0.78 | 6 | 13.44 | P46 | 27 |
| ABC41602 | 139-150 | EALFRAVESYLL | 0.70 | 7 | 16.84 | P47 | 28 |
| CAA96544 | 139-156 | EKAVGLLKAVESYLLAHS | 0.43 | 7 | 12.67 | P48 | 29 |
| CAA07319 | 141-160 | GETLLRAVEGYLLAHSDAYN | -0.09 | 8 | 11.13 | P49 | 30 |
| AAD26561 | 142-156 | ETLLRAVESYPLAHS | -0.05 | 6 | 13.44 | P50 | 31 |
| 2122374C | 142-160 | AGLFKAVENYLVAHPNAYN | 0.02 | 10 | 15.5 | P51 | 32 |
| CAA96539 | 142-160 | ETLLRAVERYLLAHSDAYN | -0.29 | 10 | 18.69 | P52 | 33 |
| 2122374A | 142-160 | EALFRAVESYLLAHSDAYN | -0.02 | 9 | 15.46 | P53 | 34 |

EXAMPLE 2

EpiMatrix analyses as above were performed on the entire sequence of a known isoform of Bet v 3 (NCBI accession no: P43187). These analyses identified a core peptide (and its flanking sequence) derived from the above sequence which is predicted to have good MHC class-II binding. The sequence is shown below in Table 3. Headings and notes for Table 3 are as with Table 1 above.

TABLE 3

Bet v 3

| INPUT SEQUENCE | RESIDUES IN SEQUENCE (Incl. FLANKS) | SEQUENCE | Hydrophobicity | EpiMatrix HITS (Excl FLANKS) | EpiMatrix CLUSTER SCORE (Excl FLANKS) | Peptide ID NO | SEQ ID NO: |
|---|---|---|---|---|---|---|---|
| P43187 | 188-205 | VDFFEFKDMMRSVLVRSS | 0.16 | 10 | 14.02 | P54 | 35 |

A sequence at residues 80 to 94 of P43187, TVKSFTREG-NIGLQF (Peptide ID NO. P55, SEQ ID NO: 36), was also predicted to have good MHC-Class II binding. Additional in silico analysis of other birch allergen sequences from Bet v 3 is shown here:

TABLE 3A

EpiMatrix analysis of Bet v3 Sequence: GI1168696_SPP43187: predicted multiple HLA DR allele binding region SEQ ID NO: 77 SLNTLRLRRIFDLFDK (35-50).

| Frame start | sequence | end | DRB1*0101 Z-Score | DRB1*0301 Z-Score | DRB1*0401 Z-Score | DRB1*0701 Z-Score | DRB1*0801 Z-Score | DRB1*1101 Z-Score | DRB1*1301 Z-Score | DRB1*1501 Z-Score | Hits | SEQ ID NO: |
|---|---|---|---|---|---|---|---|---|---|---|---|---|
| 35 | SLNTLRLRR | 43 | .28 | .97 | -.38 | .38 | .64 | .53 | 1.73 | .68 | 1 | 103 |
| 36 | LNTLRLRRI | 44 | 1.30 | .87 | -.15 | .46 | .82 | 1.35 | 1.41 | .17 | 0 | 104 |
| 37 | NTLRLRRIF | 45 | -.24 | .12 | -1.52 | .43 | 1.21 | 1.13 | 1.42 | -.47 | 0 | 105 |
| 38 | TLRLRRIFD | 46 | .47 | .40 | -.46 | .42 |  | .66 | .49 | -.34 | 1 | 106 |
| 39 | LRLRRIFDL | 47 | 1.09 | .83 | .08 |  | 1.68 | .31 | 1.94 |  | 4 | 107 |
| 40 | RLRRIFDLF | 48 | -1.83 | -.86 | -1.40 | -.38 | -.94 | -1.34 | -.63 | -.87 | 0 | 108 |
| 41 | LRRIFDLFD | 49 | .84 | .60 | 1.39 | .46 | 1.41 | .88 | .39 | 1.55 | 0 | 109 |
| 42 | RRIFDLFDK | 50 | -.31 | .38 | -.31 | -.58 | .85 | .33 | 1.05 | 1.61 | 0 | 110 |

EXAMPLE 3

EpiMatrix analyses as above were performed on the entire sequence of known isoforms of Bet v 4 (NCBI accession nos: Q39419, CAA73147). These analyses identified core peptides (and their flanking sequences) derived from the above sequences which are predicted to have good MHC class-II binding. These sequences are shown below in Table 4. Headings and notes for Table 4 are as with Table 1 above.

TABLE 4

Bet v 4

| INPUT SEQUENCE | RESIDUES IN SEQUENCE (Incl. FLANKS) | SEQUENCE | Hydrophobicity | EpiMatrix HITS (Excl FLANKS) | EpiMatrix CLUSTER SCORE (Excl FLANKS) | Peptide ID NO | SEQ ID NO: |
|---|---|---|---|---|---|---|---|
| Q39419 | 10-27 | AERERIFKRFDANGDGKI | -1.19 | 8 | 13.83 | P56 | 37 |
| Q39419 | 67-81 | FTDFGRANRGLLKDV | -0.38 | 7 | 13.49 | P57 | 38 |
| CAA73147 | 67-81 | FTDFARANRGLLKDV | -0.23 | 7 | 13.53 | P58 | 39 |

EXAMPLE 4

EpiMatrix analyses as above were performed on the entire sequence of a known isoform of Bet v 6 (NCBI accession no: 065002). These analyses identified core peptides (and their flanking sequences) derived from the above sequences which are predicted to have good MHC class-II binding. These sequences are shown below in Table 5. Headings and notes for Table 5 are as with Table 1 above.

TABLE 5

Bet v 6

| INPUT SEQUENCE | RESIDUES IN SEQUENCE (Incl. FLANKS) | SEQUENCE | Hydrophobicity | EpiMatrix HITS (Excl FLANKS) | EpiMatrix CLUSTER SCORE (Excl FLANKS) | Peptide ID NO | SEQ ID NO: |
|---|---|---|---|---|---|---|---|
| 065002 | 43-63 | PVKGRLVEKFKGLGVTLLHGD | 0.04 | 9 | 14.09 | P59 | 40 |
| 065002 | 67-90 | HESLVKAFKQVDVVISTVGHLQLA | 0.52 | 11 | 15.54 | P60 | 41 |
| 065002 | 149-170 | YVSSNFFAGYFLPTLAQPGLTS | 0.46 | 10 | 12.92 | P61 | 42 |
| 065002 | 258-274 | PINVILAINHSVFVKGD | 0.83 | 7 | 10.54 | P62 | 43 |

EXAMPLE 5

EpiMatrix analyses as above were performed on the entire sequence of a known isoform of Bet v 7 (NCBI accession no: CAC84116). These analyses identified a core peptide (and its flanking sequence) derived from the above sequence which is predicted to have good MHC class-II binding. This sequence is shown below in Table 6. Headings and notes for Table 6 are as with Table 1 above.

TABLE 6

Bet v 7

| INPUT SEQUENCE | RESIDUES IN SEQUENCE (Incl. FLANKS) | SEQUENCE | Hydrophobicity | EpiMatrix HITS (Excl. FLANKS) | EpiMatrix CLUSTER SCORE (Excl FLANKS) | Peptide ID NO | SEQ ID NO: |
|---|---|---|---|---|---|---|---|
| CAC84116 | 34-48 | AENFRALCTGEKGNG | -0.77 | 5 | 10.46 | P63 | 44 |

EXAMPLE 5A

Additional in silico analysis of other birch allergen sequences from Bet v 2 is shown here:

TABLE 6A

EpiMatrix analysis of Bet v2 Sequence: GI1942360_PDB1CQA: predicted multiple HLA DR allele binding region: SEQ ID NO: 111 SVWAQSSSFPQFKPQEITGIMK (33-54).

| Frame start | sequence | end | DRB1*0101 Z-Score | DRB1*0301 Z-Score | DRB1*0401 Z-Score | DRB1*0701 Z-Score | DRB1*0801 Z-Score | DRB1*1101 Z-Score | DRB1*1301 Z-Score | DRB1*1501 Z-Score | Hits | SEQ ID NO: |
|---|---|---|---|---|---|---|---|---|---|---|---|---|
| 33 | SVWAQSSSF | 41 | .75 | .40 | 1.04 | 1.19 | -.29 | -.22 | -.17 | .71 | 0 | 112 |
| 34 | VWAQSSSFP | 42 | .90 | .82 | 1.31 | .46 | -.02 | .21 | .64 | 1.01 | 0 | 113 |
| 35 | WAQSSSFPQ | 43 | 1.70 | .36 | 2.24 |  | 1.23 | 1.44 | .12 | 1.53 | 3 | 114 |
| 36 | AQSSSFPQF | 44 | -.65 | .38 | -.28 | -.01 | -1.26 | -.18 | -.18 | -.56 | 0 | 115 |
| 37 | QSSSFPQFK | 45 | -.31 | .01 | .24 | .04 | -1.01 | .00 | -1.52 | -.51 | 0 | 116 |

TABLE 6A-continued

EpiMatrix analysis of Bet v2 Sequence: GI1942360_PDB1CQA: predicted multiple
HLA DR allele binding region: SEQ ID NO: 111 SVWAQSSSFPQFKPQEITGIMK (33-54).

| Frame start | sequence | end | DRB1*0101 Z-Score | DRB1*0301 Z-Score | DRB1*0401 Z-Score | DRB1*0701 Z-Score | DRB1*0801 Z-Score | DRB1*1101 Z-Score | DRB1*1301 Z-Score | DRB1*1501 Z-Score | Hits | SEQ ID NO: |
|---|---|---|---|---|---|---|---|---|---|---|---|---|
| 38 | SSSFPQFKP | 46 | -.45 | -.73 | -1.50 | -1.02 | -.04 | -.76 | -.02 | .21 | 0 | 117 |
| 39 | SSFPQFKPQ | 47 | -1.10 | -2.37 | -.57 | .24 | -.52 | -.64 | -1.22 | -.98 | 0 | 118 |
| 40 | SFPQFKPQE | 48 | -.23 | 1.11 | -.75 | -1.69 | 1.34 | .47 | 1.32 | -.32 | 0 | 119 |
| 41 | FPQFKPQEI | 49 | 1.55 | .73 | .67 | .99 | .88 | .49 | .09 | 2.02 | 1 | 120 |
| 42 | PQFKPQEIT | 50 | -.26 | .27 | -.85 | .12 | 1.00 | .28 | .59 | -.60 | 0 | 121 |
| 43 | QFKPQEITG | 51 | -1.28 | -.42 | -.84 | -.60 | -.27 | -1.13 | .23 | .00 | 0 | 122 |
| 44 | FKPQEITGI | 52 | 1.94 | 1.68 | 1.69 | 1.76 | .07 | .45 | 1.37 | 1.43 | 4 | 123 |
| 45 | KPQEITGIM | 53 | .15 | .15 | .32 | .12 | -.39 | .10 | -1.15 | -.26 | 0 | 124 |
| 46 | PQEITGIMK | 54 | -.06 | -1.11 | -.06 | -.24 | -1.55 | -.85 | -1.48 | -.15 | 0 | 125 |

TABLE 6B

EpiMatrix analysis of Bet v2 Sequence: GI1942360_PDB1CQA: predicted multiple
HLA DR allele binding region: SEQ ID NO: 126 IKYMVIQGEAGAVIRGKKGSGG (72-93).

| Frame start | sequence | end | DRB1*0101 Z-Score | DRB1*0301 Z-Score | DRB1*0401 Z-Score | DRB1*0701 Z-Score | DRB1*0801 Z-Score | DRB1*1101 Z-Score | DRB1*1301 Z-Score | DRB1*1501 Z-Score | Hits | SEQ ID NO: |
|---|---|---|---|---|---|---|---|---|---|---|---|---|
| 72 | IKYMVIQGE | 80 | 1.21 | 1.60 | 1.25 | .49 | 1.87 | 1.30 | -.52 | .97 | 1 | 127 |
| 73 | KYMVIQGEA | 81 | .45 | .63 | -.35 | .37 | .56 | 1.73 | .28 | .53 | 1 | 128 |
| 74 | YMVIQGEAG | 82 | 1.68 | .22 | 1.47 | .98 | .61 | 1.06 | -.37 | .26 | 1 | 129 |
| 75 | MVIQGEAGA | 83 | 1.49 | 2.23 | 1.51 | -.42 | 1.07 | 1.87 | 2.27 | .85 | 3 | 130 |
| 76 | VIQGEAGAV | 84 | 1.12 | 1.46 | -.18 | 1.12 | -.11 | .16 | -.07 | 2.02 | 1 | 131 |
| 77 | IQGEAGAVI | 85 |  | 1.64 | 1.28 | .54 | .46 | .67 | .50 | .86 | 1 | 132 |
| 78 | QGEAGAVIR | 86 | .56 | .61 | -.43 | -.01 | -.68 | -1.08 | .29 | .12 | 0 | 133 |
| 79 | GEAGAVIRG | 87 | .02 | .36 | .41 | -.45 | -.52 | -1.38 | -.79 | .28 | 0 | 134 |
| 80 | EAGAVIRGK | 88 | -.12 | -.55 | .17 | -.08 | -.44 | .08 | -.23 | -1.21 | 0 | 135 |
| 81 | AGAVIRGKK | 89 | -.65 | .95 | -1.14 | .00 | .75 | 1.71 | .58 | .53 | 1 | 136 |
| 82 | GAVIRGKKG | 90 | .82 | -1.39 | -.20 | -.20 | -.70 | -.26 | -1.31 | .08 | 0 | 137 |
| 83 | AVIRGKKGS | 91 | -.08 | .16 | -.55 | -.21 | 1.97 | 1.49 | 1.43 | 1.07 | 1 | 138 |
| 84 | VIRGKKGSG | 92 | .10 |  | -.64 | -.90 | 1.35 | 1.18 | .92 | 1.79 | 2 | 139 |
| 85 | IRGKKGSGG | 93 | 1.18 | 1.05 | .64 | .02 | 2.09 | .95 | 1.11 | 1.83 | 2 | 140 |

EXAMPLE 6

Based on the analyses performed in Examples 1 to 5A, the following peptides shown in Table 7 were designed for screening in subsequent assays. The design process involved modification of native sequences to enhance solubility and other physicochemical characteristics. For example, for Bir12A, residues in parent 62-77R indicates that the peptide sequence of Bir12A corresponds to residues 62 to 77 of the parent sequence, with an additional R residue added to the C terminus to improve solubility. Similarly, for Bir01F, G, H and I, residues in parent 4-18K indicates that these peptide sequences correspond to residues 4 to 18 of the parent sequence, with an to additional K residue added to the C terminus to improve solubility.

TABLE 7

| Peptide | Sequence | Residues | SEQ. ID. NO |
|---|---|---|---|
| BIR01F | FNYETEATSVIPAARK | 4-18K (P43185) Bet v1 | 45 |

TABLE 7-continued

| Peptide | Sequence | Residues | SEQ. ID. NO |
|---|---|---|---|
| BIR01G | FNYEIEATSVIPAARK | 4-18K (P43179) Bet v1 | 46 |
| BIR01H | FNYEIETTSVIPAARK | 4-18K (P43177) Bet v1 | 47 |
| BIR01I | FNYETETTSVIPAARK | 4-18K (P15494) Bet v1 | 48 |
| BIR02D | PAARMFKAFILDGDKLVPK | 15-33 (P43185) Bet v1 | 49 |
| BIR02E | PAARLFKAFILEGDTLIPK | 15-33 (P43184) Bet v1 | 50 |
| BIR02G | PAARLFKAFILEGDNLIPK | 15-33 (P41380) Bet v1 | 51 |
| BIR02I | PAARMFKAFILD | 15-26 (P41385) Bet v1 | 52 |
| BIR02J | PAARMFKAFILEGDKLVPK | D to E variant of BIR02D | 53 |
| BIR04 | PGTIKKISFPEGFPFKYV | 51-68 (P43185) Bet v1 | 54 |
| BIR05 | SPFKYVKERVDEVDHA | 63-78 (P43186) Bet v1 | 55 |
| BIR05A | FPFKYVKDRVDEVDHT | 63-78 (P43185) Bet v1 | 56 |
| BIR06 | ANFKYSYSMIEGGALGD | 78-94 (P43186) Bet v1 | 57 |
| BIR06B | TNFKYSYSVIEGGPVGD | 78-94 (P43183) Bet v1 | 58 |
| BIR06D | TNFKYNYSVIEGGPIG | 78-93 (P) Bet v1 | 59 |
| BIR07 | SNEIKIVATPDGGSILK | 100-116 Bet v1 | 60 |
| BIR07A | SNEIKIVATPNGGSILK | 100-116 Bet v1 | 61 |
| BIR07B | SNEIKIVATPQGGSILK | 100-116 Bet v1 | 62 |
| BIR07C | SNEIKIVATPEGGSILK | 100-116 Bet v1 | 63 |
| BIR07D | SNEIKIVATPGGGSILK | 100-116 Bet v1 | 64 |
| BIR08 | GSILKINNKYHTKGD | 112-126 Bet v1 | 65 |
| BIR08A | SILKISNKYHTKGD | 113-125 (P43186) Bet v1 | 66 |
| BIR09 | ETLLRAVESYLLAHSDAY | 142-159 Bet v1 | 67 |
| BIR09A | GETLLRAVESYLLAHS | 141-156 Bet v1 | 68 |
| BIR09B | KEMGETLLRAVESYLLAHS | 138-156 Bet v1 | 69 |
| BIR09C | KEKGETLLRAVESYLLAHS | M to K variant of above | 70 |
| BIR10 | GSVWAQSSSFPQFK | 33-45 (P25816) Bet v2 | 71 |
| BIR11 | FPQFKPQEITGIMK | 41-54 (AAB44348) Bet v2 | 72 |
| BIR12A | PTGMFVAGAKYMVIQGR | 62-77R (P35079) Phl p12 | 73 |
| BIR12B | AKYMVIQGEPGRVIRGK | 70-86 (P35079) Phl p12 | 74 |
| BIR13 | GIKYMVIQGEAGAVIRGK | 71-88 (AAB44348) Bet v2 | 75 |
| BIR14 | EAGAVIRGKKGSGGIT | 80-95 (P25816) Bet v2 | 76 |
| BIR15 | SLNTLRLRRIFDLFDK | 35-50 Bet v3 | 77 |
| BIR16A | AERERIFKRFDANGEGK | 10-26 D to E variant Bet v4 | 78 |
| BIR16B | AERERIFKRFDAGGEGK | N to G variant of above | 79 |
| BIR17 | VKGKLVEKFKGLGVTLLHG | 44-62 Bet v6 | 80 |

EXAMPLE 7

In Vitro Binding Analysis

The peptides identified as being potential MHC Class II-binding are pre-screened for solubility in an aqueous, acidic milieu and the peptides are tested in an in vitro MHC Class II binding assay.

Methods

The assay employed is a competitive MHC class II binding assay, wherein each peptide is analysed for its ability to displace a known control binder from each of the human MHC class II allotypes investigated. The allotypes and control peptides used in this study are typically those shown below:

| Allotype | Control Peptide | Sequence | SEQ ID NO: |
|---|---|---|---|
| DRB1*0301 | Myco. tuberculosis/leprae hsp 65 2-16 | AKTIAYDEEARRGLE | 81 |
| DRB1*1101 | Influenza haemagglutinin 307-319 | PKYVKQNTLKLAT | 82 |
| DRB1*1501 | Human myelin basic protein 85-99 | ENPVVHFFKNIVTPR | 83 |

Each of the peptides from Tables 1 to 7 are analysed in the competition assay and screened for relative binding compared to the control peptides. Due to the nature of the competitive assay the data for each peptide is determined as a ratio of its own IC50 to that of the control peptide. Thus, a peptide that has an IC50 value that is parity to the control peptide has an identical binding affinity, while peptides with a ratio less than one have a higher affinity and those with a ratio greater than one have a lower affinity.

Solubility in aqueous solution is an essential criterion for a peptide to be an effective therapeutic agent. Therefore, as a consequence of the solubility screen very hydrophobic peptides with a high frequency of large hydrophobic amino acid residues in multiple binding registers will be eliminated. This is a characteristic of promiscuous HLA-DRB1* binders. Peptides which bind to one or more of the MHC Class II allotypes are identified. It would be expected that such peptides would have the ability to bind similar allotypes that have not been tested through the homology of MHC structures.

EXAMPLE 8

The following methods are applied to the same peptides as in Example 7.

Cell Proliferation Assay

The cell proliferation assay is performed on PBMC's ($140 \times 10^6$ cells required for all parameters to be tested). Proliferation is measured by the incorporation of the radiolabelled compound 3H-thymidine. In more detail, 100 µl of the appropriate antigen or peptide concentration is distributed into the appropriate wells of 96 well plates. The plates are then placed into a humidified 5% CO2 incubator set at 37° C. for a maximum of 4 hours. PBMC's isolated as described above are prepared to a concentration of $2 \times 10^6$ cells/ml in complete medium at room temperature. 100 µl of cell solution is then distributed into each of the wells of the 96 well plates containing antigen/peptide. The plates are then incubated for 6 to 8 days. The cultures are pulsed with tritiated thymidine solution by adding 10 µl of tritiated thymidine stock solution (1.85 MBq/ml in serum-free RPMI medium) to each well. The plates are then returned to the incubator for between 8 and 16 hours. Cultures are then harvested using a Can berra Packard FilterMate 196 cell harvester. Dried filter mats are counted using an appropriate beta scintillation counter.

Counts from wells containing peptide are compared statistically to wells containing media alone (12 wells per group). The non-parametric Mann-Whitney test is used. The same statistical test is used for all subjects. A statistically significant difference between media only wells and peptide-stimulated wells is considered a positive stimulation of PBMC's by the peptide.

Cytokine Release Assay

The 36 peptides were manufactured at small scale (approximately 10 mg batch size, non-GMP). The purity of each peptide was at least 95% by HPLC. 96 well culture plates containing peptides and controls (the negative control was culture medium and the positive controls were staphylococcal enterotoxin B (SEB) 25 ng/ml and whole birch pollen allergen extract 100 µg/ml) were prepared in advance and stored at −20° C. prior to the day of assay. Peptides were added to wells in a volume of 100 µl containing peptides at a concentration of 200 µg/ml, such that subsequent addition of 100 µl of cells would create a final assay concentration of 100 µg/ml.

Peripheral blood mononuclear cells (PBMCs) were isolated from heparinised blood by Ficoll density gradient centrifugation. A 100 µl aliquot of a $5 \times 10^6$ cell/ml PBMC suspension was then added to each well and the plates placed in a humidified 5% CO2 incubator at 37° C. for 5 days. Following stimulation, culture supernatants (100 µl) were harvested for testing by multiplex bead assay.

Multiplex cytokine bead assays (IL-10, IL-13, Interferon gamma (IFN-g)) were performed on thawed culture supernatants according to the manufacturer's instructions. Single measurements were performed for each culture supernatant sample. After completion of the multiplex assay, individual cytokine levels were determined by interpolation from the standard curve generated in the assay. A positive result was taken as being greater than 100 pg/ml for the IL-13 and IFN-g assays or >4 times the background for the IL-10 assays. The number of responders out of 47 birch allergic subjects tested was calculated for each peptide for the three cytokines. Results for IL-13 or IFN-g are summarized in Table 9.

TABLE 8

% responders indicates the proportion of subjects in which each peptide induced IL-13 or IFN-g above a threshold level of 100 pg/ml

| Peptide | % responders |
| --- | --- |
| Bir02J | 48 |
| Bir01I | 42 |
| Bir01F | 38 |
| Bir12B | 38 |
| Bir01G | 33 |
| Bir04 | 33 |
| Bir09 | 33 |
| Bir02E | 31 |
| Bir02G | 31 |
| Bir02I | 31 |
| Bir07 | 31 |
| Bir07C | 31 |
| Bir09A | 31 |
| Bir09B | 31 |
| Bir11 | 31 |
| Bir16A | 31 |
| Bir02D | 29 |
| Bir09C | 27 |
| Bir15 | 27 |
| Bir16B | 27 |
| Bir01H | 25 |
| Bir06D | 25 |
| Bir07B | 25 |
| Bir07D | 25 |
| Bir10 | 25 |
| Bir14 | 25 |
| Bir17 | 25 |
| Bir05A | 23 |
| Bir06 | 23 |
| Bir07A | 23 |
| Bir13 | 23 |
| Bir06B | 19 |
| Bir08A | 19 |
| Bir05 | 17 |
| Bir08 | 17 |
| Bir12A | 17 |

Peptides which induce positive response in a high proportion or subjects are desirable for inclusion in a vaccine. As shown, the top performing peptides were Bir02J (top of the 02 series), Bir01I (top of the 01 series) and Bir12B. The core of any vaccine should ideally contain these peptides. The second best performing peptides were Bir04 and Bir09 (top of the 09 series) which may be added to the core mixture of Bir02J, Bir01I and Bir12B. The third best performing peptides were Bir07, Bir07C, Bir11 and Bir16A. Additional peptides from this group may be added to the vaccine mixture to further increase coverage. Bir15 was the fourth best performing peptide and may also be added to the vaccine mixture. In terms of other peptides in the various series, Bir01F, 01G or 01H, in that order of preference, are useful variants of Bir01I; Bir02E, 02G, 02I or lastly 02D are useful variants of Bir02J; Bir09A, 09B or lastly 09C are useful variants of Bir09; and Bir16B is a useful variant of Bir16A. A possible preferred mixture would therefore include Bir02J, Bir01I, Bir12B, Bir04, Bir09, Bir07C and Bir16A. Bir11 and/or Bir15 may also be included, or alternatively substituted for Bir07C and/or Bir16A.

In terms of IL-10 release, Bir01I, listed above as one of the top 3 peptides for IL-13 or IFN-g production, induced IL-10 responses in 49% of individuals. Bir02I also induced IL-10 production in a high proportion of individuals (43%). Inclusion of a strong IL-10 inducing peptide may assist in the induction of tolerance following vaccination.

EXAMPLE 9

Solubility Screening

A) Introduction

TABLE 9-1

Birch peptides to be included in solubility testing

| Peptide | Sequence | Mw (Da) | Length (a.a.) | Theoretical Isoelectric point (pI) | SEQ ID NO: |
|---|---|---|---|---|---|
| BIR01I | FNYETETTSVIPAARK | 1825.92 | 16 | 6.14 | 48 |
| BIR02I | PAARMFKAFILD | 1378.74 | 12 | 9.18 | 52 |
| BIR02J | PAARMFKAFILEGDKLVPK | 2130.26 | 19 | 9.72 | 53 |
| BIR04 | PGTIKKISFPEGFPFKYV | 2054.12 | 18 | 9.56 | 54 |
| BIR07C | SNEIKIVATPEGGSILK | 1754.98 | 17 | 5.86 | 63 |
| BIR09 | ETLLRAVESYLLAHSDAY | 2050.04 | 18 | 4.65 | 67 |
| BIR09B | KEMGETLLRAVESYLLAHS | 2146.11 | 19 | 5.50 | 69 |
| BIR12B | AKYMVIQGEPGRVIRGK | 1901.07 | 17 | 10.28 | 74 |
| BIR16A | AERERIFKRFDANGEGK | 2022.04 | 17 | 8.63 | 78 |

Details of the Birch reference peptides used are indicated in Table 9-2. All peptides were manufactured by Bachem AG, Bubendorf, Switzerland.

TABLE 9-2

Details of Birch peptides

| Peptide | Batch no. | MW (Da) | Peptide purity (%) | Peptide content (%) |
|---|---|---|---|---|
| BIR1I | 1028882 | 1827.03 | 99.2 | 87.1 |
| BIR02I | 1028883 | 1379.69 | 99.1 | 86.2 |
| BIR02J | 1028884 | 2131.61 | 97.4 | 84.1 |
| BIR04 | 1028885 | 2055.45 | 98.1 | 88.3 |
| BIR07C | 1029310 | 1756.03 | 97.9 | 89.8 |
| BIR09 | 1028886 | 2051.28 | 97.5 | 86.9 |
| BIR09B | 1029311 | 2147.48 | 97.3 | 89.4 |

B)
Solubility Testing

A series of matrices containing 260 mM trehalose and spanning a pH range of 3.0 to 7.0 plus a solution modified with 2 mM HCl were prepared as indicated in Appendix 2. The solubility of each of the nine peptides was evaluated in each of the matrices in accordance with Appendix 1. Where solubility was achieved initially, but the peptide precipitated out of solution subsequently then an additional quantity of the relevant matrix was added to try and achieve solubility of the peptide at ca. 200 μM.

TABLE 9-2-continued

Details of Birch peptides

| Peptide | Batch no. | MW (Da) | Peptide purity (%) | Peptide content (%) |
|---|---|---|---|---|
| BIR12B | 1028887 | 1902.30 | 97.3 | 85.9 |
| BIR16A | 1028888 | 2023.24 | 98.4 | 88.1 |

C) Results

The results of the solubility screening are displayed in tables 9-3 to 9-8 below:

TABLE 3

2 mM HCl and 260 mM trehalose dihydrate, pH 2.65

| | 2 mM hydrochloric Acid | | Weight of peptide 'as is' (mg) | Volume required (μL) | Solubility [mg per ml 'as is'] | Solubility [mg per ml] | Solubility [μmol per ml] |
|---|---|---|---|---|---|---|---|
| Peptide | Comments | Solubility after 24 Hours | | | | | |
| BIR1I | Completely dissolved | Completely dissolved | 0.975 | 50 | 19.50 | 16.849 | 9.222 |
| BIR02I | Completely dissolved | Completely dissolved | 1.175 | 50 | 23.50 | 20.075 | 14.550 |
| BIR02J | Completely dissolved | Completely dissolved | 1.180 | 50 | 23.60 | 19.332 | 9.069 |
| BIR04 | Completely dissolved | Completely dissolved | 1.025 | 50 | 20.50 | 17.758 | 8.639 |
| BIR07C | Completely dissolved | Completely dissolved | 1.148 | 100 | 11.48 | 10.093 | 5.747 |
| BIR09 | Completely dissolved• filter debris | Completely dissolved• filter debris | 1.147 | 1250 | 0.92 | 0.777 | 0.379 |

TABLE 3-continued 2 mM HCl and 260 mM trehalose dihydrate, pH 2.65

| | 2 mM hydrochloric Acid | | Weight of peptide | Volume required | Solubility [mg per | Solubility | Solubility [μmol |
|---|---|---|---|---|---|---|---|
| Peptide | Comments | Solubility after 24 Hours | 'as is' (mg) | (μL) | ml 'as is'] | [mg per ml] | per ml] |
| BIR09B | Completely dissolved | Completely dissolved | 1.220 | 100 | 12.20 | 10.612 | 4.942 |
| BIR12B | Completely dissolved | Completely dissolved | 1.022 | 100 | 10.22 | 8.542 | 4.490 |
| BIR16A | Completely dissolved | Completely dissolved | 1.243 | 50 | 24.86 | 21.551 | 10.652 |

TABLE 4$^a$ 10 mM sodium citrate and 260 mM trehalose dihydrate, pH 3.01

| | Citrate buffer pH 3.0 | | Weight of peptide | Volume required | Solubility [mg per | Solubility | Solubility [μmol |
|---|---|---|---|---|---|---|---|
| Peptide | Comments | Solubility after 24 Hours | 'as is' (mg) | (μL) | ml 'as is'] | [mg per ml] | per ml] |
| BIR1I | Completely dissolved | Completely dissolved | 1.071 | 650 | 1.65 | 1.424 | 0.779 |
| BIR02I | Completely dissolved | Completely dissolved | 1.112 | 1100 | 1.01 | 0.864 | 0.626 |
| BIR02J | Completely dissolved in 100 uL, redissolved in 3 mL after 24 hrs | Precipitated out, redissolved | 1.150 | 3000 | 0.38 | 0.314 | 0.147 |
| BIR04 | Completely dissolved | Completely dissolved | 1.129 | 50 | 22.58 | 19.559 | 9.516 |
| BIR07C | Completely dissolved | Completely dissolved | 1.108 | 850 | 1.30 | 1.146 | 0.653 |
| BIR09 | Undissolved in 1.5 mL• diluted to 3 mL still undissolved | Undissolved | 1.111 | 3000 | 0.37 | 0.314 | 0.153 |
| BIR09B | Completely dissolved | Completely dissolved | 1.162 | 100 | 11.62 | 10.108 | 4.707 |
| BIR12B | Completely dissolved | Completely dissolved | 1.094 | 200 | 5.47 | 4.572 | 2.403 |
| BIR16A | Completely dissolved | Completely dissolved | 1.076 | 150 | 7.17 | 6.219 | 3.074 |

TABLE 4$^b$ 10 mM sodium citrate and 260 mM trehalose dihydrate, pH 3.99

| | Citrate buffer pH 4.0 | | Weight of peptide | Volume required | Solubility [mg per | Solubility | Solubility [μmol |
|---|---|---|---|---|---|---|---|
| Peptide | Comments | Solubility after 24 Hours | 'as is' (mg) | (μL) | ml 'as is'] | [mg per ml] | per ml] |
| BIR1I | Completely dissolved | Completely dissolved | 1.026 | 450 | 2.28 | 1.970 | 1.078 |
| BIR02I | Cloudy solution with suspended material. Frothing on vortex | Undissolved | 1.051 | 3000 | 0.35 | 0.299 | 0.217 |
| BIR02J | Completely dissolved in 50 uL, redissolved in 3 mL after 24 hrs | Precipitated out, redissolved | 1.155 | 3000 | 0.39 | 0.315 | 0.148 |
| BIR04 | Completely dissolved | Completely dissolved | 1.018 | 50 | 20.36 | 17.636 | 8.580 |
| BIR07C | Cloudy solution with suspended material. Frothing on vortex | Cloudy solution with suspended material | 1.126 | 3000 | 0.38 | 0.330 | 0.188 |
| BIR09 | Cloudy solution with undissolved material | Cloudy solution with undissolved material | 1.074 | 3000 | 0.36 | 0.303 | 0.148 |
| BIR09B | Completely dissolved | Completely dissolved | 1.140 | 100 | 11.40 | 9.916 | 4.618 |
| BIR12B | Completely dissolved | Completely dissolved | 1.032 | 100 | 10.32 | 8.626 | 4.534 |
| BIR16A | Completely dissolved | Completely dissolved | 1.123 | 150 | 7.49 | 6.490 | 3.208 |

TABLE 5

10 mM sodium citrate and 260 mM trehalose dihydrate, pH 5.02

| | Citrate buffer pH 5.0 | | Weight of peptide 'as is' (mg) | Volume required (μL) | Solubility [mg per ml 'as is'] | Solubility [mg per ml] | Solubility [μmol per ml] |
|---|---|---|---|---|---|---|---|
| Peptide | Comments | Solubility after 24 Hours | | | | | |
| BIR1I | Completely dissolved | Completely dissolved | 1.036 | 450 | 2.30 | 1.989 | 1.089 |
| BIR02I | Cloudy solution with suspended material | Completely dissolved | 1.085 | 3000 | 0.36 | 0.309 | 0.224 |
| BIR02J | Completely dissolved in 150 uL, redissolved in 3 mL after 24 hrs | Precipitated out, redissolved | 1.029 | 3000 | 0.34 | 0.281 | 0.132 |
| BIR04 | Completely dissolved | Completely dissolved | 1.076 | 50 | 21.52 | 18.641 | 9.069 |
| BIR07C | Completely dissolved | Completely dissolved | 1.167 | 1350 | 0.86 | 0.760 | 0.433 |
| BIR09 | Clear solution with suspended material | Clear solution with suspended material | 1.115 | 3000 | 0.37 | 0.315 | 0.154 |
| BIR09B | Completely dissolved | Completely dissolved | 1.275 | 100 | 12.75 | 11.091 | 5.165 |
| BIR12B | Completely dissolved | Completely dissolved | 1.167 | 200 | 5.84 | 4.877 | 2.564 |
| BIR16A | Completely dissolved | Completely dissolved | 1.158 | 50 | 23.16 | 20.077 | 9.923 |

TABLE 6

10 mM sodium citrate and 260 mM trehalose dihydrate, pH 6.01

| | Citrate buffer pH 6.0 | | Weight of peptide 'as is' (mg) | Volume required (μL) | Solubility [mg per ml 'as is'] | Solubility [mg per ml] | Solubility [μmol per ml] |
|---|---|---|---|---|---|---|---|
| Peptide | Comments | Solubility after 24 Hours | | | | | |
| BIR1I | Completely dissolved | Completely dissolved | 1.117 | 150 | 7.45 | 6.434 | 3.522 |
| BIR02I | Cloudy solution with suspended material | Cloudy solution with suspended material | 1.143 | 3000 | 0.38 | 0.325 | 0.236 |
| BIR02J | Completely dissolved in 100 uL, redissolved in 3 mL after 24 hrs | Precipitated out, redissolved | 1.172 | 3000 | 0.39 | 0.320 | 0.150 |
| BIR04 | Completely dissolved. Evidence of filter debris | Completely dissolved. Filter debris | 1.011 | 100 | 10.11 | 8.758 | 4.261 |
| BIR07C | Completely dissolved in 350 uL, redissolved in 3 mL after 24 hrs | Precipitated out, redissolved | 1.045 | 3000 | 0.35 | 0.306 | 0.174 |
| BIR09 | Completely dissolved | completely dissolved | 1.084 | 1050 | 1.03 | 0.875 | 0.426 |
| BIR09R | Completely dissolved | Completely dissolved | 1.230 | 250 | 4.92 | 4.280 | 1.993 |
| BIR12B | Completely dissolved. Evidence of filter debris | Completely dissolved. Filter debris | 1.026 | 450 | 2.28 | 1.906 | 1.002 |
| BIR16A | Completely dissolved | Completely dissolved | 1.293 | 50 | 25.86 | 22.418 | 11.080 |

TABLE 7

10 mM potassium dihydrogen phosphate and 260 mM trehalose dihydrate, pH 6.03

| | Phosphate buffer pH 6.0 | | Weight of peptide 'as is' (mg) | Volume required (μL) | Solubility [mg per ml 'as is'] | Solubility [mg per ml] | Solubility [μmol per ml] |
|---|---|---|---|---|---|---|---|
| Peptide | Commute | Solubility after 24 Hours | | | | | |
| BIR1I | Completely dissolved | Completely dissolved | 1.107 | 50 | 22.14 | 19.130 | 10.470 |
| BIR02I | Completely dissolved | Completely dissolved | 1.145 | 100 | 11.45 | 9.781 | 7.089 |
| BIR02J | Completely dissolved | Completely dissolved | 1.112 | 100 | 11.12 | 9.109 | 4.273 |
| BIR04 | Completely dissolved | Completely dissolved | 0.986 | 100 | 9.86 | 8.541 | 4.155 |
| BIR07C | Completely dissolved in 250 uL, redissolved in 3 mL after 24 hrs | Precipitated out, redissolved | 1.245 | 3000 | 0.42 | 0.365 | 0.208 |
| BIR09 | Cloudy solution with suspended material | Cloudy solution with suspended material | 1.037 | 3000 | 0.35 | 0.293 | 0.143 |
| BIR09B | Completely dissolved in 100 uL, redissolved in 3 mL after 24 hrs | Precipitated out, redissolved | 1.086 | 3000 | 0.36 | 0.315 | 0.147 |
| BIR12B | Completely dissolved | Completely dissolved | 1.192 | 50 | 23.84 | 19.926 | 10.474 |
| BIR16A | Completely dissolved | Completely dissolved | 1.077 | 50 | 21.54 | 18.673 | 9.229 |

TABLE 8

| | 10 mM potassium dihydrogen phosphate and 260 mM trehalose dihydrate, pH 7.03 | | | | | | |
|---|---|---|---|---|---|---|---|
| | Phosphate buffer pH 7.0 | | Weight of peptide 'as is' (mg) | Volume required (μL) | Solubility [mg per ml 'as is'] | Solubility [mg per ml] | Solubility [μmol per ml] |
| Peptide | Comments | Solubility after 24 Hours | | | | | |
| BIR1I | Completely dissolved | Completely dissolved | 1.039 | 50 | 20.78 | 17.955 | 9.827 |
| BIR02I | Completely dissolved | Completely dissolved | 1.190 | 100 | 11.90 | 10.165 | 7.368 |
| BIR02J | Completely dissolved | Completely dissolved | 1.231 | 100 | 12.31 | 10.084 | 4.730 |
| BIR04 | Completely dissolved | Completely dissolved | 1.075 | 50 | 21.50 | 18.624 | 9.061 |
| BIR07C | Completely dissolved | Completely dissolved | 1.005 | 150 | 6.70 | 5.890 | 3.354 |
| BIR09 | Completely dissolved | Completely dissolved | 1.138 | 750 | 1.52 | 1.286 | 0.627 |
| BIR09B | Completely dissolved | Completely dissolved | 1.085 | 50 | 21.70 | 18.876 | 8.790 |
| BIR12B | Completely dissolved | Completely dissolved | 1.031 | 50 | 20.62 | 17.234 | 9.060 |
| BIR16A | Completely dissolved | Completely dissolved | 1.099 | 50 | 21.98 | 19.055 | 9.418 |

EXAMPLE 9

Annex 1

Peptide Solubility Studies
Solubility Methodology
The formulation vehicles were prepared and measurement of pH taken.
  Weighing of peptides.
    Approximately 1 mg was required for each evaluation.
    Materials were dispensed into containers suitable for subsequent solubility evaluation, i.e. clear glass HPLC vials (with screw cap).
  Evaluation of solubility (for each matrix).
    Aliquots of matrix (50 to 100~L) were added as required.
    The peptide solubility was interpreted by visual inspection.
    The description of the sample characteristics following addition of each aliquot of the solvent was recorded.
    Repeat visual assessment of solubility after 24 hours.
    Where a peptide precipitated out of solution after 24 hours, additional buffer was added to produce a final concentration of ca. 0.2 mM (200 nmol per mL should equate to roughly 0.35 mg/mL).
  Calculation of peptide solubilities (initial evaluation).
    Based on absolute amount of powder weighed.
    Determination of molar concentration at which solubility was achieved using peptide molecular masses and peptide content and purity values.
Calculations $$\text{Solubility mg/ml 'as is'} = \frac{\text{weight(mg)}}{\text{dilution}(\mu l)} \times 1000$$

$$\text{Solubility mg/ml} = \frac{\text{weight(mg)}}{\text{dilution}(\mu l)} \times 1000 \times \% \text{ Content} \times \% \text{ Purity}$$

Solubility μmol/ml =

$$\frac{\text{weight(mg)}}{\text{dilution}(\mu l)} \times 1000 \times \% \text{ Content} \times \% \text{ Purity} \times \frac{1}{\text{MolWt}} \times 1000$$

EXAMPLE 9

Annex 2

Buffers for Initial Solubility and Stability Screening
  Each matrix was prepared at a concentration of 10 mM of the buffering agent. Each buffer contained 260 mM Trehalose dihydrate (FW 378.3).
Preparation of Matrix
  The procedure indicated is for the preparation of 100 mL of each buffer, but alternative volumes can be prepared by adjusting the quantities.
    0.1M stock solutions of sodium citrate and potassium dihydrogen phosphate were prepared.
    Weight of trehalose dihydrate equivalent to 260 mM was transferred to an appropriate mixing vessel containing 70-80 mL of distilled deionised water and allowed to dissolve.
    10 mL of the appropriate stock 0.1M buffer solution was added to the mixing vessel and stirred.
    The pH of the matrix was adjusted to the desired value by adding 2 mM hydrochloric acid or 0.1M sodium hydroxide as required.
    The solutions were finally diluted to 100 g weight and the pH re-assessed.
  Buffers for initial solubility and stability screening, shown as Buffer salt or pH modifier/pH:
  2 mM HCl and 260 mM trehalose dihydrate/pH 2.65
  10 mM sodium citrate and 260 mM trehalose dihydrate/pH 3.01
  10 mM sodium citrate and 260 mM trehalose dihydrate/pH 3.99
  10 mM sodium citrate and 260 mM trehalose dihydrate/pH 5.02
  10 mM sodium citrate and 260 mM trehalose dihydrate/pH 6.01
  10 mM potassium dihydrogen phosphate and 260 mM trehalose dihydrate/pH 6.03
  10 mM potassium dihydrogen phosphate and 260 mM trehalose dihydrate/pH 7.03

EXAMPLE 10

Histamine Release Assay

The purpose of this assay was to identify compositions that are capable of activating blood basophils (as a surrogate for tissue mast cells) resulting in histamine release that may result in allergic reactions during therapy. A composition comprising a mixture of peptides that induce histamine release frequently may be considered unsuitable for use as a vaccine.

Histamine release requires the crosslinking of adjacent specific IgE molecules on the surface of the basophil. The peptides being evaluated were small (11 to 18 amino acids in length) and should not, therefore, possess significant tertiary structure that would enable them to retain the conformation of an IgE-binding epitope of the whole molecule. Furthermore, peptide monomers in solution, even if they are bound by IgE, should not be able to crosslink adjacent IgE molecules.

Histamine release from fresh peripheral whole blood from birch allergic subjects was evaluated. Peripheral blood basophils were used as a surrogate for tissue mast cells which were not practical to assay. Blood was incubated in vitro with mixtures of peptides identified as suitable based on the results of Examples 1 to 9 above. Specifically, the following mixtures were assayed:

Mix 1—BIR01I, BIR02J, BIR04, BIR12B, BIR16A, BIR07C
Mix 2—BIR01I, BIR02J, BIR04, BIR12B, BIR16A, BIR07C, BIR09
Mix 3—BIR01I, BIR02J, BIR04, BIR12B, BIR16A, BIR07C, BIR09B
Mix 4—BIR01I, BIR02I, BIR04, BIR12B, BIR16A, BIR07C
Mix 5—BIR01I, BIR02I, BIR04, BIR12B, BIR16A, BIR07C, BIR09
Mix 6—BIR01H, BIR02I, BIR04, BIR12B, BIR16A, BIR07C, BIR09B

Histamine release in response to whole birch allergen extract was measured in each subject to confirm basophil sensitisation. A positive control, representing total histamine release, generated by freeze/thawing the cells twice, was included in each assay. A negative control for spontaneous histamine release was generated by incubating cells in buffer only.

The assay was performed using the Immunotech Histamine Release Immunoassay kit according to the manufacturer's instructions. Following the in vitro challenge of blood basophils with peptide mixtures, whole allergen or buffer in microtitre plate wells, supernatants were removed and the histamine in the samples converted to acyl histamine. Acylated samples were tested by a competitive acyl histamine ELISA.

Peptide mixtures were assayed for their ability to induce histamine release over a 5 log 10 range (1 to 10,000 ng/ml). The concentration range assayed was selected based on theoretical in vivo doses of peptide that may be achieved during therapy. For example, a 31 µg dose (approximately 3 nmol/peptide equivalent) of each peptide entering a blood volume of 5 litres, would result in a blood concentration of 6 ng/ml, at the lower end of the histamine release assay dose range. The whole birch allergen extract was used over the same concentration range.

Single measurements were performed for each dilution. After completion of the ELISA, individual histamine levels were determined by interpolation from the standard curve generated in the ELISA assay. Results from samples were adjusted to allow for dilution. Where two or more consecutive dilutions of a peptide/allergen preparation elicited >15% of the total histamine release seen in the freeze thawed positive control (>15% of positive control), or where a single value of >15% of positive control was achieved at the highest concentration tested (10 µg/mL for peptides), this was considered a "positive histamine release".

A total of 40 histamine release assays were completed during the study. Of these 5 assays were rejected because of failure to meet appropriate QC controls, e.g. due to unacceptably high levels (>15% of positive control) of spontaneous release in the medium plus buffer negative control wells.

The mixtures tested all showed good histamine release properties. The study findings are summarised as follows: (WA=whole allergen)

| Mix | Peptide conc: µg/ml | Average % histamine release |
| --- | --- | --- |
| 1 | 10 | 1% |
| 1 | 1 | 2% |
| 1 | 0.1 | 3% |
| 1 | 0.01 | 3% |
| 1 | 0.001 | 2% |
| 2 | 10 | 2% |
| 2 | 1 | 2% |
| 2 | 0.1 | 3% |
| 2 | 0.01 | 3% |
| 2 | 0.001 | 2% |
| 3 | 10 | 4% |
| 3 | 1 | 2% |
| 3 | 0.1 | 3% |
| 3 | 0.01 | 2% |
| 3 | 0.001 | 2% |
| 4 | 10 | 2% |
| 4 | 1 | 2% |
| 4 | 0.1 | 2% |
| 4 | 0.01 | 1% |
| 4 | 0.001 | 1% |
| 5 | 10 | 2% |
| 5 | 1 | 2% |
| 5 | 0.1 | 2% |
| 5 | 0.01 | 2% |
| 5 | 0.001 | 2% |
| 6 | 10 | 3% |
| 6 | 1 | 2% |
| 6 | 0.1 | 1% |
| 6 | 0.01 | 1% |
| 6 | 0.001 | 2% |
| WA | 10 | 65% |
| WA | 1 | 38% |
| WA | 0.1 | 38% |
| WA | 0.01 | 42% |
| WA | 0.001 | 43% |

The invention claimed is:

1. A composition suitable for use in treating allergy to birch pollen, said composition comprising
the polypeptide of SEQ ID NO: 74 (Bir12B; AKYM-VIQGEPGRVIRGK), the polypeptide of SEQ ID NO: 53 (Bir02J; PAARMFKAFILEGDKLVPK), the polypeptide of SEQ ID NO: 48 (Bir01I; FNYETETTS-VIPAARK), the polypeptide of SEQ ID NO: 54 (Bir04; PGTIKKISFPEGFPFKYV), the polypeptide of SEQ ID NO: 63 (Bir07C; SNEIKIVATPEGGSILK), the polypeptide of SEQ ID NO: 78 (Bir16A; AERER-IFKRFDANGEGK), and the polypeptide of SEQ ID NO: 69 (Bir09B; KEMGETLLRAVESYLLAHS); wherein each polypeptide is present in an amount of 100 ng to 2 mg.

2. The composition according to claim 1, which is a solution comprising each polypeptide at a concentration in the range of 0.03 to 200 nmol/ml.

3. The composition according to claim 1, which is a pharmaceutical composition further comprising a pharmaceutically acceptable carrier or diluent.

4. An in vitro method of determining whether T cells recognize a composition according to claim 1 comprising contacting said T cells with said composition and detecting whether said T cells are stimulated by said composition.

5. A method according to claim 4 which is carried out to determine whether an individual has, or is at risk of having, an allergy to birch pollen.

6. The composition according to claim 3, which is formulated for oral administration, nasal administration, topical administration, subcutaneous administration, sublingual administration, intradermal administration, buccal administration, epidermal administration, or for administration by inhalation, by injection, or by patch.

7. A method of or treating allergy to birch pollen, the method comprising administering to a subject in need of such treatment a therapeutically effective amount of a composition comprising
the polypeptide of SEQ ID NO: 74 (Bir12B; AKYM-VIQGEPGRVIRGK), the polypeptide of SEQ ID NO: 53 (Bir02J; PAARMFKAFILEGDKLVPK), the polypeptide of SEQ ID NO: 48 (Bir01I; FNYETETTS-VIPAARK), the polypeptide of SEQ ID NO: 54 (Bir04; PGTIKKISFPEGFPFKYV), the polypeptide of SEQ ID NO: 63 (Bir07C; SNEIKIVATPEGGSILK), the polypeptide of SEQ ID NO: 78 (Bir16A; AERER-IFKRFDANGEGK), and the polypeptide of SEQ ID NO: 69 (Bir09B; KEMGETLLRAVESYLLAHS); wherein each polypeptide is administered at a dose of 100 ng to 2 mg.

8. The method according to claim 7, wherein the composition is a solution comprising each polypeptide at a concentration in the range of 0.03 to 200 nmol/ml.

9. The method according to claim 7, wherein the composition is a pharmaceutical composition further comprising a pharmaceutically acceptable carrier or diluent.

10. The method according to claim 9, wherein the composition is formulated for oral administration, nasal administration, topical administration, subcutaneous administration, sublingual administration, intradermal administration, buccal administration, epidermal administration, or for administration by inhalation, by injection, or by patch.

11. The composition according to claim 1, wherein no further polypeptides from a birch pollen allergen are present.

12. The composition according to claim 1, wherein each polypeptide is present in an amount of 1 µg to 50 µg.

13. The composition according to claim 1, wherein each polypeptide is present in an amount of 2 µg to 25 µg.

14. The composition according to claim 3, which is in dry powder form.

15. The method according to claim 8, wherein the composition which is in the form of a sterile injectable formulation comprising a non-toxic parenterally-acceptable diluents or solvent.

16. The method according to claim 7, wherein no further polypeptides from a birch pollen allergen are present in the composition.

17. The method according to claim 7, wherein each polypeptide is administered in a dose of of 1 µg to 50 µg.

18. The method according to claim 7, wherein each polypeptide is administered in a dose of 2 µg to 25µg.

19. The method according to claim 9, wherein the composition is administered in the form of a sterile injectable formulation comprising a non-toxic parenterally-acceptable diluents or solvent.

20. A method of treating allergy to birch pollen in an individual, the method comprising:
testing an individual for sensitisation to birch pollen; and
administering to the said individual, who has been determined by said testing to be sensitised to birch pollen, a therapeutically effective amount of a composition comprising the polypeptide of SEQ ID NO: 74 (Bir12B; AKYMVIQGEPGRVIRGK), the polypeptide of SEQ ID NO: 53 (Bir02J; PAARMFKAFILEGDKLVPK), the polypeptide of SEQ ID NO: 48 (Bir01I; FNYETETTSVIPAARK), the polypeptide of SEQ ID NO: 54 (Bir04; PGTIKKISFPEGFPFKYV), the polypeptide of SEQ ID NO: 63 (Bir07C; SNEIKIVATPEGGSILK), the polypeptide of SEQ ID NO: 78 (Bir16A; AERERIFKRFDANGEGK) and the polypeptide of SEQ ID NO: 69 (Bir09B; KEMGETLLRAVESYLLAHS).

* * * * *

UNITED STATES PATENT AND TRADEMARK OFFICE
CERTIFICATE OF CORRECTION

PATENT NO. : 9,017,689 B2
APPLICATION NO. : 13/578888
DATED : April 28, 2015
INVENTOR(S) : Roderick Peter Hafner et al.

It is certified that error appears in the above-identified patent and that said Letters Patent is hereby corrected as shown below:

In the specification

Column 3, Lines 55-56, replace "(Bir07C; SNEIKIVATPEGGSTLK)" with
--(Bir07C; SNEIKIVATPEGGSILK)--

Column 12, Line 20, replace "in the upto three amino acids" with --in the up to three amino acids--

Line 25, replace "in the upto four amino acids" with --in the up to four amino acids--

In the claims

Column 127, Lines 15-16, replace "composition which is" with --composition is--

Line 17, replace "diluents" with --diluent--

Line 23, replace "in a dose of of" with --in a dose of--

Column 128, Line 6, replace "diluents" with --diluent--

Signed and Sealed this
Twentieth Day of October, 2015

Michelle K. Lee
*Director of the United States Patent and Trademark Office*